United States Patent
Teng et al.

(10) Patent No.: US 6,534,544 B1
(45) Date of Patent: Mar. 18, 2003

(54) METHODS OF TREATMENT WITH COMPOUNDS HAVING RARα RECEPTOR SPECIFIC OR SELECTIVE ACTIVITY

(75) Inventors: Min Teng, Aliso Viejo, CA (US); Tien T. Duong, Irvine, CA (US); Roshantha A. Chandraratna, Mission Viejo, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/350,310

(22) Filed: Jul. 9, 1999

Related U.S. Application Data

(62) Division of application No. 08/580,553, filed on Dec. 29, 1995, now Pat. No. 5,965,606.

(51) Int. Cl.[7] .................. A61K 31/195; A61K 31/35; A61K 31/415; A61K 31/225; A61K 31/19

(52) U.S. Cl. .................. 514/563; 514/456; 514/405; 514/569; 514/544

(58) Field of Search ................................ 514/563, 456, 514/405, 725, 569, 548, 352

(56) References Cited

U.S. PATENT DOCUMENTS

| | | |
|---|---|---|
| 4,096,341 A | 6/1978 | Frazer |
| 4,326,055 A | 4/1982 | Loeliger |
| 4,391,731 A | 7/1983 | Boller et al. ........... 252/299.26 |
| 4,695,649 A | 9/1987 | Magami et al. |
| 4,723,028 A | 2/1988 | Shudo |
| 4,739,098 A | 4/1988 | Chandraratna |
| 4,740,519 A | 4/1988 | Shroot et al. |
| 4,810,804 A | 3/1989 | Chandraratna |
| 4,826,969 A | 5/1989 | Maignan et al. |
| 4,826,984 A | 5/1989 | Berlin et al. ............... 546/134 |
| 4,855,320 A | 8/1989 | Chatterjee et al. |
| 4,895,868 A | 1/1990 | Chandraratna |
| 4,927,947 A | 5/1990 | Chandraratna ............... 549/484 |
| 4,980,369 A | 12/1990 | Chandraratna |
| 4,992,468 A | 2/1991 | Chandraratna |
| 5,006,550 A | 4/1991 | Chandraratna |
| 5,013,744 A | 5/1991 | Chandraratna |
| 5,015,658 A | 5/1991 | Chandraratna |
| 5,023,341 A | 6/1991 | Chandraratna |
| 5,037,825 A | 8/1991 | Klaus et al. ............. 514/233.8 |
| 5,045,551 A | 9/1991 | Chandraratna |
| 5,053,523 A | 10/1991 | Chandraratna |
| 5,068,252 A | 11/1991 | Chandraratna |
| 5,089,509 A | 2/1992 | Chandraratna |
| 5,130,335 A | 7/1992 | Chandraratna |
| 5,134,159 A | 7/1992 | Chandraratna |
| 5,162,546 A | 11/1992 | Chandraratna ............... 549/23 |
| 5,175,185 A | 12/1992 | Chandraratna ............... 514/445 |
| 5,183,827 A | 2/1993 | Chandraratna ............... 514/444 |
| 5,202,471 A | 4/1993 | Chandraratna ............... 562/473 |
| 5,231,113 A | 7/1993 | Chandraratna ............... 514/510 |
| 5,234,926 A | 8/1993 | Chandraratna ............... 514/253 |
| 5,248,777 A | 9/1993 | Chandraratna ............... 546/165 |
| 5,264,456 A | 11/1993 | Chandraratna ............... 514/461 |
| 5,264,578 A | 11/1993 | Chandraratna ............... 546/269 |
| 5,272,156 A | 12/1993 | Chandraratna ............... 514/314 |
| 5,278,318 A | 1/1994 | Chandraratna ............... 549/23 |
| 5,324,744 A | 6/1994 | Chandraratna ............... 514/456 |
| 5,324,840 A | 6/1994 | Chandraratna ............... 546/318 |
| 5,326,898 A | 7/1994 | Chandraratna ............... 560/17 |
| 5,344,959 A | 9/1994 | Chandraratna ............... 560/100 |
| 5,346,895 A | 9/1994 | Chandraratna ............... 514/247 |
| 5,346,915 A | 9/1994 | Chandraratna ............... 514/432 |
| 5,348,972 A | 9/1994 | Chandraratna ............... 514/432 |
| 5,348,975 A | 9/1994 | Chandraratna ............... 514/456 |
| 5,349,105 A | 9/1994 | Chandraratna ............... 564/163 |
| 5,354,752 A | 10/1994 | Chandraratna ............... 514/252 |
| 5,380,877 A | 1/1995 | Chandraratna ............... 549/60 |
| 5,391,753 A | 2/1995 | Chandraratna ............... 546/63 |
| 5,399,561 A | 3/1995 | Chandraratna ............... 514/252 |
| 5,399,586 A | 3/1995 | Davies et al. ............... 514/448 |
| 5,407,937 A | 4/1995 | Chandraratna ............... 514/256 |
| 5,414,007 A | 5/1995 | Chandraratna ............... 514/365 |
| 5,420,145 A | 5/1995 | Shudo ........................ 514/428 |
| 5,426,118 A | 6/1995 | Chandraratna ............... 514/337 |
| 5,434,173 A | 7/1995 | Chandraratna ............... 514/354 |
| 5,451,605 A | 9/1995 | Chandraratna et al. ..... 514/475 |
| 5,455,265 A | 10/1995 | Chandraratna ............... 514/448 |
| 5,468,879 A | 11/1995 | Chandraratna ............... 549/23 |
| 5,470,999 A | 11/1995 | Chandraratna ............... 560/100 |
| 5,475,022 A | 12/1995 | Chandraratna ............... 514/448 |
| 5,475,113 A | 12/1995 | Chandraratna ............... 548/203 |
| 5,489,584 A | 2/1996 | Vuligonda et al. .......... 514/188 |
| 5,498,755 A | 3/1996 | Chandraratna et al. ..... 564/272 |
| 5,498,795 A | 3/1996 | Song et al. ................. 562/474 |
| 5,965,606 A | * 10/1999 | Teng et al. ................. 514/456 |

FOREIGN PATENT DOCUMENTS

| | | | |
|---|---|---|---|
| DE | 3316932 | 11/1983 | .......... C07C/63/66 |
| DE | 3524199 | 1/1986 | .......... C07C/63/66 |
| DE | 3602473 | 7/1987 | ......... C07C/43/215 |
| DE | 3708060 | 9/1987 | ......... C07D/311/04 |
| DE | 3715955 | 11/1987 | .......... C07C/15/58 |

(List continued on next page.)

OTHER PUBLICATIONS

Dawson et al., 1995, Cancer Res., 55(19), 4446–51.*
Rudd et al., 1993, Cancer Lett. (Shannon, Irel.), 73(1), 41–9.*

(List continued on next page.)

*Primary Examiner*—Zohreh Fay
*Assistant Examiner*—Brian-Yong S. Kwon
(74) *Attorney, Agent, or Firm*—Gabor L. Szekeres; Robert J. Baran; Martin A. Voet

(57) ABSTRACT

Retinoid compounds which act specifically or selectively on $RAR_\alpha$ receptor subtypes in preference over $RAR_\beta$ and $RAR_\Gamma$ receptor subtypes, possess desirable pharmaceutical properties associated with retinoids, and are particularly suitable for treatment of tumors, such as acute monocytic leukemia, cervical carcinoma, myeloma, ovarian carcinomas and head and neck carcinomas, without having one or more undesirable side effects of retinoids, such as inducement of weight loss, mucocutaneous toxicity, skin irritation and teratogenecity.

3 Claims, 4 Drawing Sheets

FOREIGN PATENT DOCUMENTS

| EP | 0098591 | 1/1984 | ......... C07D/333/54 |
|---|---|---|---|
| EP | 0130795 | 1/1985 | ......... C07D/311/58 |
| EP | 170105 A0 | 2/1986 | |
| EP | 0176032 | 4/1986 | ........... C07C/65/38 |
| EP | 0176033 | 4/1986 | ......... C07D/261/18 |
| EP | 0253302 | 1/1988 | ......... C07D/213/16 |
| EP | 0272921 | 6/1988 | ......... C07D/213/80 |
| EP | 0284288 | 9/1988 | ......... C07D/401/04 |
| EP | 0303915 | 2/1989 | ......... A61K/31/255 |
| EP | 176034 A | 4/1989 | ........... C07C/63/66 |
| EP | 0315071 | 5/1989 | ........... C07C/63/66 |
| EP | 0350846 | 7/1989 | ......... C07D/311/85 |
| EP | 0514269 | 11/1992 | ......... C07C/257/08 |
| EP | 0661259 | 5/1995 | ......... C07C/233/81 |
| GB | 2190378 | 11/1987 | ........... C07C/39/21 |
| WO | 85/00806 | 2/1985 | ........... A61K/31/00 |
| WO | 85/04652 | 10/1985 | ........... A61K/31/19 |
| WO | 91/16051 | 10/1991 | ........... A61K/31/44 |
| WO | 92/06948 | 4/1992 | ........... C07C/69/86 |
| WO | 93/03713 | 3/1993 | ........... A61K/31/07 |

OTHER PUBLICATIONS

A General Synthesis of Terminal and Internal Arylalkynes by the Palladium–Catalyzed Reaction of Alkynylzinc Reagents with Aryl Halides by Anthony O. King and Ei–i-chi, Negishi, *J. Org. Chem.*, (1978) 43/2: p. 358.

Conversion of Methyl Ketones into Terminal Acetylenes and (E)–Tri–substituted Olefins of Terpenoid Origin by Ei–ichi, et al., *J. Org. Chem.*, (1980) 45/12: p. 2526.

Sporn et al. in *J. Amer. Acad. Derm.*., (1986) 15:756–764.

"A Convenient Synthesis of Ethynylarenes and Diethyny-larenes" by S. Takahashi et al. *Synthesis* (1980) p. 627–630.

Shudo et al. in *Chem. Phar. Bull.*, (1985) 33:404–407.

Kagechika et al. in *J. Med. Chem.*, (1988) 31:2182–2192.

Chemistry and Biology of Synthetic Retinoids by Marcia I. Dawson and William H. Okamura, published by CRC Press Inc., 1990, p. 334–335, 354.

Synthesis of 2,2'–Diacyl–1,1'–Biaryls, Regiocontrolled Protection of . . . by Mervic, et al, *J. Org. Chem.*, (1980) No. 45, p. 4720–4725.

A Dopamine Receptor Model and Its Application in the Design of a New Class of Rigid Pyrrolo[2,3–g]isoquinoline Antipsychotics, Gary L. Olson et al. *American Chemical Societe*, (1981) 24/9:1026–1031.

6.2.3 Conformational Restriction, Williams, et al., *Drug Discovery and Development*, The Humana Press, (1987) pp. 54–55.

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3:.

"Synthesis and Evaluation of Stilbene and Dihydrostilbene Derivateives as Potential Anticancer Agents That Inhibit Tubulin Polymerization" by Cushman, Mark et al. *J. Med. Chem.*, (1991), 34:2579–2588.

Chemical Abstracts, vol. 121, No. 9, 1994.

Database WPI, Section CH, Week 9416, Derwent Publications Ltd., London, GB: AN 94–128759 And JP 6072866A, see English language abstract in Derwent.

"Synthesis and Evaluatinof New Pretein Tyrosine Kinase Inhibitors. Part 1. Pyridine–Containing Stilbenes and Amides" by Cushman, Mark et al. *Bioorganic & Medicinal Chemistry Letters*, (1991) 1/4:211–214.

"Di– and Tri–methoxystyryl Derivatives of Heterocyclic Nitrogen Compounds" by Bahner,C. T. et al. *Arzneim–Forsch,/Drug Res*, (1981)31 (I), Nr. 3.

"Retinobenzoic acids. 3. Structure–Activity Relationships of Retinoidal Azobenzene–4–Carboxylic Acids and Stilbene–4– Carboxylic Acids" by H. Kagechika et al., *Journal of Medicinal Chemistry*, (1989), 32:1098–1108.

\* cited by examiner

METHODS OF TREATMENT WITH COMPOUNDS HAVING RARα RECEPTOR SPECIFIC OR SELECTIVE ACTIVITY

CROSS-REFERENCE TO RELATED APPLICATION

The present application is a divisional of application Ser. No. 08/580,553, filed on Dec. 29, 1995, to be issued as U.S. Pat. No. 5,965,606.

BACKGROUND OF THE INVENTION

1. Field of the Invention

The present invention relates to the use of compounds which have specific or selective agonist like activity on $RAR_\alpha$ retinoid receptors for treatment of diseases and conditions which respond to treatment by such retinoids. More particularly the present invention is directed to the use of $RAR_\alpha$ receptor specific or selective agents for the treatment of tumors.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

U.S. Pat. No. 4,740,519 (Shroot et al.), U.S. Pat. No. 4,826,969 (Maignan et al.), U.S. Pat. No. 4,326,055 (Loeliger et al.), U.S. Pat. No. 5,130,335 (Chandraratna et al.), U.S. Pat. No. 5,037,825 (Klaus et al.), U.S. Pat. No. 5,231,113 (Chandraratna et al.), U.S. Pat. No. 5,324,840 (Chandraratna), U.S. Pat. No. 5,344,959 (Chandraratna), U.S. Pat. No. 5,130,335 (Chandraratna et al.), Published European Patent Application Nos. 0 170 105 (Shudo), 0 176 034 A (Wuest et al.), 0 350 846 A (Klaus et al.), 0 176 032 A (Frickel et al.), 0 176 033 A (Frickel et al.), 0 253 302 A (Klaus et al.), 0 303 915 A (Bryce et al.), UK Patent Application GB 2190378 A (Klaus et al.), German Patent Application Nos. DE 3715955 A1 (Klaus et al.), DE 3602473 A1 (Wuest et al., and the articles J. Amer. Acad. Derm. 15: 756–764 (1986) (Sporn et al.), Chem. Pharm. Bull. 33: 404–407 (1985) (Shudo et al.), J. Med Chem. 1988 31, 2182–2192 (Kagechika et al.), Chemistry and Biology of Synthetic Retinoids CRC Press Inc. 1990 p 334–335, 354 (Dawson et al.), describe or relate to compounds which include a tetrahydronaphthyl moiety and have retinoid-like or related biological activity.

U.S. Pat. Nos. 4,980,369, 5,006,550, 5,015,658, 5,045,551, 5,089,509, 5,134,159, 5,162,546, 5,234,926, 5,248,777, 5,264,578, 5,272,156, 5,278,318, 5,324,744, 5,346,895, 5,346,915, 5,348,972, 5,348,975, 5,380,877, 5,399,561, 5,407,937, (assigned to the same assignee as the present application) and patents and publications cited therein, describe or relate to chroman, thiochroman and 1,2,3,4-tetrahydroquinoline derivatives which have retinoid-like biological activity.

U.S. Pat. No. 4,723,028 (Shudo), Published European Patent Application Nos. 0 170 105 (Shudo), German Patent Application No. DE 3524199 A1 (Shudo), PCT WO 91/16051 (SDada et al.), PCT WO 85/04652 (Polus) and J. Med Chem. 1988 31, 2182–2192 (Kagechika et al.), describe or relate to aryl and heteroaryl or diaryl substituted olephines or amides having retinoid-like or related biological activity.

U.S. Pat. Nos. 4,992,468, 5,013,744, 5,068,252, 5,175,185, 5,202,471, 5,264,456, 5,324,840, 5,326,898, 5,349,105, 5,391,753, 5,414,007 and 5,434,173 (assigned to the same assignee as the present application) and patents and publications cited therein, describe or relate to compounds which have retinoid-like biological activity and a structure wherein a phenyl and a heteroaryl or a phenyl and a second phenyl group is linked with an olephinic or acetylenic linkage. Still further, several co-pending applications and recently issued patents which are assigned to the assignee of the present application, are directed to further compounds having retinoid-like activity.

It is now general knowledge in the art that two main types of retinoid receptors exist in mammals (and other organisms). The two main types or families of receptors are respectively designated RARs and RXRs. Within each type there are subtypes; in the RAR family the subtypes are designated $RAR_\alpha$, $RAR_\beta$ and $RAR_\Gamma$, in RXR the subtypes are: $RXR_\alpha$, $RXB_\beta$ and $RXR_\Gamma$. It has also been established in the art that the distribution of the two main retinoid receptor types, and of the several sub-types is not uniform in the various tissues and organs of mammalian organisms.

It is also known in the art that the use of retinoid-like compounds for the treatment of various diseases and conditions is not without problems or side effects. The side effects at therapeutic dose levels include headache, teratogenesis, mucocutaneous toxicity, musculoskeletal toxicity, dislipidemias, skin irritation, headache, hepatotoxicity, etc. These side effects limit the acceptability and utility of retinoids for treating disease. Research is still ongoing in the art to determine which of the RAR or RXR families and within each family, which of the subtype or subtypes are responsible for mediating certain therapeutic effects, and which type or subtypes are responsible for mediating one or more of the undesired side effects. Accordingly, among compounds capable of binding to retinoid receptors, specificity or selectivity for one of the main types or families, and even specificity or selectivity for one or more subtypes within a family of receptors, is considered a desirable pharmacological property. Such selectivity or specificity is useful as a research tool for discovering the roles of the several receptor types and subtypes in mediating the various effects of retinoids in biological systems, and also as aid for designing retinoid drugs with specific therapeutic effects and/or with reduced side effects and toxicity. Along these lines, U.S. Pat. No. 5,324,840 describes a class of compounds in which retinoid-like activity is accompanied by reduced skin toxicity and reduced teratogenic effects. U.S. Pat. No. 5,399,586 describes the use of compounds having RXR retinoid receptor agonist activity for the treatment of mammals afflicted with tumors. U.S. Pat. No. 5,455,265 describes methods of treatment of mammals with compounds having agonist-like activity on RXR receptors. Published PCT application No. WO93/11755 is also directed to the use of compounds which are selective RXR receptor agonists.

The present invention provides methods of treatment of tumors with compounds which are specific or selective to $RAR_\alpha$ receptors.

SUMMARY OF THE INVENTION

It has been discovered in accordance with the present invention that retinoid-like compounds which act selectively, or preferably even specifically on $RAR_\alpha$ receptor subtypes in preference over $RAR_\beta$ and $RAR_\Gamma$ receptor subtypes, possess desirable pharmaceutical properties associated with retinoids, and are particularly suitable for treatment of tumors, such as acute monocytic leukemia, cervical carcinoma, myeloma, ovarian carcinomas and head and neck carcinomas, without having one or more undesirable side effects of retinoids, such as inducement of weight loss, mucocutaneous toxicity, skin irritation and teratogenecity.

Accordingly, the present invention relates to the use of $RAR_\alpha$ specific or selective retinoid compounds for the treatment of diseases and conditions which respond to treatment by such compounds, and particularly to the treatment of tumors, primarily acute monocytic leukemia, cervical carcinoma, myeloma, ovarian carcinomas and head and neck carcinomas with the $RAR_\alpha$ specific or selective retinoid compounds. In accordance with the present invention the $RAR_\alpha$ selective compounds are also particularly advantageously used for treatment of proliferative vitreoretinopathy (PVR) and age related macular degeneration (AMD).

For the purposes of the present description a compound is considered $RAR_\alpha$ specific or selective if in a transactivation assay (described below) the compound transactivates the $RAR_\alpha$ receptors at a significantly lower concentration than the $RAR_\beta$ and $RAR_\Gamma$ receptors. Instead of measuring transactivation, measuring the binding of a compound respectively to the three RAR receptor subtypes is also feasible. Binding data expressed in Kd numbers obtained in a binding assay (described below) are also indicative of a compound's ability to act specifically or selectively on $RAR_\alpha$ receptors in preference over $RAR_\beta$ and $RAR_\Gamma$ receptors. A compound is considered $RAR_\alpha$ specific or selective for the purposes of the present invention if the Kd number for its binding to $RAR_\alpha$ receptors is approximately 500 times smaller than the Rd for its affinity to $RAR_\beta$ and $RAR_\Gamma$ receptors.

BRIEF DESCRIPTION OF THE DRAWING FIGURES

DETAILED DESCRIPTION OF THE INVENTION

General Embodiments

Figure 1:
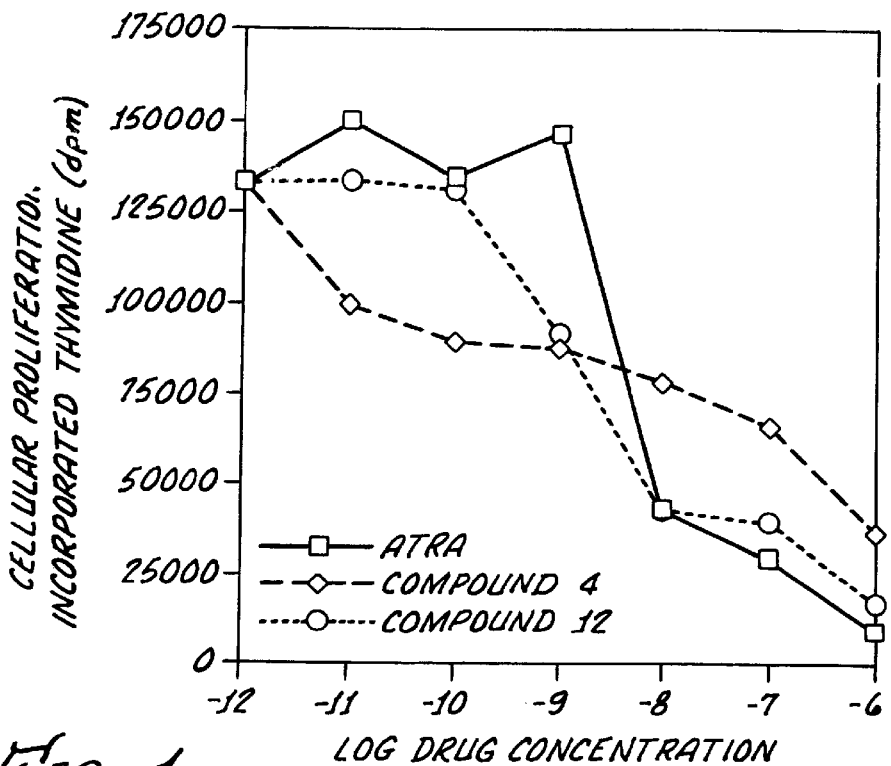
FIG. 1 is a graph showing the results of an RPMI 8226 cell culture assay conducted with all trans retinoic acid (ATRA) and two $RAR_\alpha$ selective compounds in accordance with the present invention.

Definitions Regarding the Chemical Compounds Used in the Present Invention

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B in the general a formula of the preferred compounds used in the invention is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where x is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound used in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may by be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds used in the present invention may have trans and cis (E and Z) isomers. In addition, the compounds used in the present invention may contain one or more chiral centers and therefore may exist in enantiomeric and diastereomeric forms. The scope of the present invention is intended to cover the use of all such isomers per se, as well as mixtures of cis and trans isomers, mixtures of diastereomers and racemic mixtures of enantiomers (optical isomers) as well.

Description of the Compounds Preferably Used in the Methods of the Invention

The retinoid-like compounds used in the methods of treatment of the present invention are specific or selective for RAR$_\alpha$ receptors. That a compound is specific or selective to RAR$_\alpha$ receptors can be ascertained in transactivation assays described below where an RAR$_\alpha$ specific or selective compound transactivates RAR$_\alpha$ receptors at a significantly lower concentrations than RAR$_\beta$ or RAR$_\Gamma$ receptors. In a binding assay where the ability of the compound to bind to these receptor subtypes is measured, a compound that is considered RAR$_\alpha$ specific or selective for the purposes of the present invention binds at least approximately 500 times stronger to RAR$_\alpha$ receptors than to the RAR$_\beta$ or RAR$_\Gamma$ receptors. Alternatively, the compound is considered RAR$_\alpha$ specific or selective if in the binding assay its Kd number is approximately in the $10^{-1}$ to to $5 \times 10^2$ nanomolar range and the Kd number for RAR$_\beta$ or RAR$_\Gamma$ receptors is greater than 1000 nanmolar. The latter is indicated by 0.00 in the below provided Tables where binding data (Kd numbers) for certain exemplary compounds of the present invention are illustrated.

Examples for RAR$_\alpha$ selective compounds which are preferably used in accordance with the present invention are illustrated by Formula 1 and Formula 2

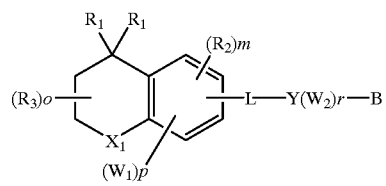

Formula 1

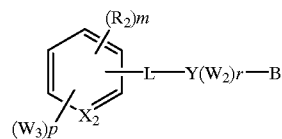

Formula 2 where X$_1$ is O or X$_1$ is [C(R$_1$)$_2$]$_n$ where n is an integer between 0 and 2;

R$_1$ is independently H or alkyl of 1 to 6 carbons;

R$_2$ is independently hydrogen, or lower alkyl of 1 to 6 carbons;

R$_3$ is hydrogen, lower alkyl of 1 to 6 carbons or F;

m is an integer having the value of 0–5;

o is an integer having the value of 0–4;

p is an integer having the value of 0–2;

r is an integer having the value 0–2;

$X_2$ is N or CH;

Y is a phenyl or naphthyl group, or heteroaryl selected from a group consisting of pyridyl, thienyl, cfuryl, pyridazinyl, pyrimidinyl, pyrazinyl, thiazolyl, oxazolyl, imidazolyl and pyrrazolyl, said phenyl, naphthyl and heteroaryl groups being optionally substituted with one or two $R_2$ groups;

$W_1$ is a substituent selected independently from the group consisting of F, Br, Cl, I, fluoro substituted $C_{1-6}$ alkyl, $NO_2$, and OH, with the provisos that:
(i) when the compound is in accordance with Formula 1 and Z is O then the sum of p and r is at least 1 and $W_1$ is not a fluoro group in the 3 position of a tetrahydronaphthalene ring;
(ii) when the compound is in accordance with Formula 1 and r is zero and p is 1 and $W_1$ is OH then the OH group is positioned α to the L group;

$W_2$ is a substituent selected independently from the group consisting of F, Br, Cl, I, fluoro substituted $C_{1-6}$ alkyl, $NO_2$, and OH;

$W_3$ is a substituent selected independently from the group consisting of F, Br, Cl, I, $C_{1-6}$alkyl, fluoro substituted $C_{1-6}$ alkyl, $NO_2$, and OH with the proviso that when the compound is in accordance with Formula 2 and $X_2$ is CH and r is 0 then p is not 0 and at least one $W_3$ group is not alkyl;

L is —(C=Z)—NH— or —NH—(C=Z)Z—

Z is O or S, and

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

With reference to symbol $X_1$ in Formula 1, compounds are preferred in the methods of the present invention where $X_1$ is $[C(R_1)_2]_n$ and n is 1 (tetrahydronaphthalene derivatives) and also where $X_1$ is O (chroman derivatives). With reference to the symbol $X_2$ in Formula 2, compounds are equally preferred where $X_2$ is CH or N. When $X_2$ is CH then the benzene ring is preferably 1, 3, 5 substituted with the L group occupying the 1 position and the $W_3$ and/or $R_2$ groups occupying the 3 and 5 positions. When the symbol $X_2$ is N, then the pyridine ring is preferably 2,4,6 substituted with the L group occupying the 4 position and the $W_3$ and/or $R_2$ groups occupying the 2 and 6 positions.

The $R_1$ groups of Formula 1 are preferably H or $CH_3$. The $R_3$ group of Formula 1 is preferably H. The group B of the preferred compounds of the invention is COOH or a pharamceutically acceptable salt thereof, $COOR_8$ or $CONR_9R_{10}$, where $R_8$, $R_9$ and $R_{10}$ are defined as above.

Referring now to the $W_1$ and $W_2$ groups in Formula 1, these groups are, generally speaking, electron withdrawing groups, which are present in the compounds of the invention either in the aromatic portion of the condensed ring system, or as a substituent of the aryl or heteroaryl group Y. Preferably a $W_2$ group is present in the Y group, and a $W_1$ group is also present in the aromatic portion of the condensed ring system. When the Z group is S (thioamides) a $W_1$ or $W_2$ group does not necessarily have to be present in the compounds of the invention in accordance with Formula 1, although preferably at least one of the $W_1$ or $W_2$ groups is nevertheless present. In the aryl or heteroaryl Y moiety in the compounds of Formula 1 and Formula 2 as well, the $W_2$ group is preferably located in the position adjacent to the B group; preferably the B group is in sara position in the phenyl ring relative to the "amide" moiety, and therefore the $W_2$ group is preferably in meta position relative to the amide moiety. Where there is a $W_1$ group present in the aromatic portion of the condensed ring system of the compounds of Formula 1, it preferably occupies the 8 position of the chroman nucleus with the Z=C—NH— group occupying the 6 position. In tetrahydronaphthalene compounds of Formula 1, the Z=C—NH— group is preferably in the 2-position, and the $W_1$ group is preferably in the 4 position. However, when the $W_1$ group is OH in compounds of Formula 1, then the OH is preferably in the 3 position of the tetrahydronaphthalene ring.

Preferred $W_1$ and $W_2$ groups are F, $NO_2$, Br, I, $CF_3$, $ClN_3$, and OH. The presence of one or two fluoro substituents in the Y group ($W_2$) is especially preferred. When the Y group is phenyl, the fluoro substituents preferably are in the ortho and ortho' positions relative to the B group, which is preferably COOH or $COOR_8$.

Referring now to the $W_3$ group in Formula 2, this group is, generally speaking, also an electron withdrawing group or an alkyl group, more specifically preferred $W_3$ groups are F, $NO_2$, Br, I, $CF_3$, $N_3$, and OH. Alternatively, in the phenyl or pyridyl ring (shown in Formula 2 as substituent "$(W_3)_p$") $W_3$ is an alkyl group, preferably branch-chained alkyl, such as tertiary butyl, and preferably p is 2.

With reference to the symbol Y in Formula 1 and in Formula 2 as well, the preferred compounds used in the methods of the invention are those where Y is phenyl, pyridyl, 2-thiazolyl, thienyl, or furyl, more preferably phenyl. As far as substitutions on the Y (phenyl) and Y (pyridyl) groups are concerned, compounds are preferred where the phenyl group is 1,4 (para) substituted by the L and B groups, and where the pyridine ring is 2,5 substituted by the L and B groups. (Substitution in the 2,5 positions in the "pyridine" nomenclature corresponds to substitution in the 6-position in the "nicotinic acid" nomenclature.) In the preferred compounds of the invention there is no optional $R_1$ substituent (other than H) on the Y group.

The L group of Formula 1 and of Formula 2 is preferably —(C=Z)—NH—, and Z is preferably O. In other words, those carbamoyl or amide compounds are preferred in accordance with the present invention where the —NH— moiety is attached to the Y group.

The compounds which are presently most preferably used in the methods of treatment of the invention are shown below in Table 1 with reference to Formulas 3 and 4 and in Table 2 with reference to Formula 5.

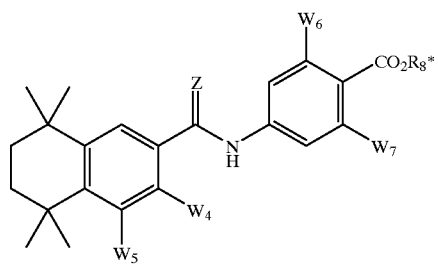

Formula 3

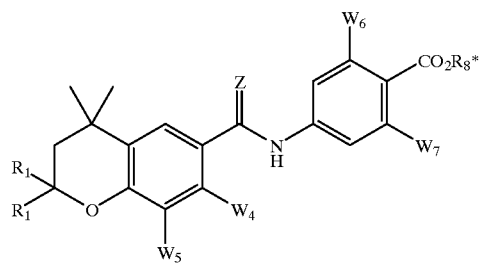

Formula 4

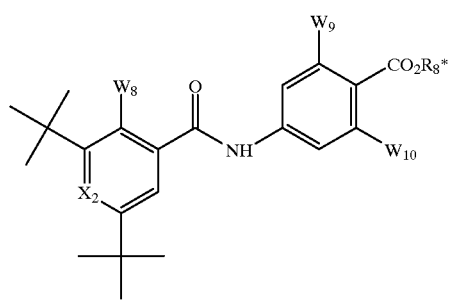

Formula 5

TABLE 1

| Compound No. | Formula | R₁* | W₄ | W₅ | Z | W₆ | W₇ | R8* |
|---|---|---|---|---|---|---|---|---|
| 1 | 3 | — | H | H | O | F | H | Et |
| 2 | 3 | — | H | H | O | F | H | H |
| 3 | 3 | — | H | Br | O | F | H | Et |
| 4 | 3 | — | H | Br | O | F | H | H |
| 5 | 3 | — | OH | H | O | F | H | Et |
| 6 | 3 | — | OH | H | O | F | H | H |
| 7 | 4 | H | H | Br | O | F | H | Et |
| 8 | 4 | H | H | Br | O | F | H | H |
| 9 | 4 | CH₃ | H | Br | O | F | H | Et |
| 10 | 4 | CH₃ | H | Br | O | F | H | H |
| 11 | 4 | CH₃ | H | CF₃ | O | F | H | Et |
| 12 | 4 | CH₃ | H | CF₃ | O | F | H | H |
| 13 | 4 | CH₃ | H | N₃ | O | F | H | Et |
| 14 | 4 | CH₃ | H | N₃ | O | F | H | H |
| 15 | 4 | CH₃ | H | CF₃ | O | F | F | CH₃ |
| 16 | 4 | CH₃ | H | CF₃ | O | F | F | H |
| 17 | 4 | CH₃ | H | I | O | F | H | Et |
| 18 | 4 | CH₃ | H | I | O | F | H | H |
| 19 | 4 | CH₃ | H | CH₃ | O | F | H | Et |
| 20 | 4 | CH₃ | H | CH₃ | O | F | H | H |
| 21 | 3 | — | H | H | S | H | H | Et |
| 22 | 3 | — | H | H | S | H | H | H |
| 23 | 3 | — | H | H | S | F | H | Et |
| 24 | 3 | — | H | H | S | F | H | H |
| 25 | 3 | — | H | Br | O | NO₂ | H | CH₃ |

TABLE 1-continued

| Compound No. | Formula | R₁* | W₄ | W₅ | Z | W₆ | W₇ | R8* |
|---|---|---|---|---|---|---|---|---|
| 26 | 3 | — | H | Br | O | NO₂ | H | H |
| 27 | 4 | CH₃ | H | H | O | F | H | Et |
| 28 | 4 | CH₃ | H | H | O | F | H | H |
| 29 | 3 | — | OH | Br | O | F | H | Et |
| 30 | 3 | — | OH | Br | O | F | H | H |
| 31 | 3 | — | OH | Br | O | F | F | Me |
| 32 | 3 | — | OH | Br | O | F | F | H |
| 33 | 3 | — | H | H | O | F | F | Me |
| 34 | 3 | — | H | H | O | F | F | H |

TABLE 2

| Compound # | X₂ | W₈ | W₉ | W₁₀ | R8* |
|---|---|---|---|---|---|
| 41 | N | H | F | H | Et |
| 42 | N | H | F | H | H |
| 43 | N | H | H | H | Et |
| 44 | N | H | H | H | H |
| 45 | CH | H | F | H | Et |
| 46 | CH | H | F | H | H |
| 47 | CH | OH | F | H | Et |
| 48 | CH | OH | F | H | H |
| 49 | N | H | F | F | Me |
| 50 | N | H | F | F | H |
| 51 | CH | H | F | F | Me |
| 52 | CH | H | F | F | H |
| 53 | N | H | NO₂ | H | Me |
| 54 | N | H | NO₂ | H | H |

Modes of Administration

The RAR$_\alpha$ specific or selective compounds used in the methods of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many disease for which these compounds are useful.

In the treatment of tumors a dose of approximately 0.5 to 5 mg per kg body weight per day is anticipated to constitute the therapeutic dose. Alternatively, as is performed frequently in therapy of malignancies, a patient is provided an initial dose of 1 mg per kg body weight per day, and therafter the dose is raised until a maximum tolerated dose is attained. Assay of $RAR_\alpha$ Receptor Selective Biological Activity and its Significance in Reduced Side Effects and Toxicity As it is noted in the introductory section of this application for patent two main types of retinoic acid receptors (RAR and RXR) exist in mammals (and other organisms). Within each type there are sub-types ($RAR_\alpha$, $RAR_\beta$, $RAR_\Gamma$, $RXR_{60}$, $RXR_\beta$ and $RXR_\Gamma$) the distribution of which is not uniform in the various tissues and organs of mammalian organisms. Selective binding of only one or two retinoid receptor subtypes within one retinoid receptor family can give rise to beneficial pharmacological properties because of the varying distribution of the sub-types in the several mammalian tissues or organs. For the above-summarized reasons, binding of any or all of the retinoid receptors, as well as specific or selective activity in a receptor family, or selective or specific activity in any one of the receptor subtypes, are all considered desirable pharmacological properties.

In light of the foregoing the prior art has developed assay procedures for testing the agonist like activity of compounds in the $RAR_\alpha$, $RAR_\beta$, $RAR_\Gamma$, $RXR_\alpha$, $RXR_\beta$ and $RXR_\Gamma$ receptor subtypes. For example, a chimeric receptor transactivation assay which tests for agonist-like activity in the $RAR_\alpha$, $RAR_\beta$, $RAR_\Gamma$, and $RXR_\alpha$ receptor subtypes, and which is based on work published by Feigner P. L. and Holm M. (1989) Focus, 11 2 is described in detail in U.S. Pat. No. 5,455,265. The specification of U.S. Pat. No. 5,455,265 is expressly incorporated herein by reference.

A holoreceptor transactivation assay and a ligand binding assay which measure the ability of compounds to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A description of the ligand binding assay is also provided below.

Binding Assay

All binding assays were performed in a similar fashion. All six receptor types were derived from the expressed receptor type (RAR $\alpha$, $\beta$, $\Gamma$ and RXR $\alpha$, $\beta$, $\Gamma$) expressed in Baculovirus. Stock solutions of all compounds were prepared as 10 mM ethanol solutions and serial dilutions carried out into 1:1 DMSO; ethanol. Assay buffers consisted of the following for all six receptor assays: 8% glycerol, 120 mM KCl, 8 mM Tris, 5 mM CHAPS 4 mM DTT and 0.24 mM PMSF, pH–7.4 @ room temperature.

All receptor binding assays were performed in the same manner. The final assay volume was 250 $\mu$l and contained from 10–40 $\mu$g of extract protein depending on receptor being assayed along with 5 nM of [$^3$H] all-trans retinoic acid or 10 nM [$^3$H] 9-cis retinoic acid and varying concentrations of competing ligand at concentrations that ranged from 0–10$^{-5}$ M. The assays were formatted for a 96 well minitube system. Incubations were carried out at 4° C. until equilibrium was achieved. Non-specific binding was defined as that binding remaining in the presence of 1000 nM of the appropriate unlabeled retinoic acid isomer. At the end of the incubation period, 50 $\mu$l of 6.25% hydroxyapitite was added in the appropriate wash buffer. The wash buffer consisted of 100 mM KCl, 10 mM Tris and either 5 mM CHAPS (RXR $\alpha$, $\beta$, $\Gamma$) or 0.5% Triton X-100 (RAR $\alpha$, $\beta$, $\Gamma$). The mixture was vortexed and incubated for 10 minutes at 4° C., centrifuged and the supernatant removed. The hydroxyapitite was washed three more times with the appropriate wash buffer. The receptor-ligand complex was adsorbed by the hydroxyapitite. The amount of receptor-ligand complex was determined by liquid scintillation counting of hydroxyapitite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a loglogit plot of the data. The $K_d$ values were determined by application of the Cheng-Prussof equation to the $IC_{50}$ values, the labeled ligand concentration and the $K_d$ of the labeled ligand.

The results of ligand binding assay are expressed in $K_d$ numbers. (See Chena et al. Biochemical Pharmacology Vol. 22 pp 3099–3108, expressly incorporated herein by reference.)

Table 3 shows the results of the ligand binding assay for certain exemplary compounds of the invention.

TABLE 3

Ligand Binding Assay $K_d$ (nanomolar)

| Compound # | RAR$\alpha$ | RAR$\beta$ | RAR$\Gamma$ | RXR$\alpha$ | RXR$\beta$ | RXR$\Gamma$ |
|---|---|---|---|---|---|---|
| 2 | 1.90 | 480.0 | 0.00 | 0.00 | 0.00 | 0.00 |
| 4 | 1.3 | 0.00 | 0.00 | 0.00 | 0.00 | 0.00 |
| 6 | 3.00 | 0.00 | 0.00 | 0.00 | 0.00 | 0.00 |
| 10 | 24.0 | 0.00 | 0.00 | 0.00 | 0.00 | 0.00 |
| 12 | 14.0 | 0.00 | 0.00 | 0.00 | 0.00 | 0.00 |
| 14 | 52.0 | 0.00 | 0.00 | 0.00 | 0.00 | 0.00 |
| 16 | 51.0 | 0.00 | 0.00 | 0.00 | 0.00 | 0.00 |
| 18 | 16.0 | 0.00 | 0.00 | 0.00 | 0.00 | 0.00 |
| 20 | 57.0 | 0.00 | 0.00 | 0.00 | 0.00 | 0.00 |
| 22 | 15 | 0.00 | 0.00 | 0.00 | 0.00 | 0.00 |
| 24 | 7.5 | 0.00 | 0.00 | 0.00 | 0.00 | 0.00 |
| 26 | 245.0 | 0.00 | 0.00 | 0.00 | 0.00 | 0.00 |
| 28 | 162.0 | 0.00 | 0.00 | 0.00 | 0.00 | 0.00 |
| 30 | <3.00 | 0.00 | 0.00 | 0.00 | 0.00 | 0.00 |
| 32 | 2.30 | 0.00 | 0.00 | 0.00 | 0.00 | 0.00 |
| 34 | 9.00 | 0.00 | 0.00 | 0.00 | 0.00 | 0.00 |
| 42 | 14.00 | 0.00 | 0.00 | 0.00 | 0.00 | 0.00 |
| 44 | 19.00 | 0.00 | 0.00 | 0.00 | 0.00 | 0.00 |

TABLE 3-continued

Ligand Binding Assay $K_d$ (nanomolar)

| Compound # | RARα | RARβ | RARΓ | RXRα | RXRβ | RXRΓ |
|---|---|---|---|---|---|---|
| 46 | 26.0 | 0.00 | 0.00 | 0.00 | 0.00 | 0.00 |
| 48 | 77.0 | 0.00 | 0.00 | 0.00 | 0.00 | 0.00 |
| 50 | 62.0 | 0.00 | 0.00 | 0.00 | 0.00 | 0.00 |
| 52 | 87.0 | 0.00 | 0.00 | 0.00 | 0.00 | 0.00 |
| 54 | 94.0 | 0.00 | 0.00 | 0.00 | 0.00 | 0.00 |
| TTNPB[1] | 72 | 5 | 36 | | | |

0.00 indicates value greater than 1000 nM (nanomolar)
[1]TTNPB is a well known prior art retinoid (4-(E)-2-(5,6,7,8-tetrahydro-5,5, 8,8-tetramethylnaphthalen-2-yl)propen-1-yl)benzoic acid, that is not $RAR_\alpha$ selective.

As it can be seen from the foregoing data, the compounds used in accordance with the present invention specifically or selectively bind to $RAR_\alpha$ retinoid receptors. It has been discovered in accordance with the present invention that this unique type of selectivity allows the compounds to retain beneficial retinoid-like properties while reduces certain side effects and toxicity. More specifically, certain in vitro cell culture assays are described below, in which the ability of the $RAR_\alpha$ specific or selective compounds to significantly inhibit the growth of cancer cells is demonstrated.

Cancer Cell Line Assays

Materials and Methods

Hormones

All trans-retinoic acid (t-RA) (Sigma Chemicals Co., St. Louis, Mo.) was stored at −70° C. Prior to each experiment the compound was dissolved in 100% ethanol at 1 mM and diluted in culture medium immediately before use. All experiments were performed in subdued light. Controls were assayed using the same concentration of ethanol as present in the experimental plates and this concentration of diluent had no effect in either assay.

Cells and Cell Culture

The cell lines, RPMI 8226, ME-180 and AML-193 were obtained from the American Type Culture Collection (ATCC, Rockville, Md.). RPMI 8226 is a human hematopoietic cell line obtained from the peripheral blood of a patient with multiple myeloma. The cells resemble the lymphoblastoid cells of other human lymphocyte cell lines and secrete a-type light chains of immunoglobulin. RPMI-8226 cells are grown in RPMI medium (Gibco) supplemented with 10% fetal bovine serum, glutamine and antibiotics. The cells were maintained as suspension cultures grown at 37° C. in a humidified atmosphere of 5% $CO_2$ in air. The cells were diluted to a concentration of $1\times10^5$/ml twice a week.

ME-180 is a human epidermoid carcinoma cell line derived from the cervix. The tumor was a highly invasive squamous cell carcinoma with irregular cell clusters and no significant keratinization. ME-180 cells were grown and maintained in Mccoy's 5 a medium (Gibco) supplemented with 10% fetal bovine serum, glutamine and antibiotics. The cells were maintained as monolayer cultures grown at 37° C. in a humidified atmosphere of 5% $CO_2$ in air. The cells were diluted to a concentration of $1\times10^5$/ml twice a week.

AML-193 was established from the blast cells classified as M5 Acute Monocyte Leukemia. The growth factor, granulocyte colony-stimulation factor (GM-CSF) was required to establish this cell line and growth factors are necessary for its continuous proliferation in chemically defined medium. AML-193 cells were grown and maintained in Iscove's modified Dulbecco's medium supplemented with 10% fetal bovine serum, glutamine and antibiotics with 5 μg/ml insulin (Sigma Chemical Co.) and 2 ng/ml rh GM-CSF (R and D Systems). The cells were diluted to a concentration of $3\times10^5$/ml twice a week.

Incorporation of $^3$H-Thymidine

The method used for determination of the incorporation of radiolabeled thymidine was adapted from the procedure described by Shrivastav et al. RPMI-8226 cells were plated in a 96 well round bottom microtiter plate (Costar) at a density of 1,000 cells/well. To appropriate wells, retinoid test compounds were added at the final concentrations indicated for a final volume of 150 μl/well. The plates were incubated for 96 hours at 37° C. in a humidified atmosphere of 5% $CO_2$ in air. Subsequently, 1 μCi of [5'-$^3$H]-thymidine (Amersham, U.K. 43 Ci/mmol specific activity) in 25 μl culture medium was added to each well and the cells were incubated for an additional 6 hours. The cultures were further processed as described below.

ME-180 wells, harvested by trypsinization were plated in a 96 well flat bottom microtiter plate (Costar) at a density of 2,000 cells/well. The cultures were treated as described above for RPMI 8226 with the following exceptions. After incubation with thymidine the supernatant was carefully removed, and the cells were washed with a 0.5 mM solution of thymidine in phosphate buffered saline. ME180 cells were briefly treated with 50 μl of 2.5% trypsin to dislodge the cells from the plate.

AML-193 cells were plated in a 96 well round bottom microtiter plate (Costar) at a density of 1,000 cells/well. To appropriate wells, retinoid test compounds were added at the final concentrations indicated for a final volume of 150 μl/well. The plates were incubated for 96 hours at 37° C. in a humidified atmosphere of 5% $CO_2$ in air. Subsequently, 1 μCi of [5'-$^3$H]-thymidine (Amersham, U.K., 43 Ci/mmol specific activity) in 25 μl culture medium was added to each well and the cells were incubated for an additional 6 hours.

The cell lines were then processed as follows: the cellular DNA was precipitated with 10% trichloroacetic acid onto glass fiber filter mats using a SKATRON multi-well cell harvester (Skatron Instruments, Sterling Va.). Radioactivity incorporated into DNA, as a direct measurement of cell growth, was measured by liquid scintillation counting. The numbers represent the mean disintegrations per minute of incorporated thymidine from triplicate wells±SEM.

The graph of FIG. 1 of the appended drawings shows that in the above described RPMI 8226 cell (malignant myeloma) culture assay Compounds 4 and 12 (two exemplary compounds used in accordance with this invention) inhibited the growth of these malignant cells, substantially as well as a comparison compound, all trans retinoic acid (ATRA). The graph of FIG. 1 also demonstrates that whereas in a low concentration range ($10^{-12}$ to approximately $10^{-9}$) all trans retinoic acid (ATRA) actually facilitates growth of these cells, the $RAR_\alpha$ selective Compounds 4 and 12 of the present invention do not stimulate but rather already in this low concentrations inhibit the growth of these malignant cells.

Figure 2:
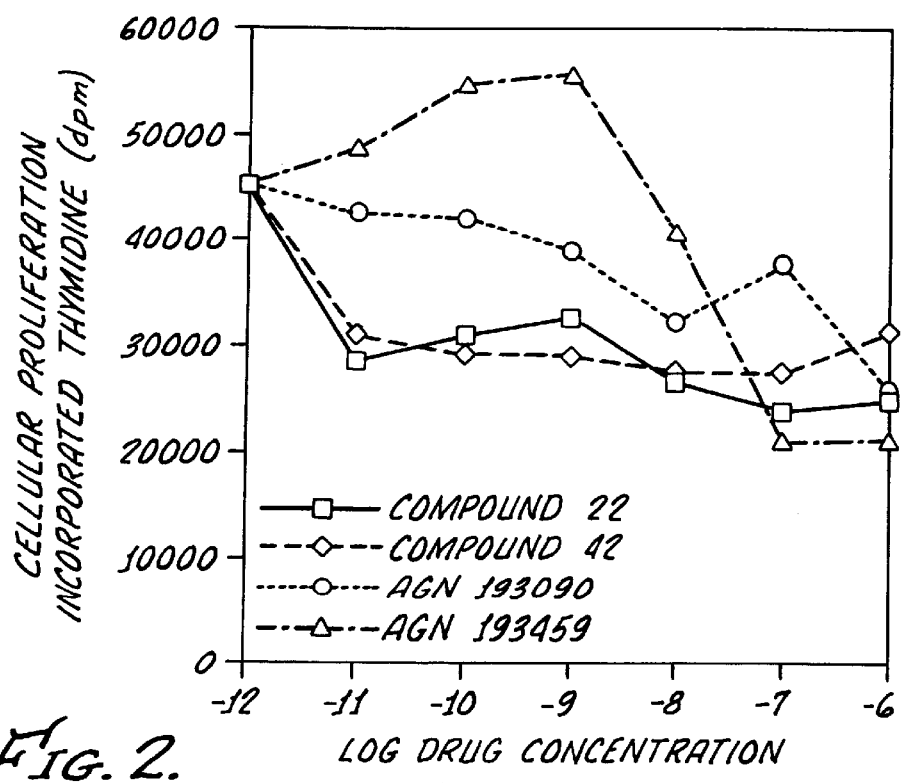
FIG. 2 is another graph showing the results of an AML 193 cell culture assay conducted with two $RAR_\alpha$ selective compounds in accordance with the present invention, and with two compounds which are not $RAR_\alpha$ selective.

The graph of FIG. 2 shows that in the above described AML 193 (acute monocytic leukemia) cell culture assay Compounds 22 and 42 in accordance with this invention inhibited the growth of these malignant cells. Two other compounds for which data are also shown in this graph are designated AGN 193090 and AGN 193459. (An AGN number is an arbitrary designation number used by the corporate assignee of the present invention.) The compounds AGN 193090 and AGN 193459 are not RAR$_\alpha$ selective. These compounds respectively are 4-[(8-cyano-5, 6-dihydro-5,5-dimethylnaphth-2-yl)ethynyl]benzoic acid, and 4-[(5,6-dihydro-5,5-dimethylnaphth-7(6H)-8-(1-2,2-dimethylpropylidene)naphth-2-yl)ethynyl]benzoic acid, and their Kd values for RAR$_\alpha$, RAR$_\beta$ and RAR$_\Gamma$ receptors are 109, 34, 77 and 6, 2, 7, respectively. The graph of FIG. 2 demonstrates that the RAR$_\alpha$ selective or specific compounds inhibit the malignant cell growth at low concentrations where the pan agonist AGN 193090 and AGN 193459 compounds do not inhibit but rather at these low concentrations even stimulate such cell growth.

Figure 3:
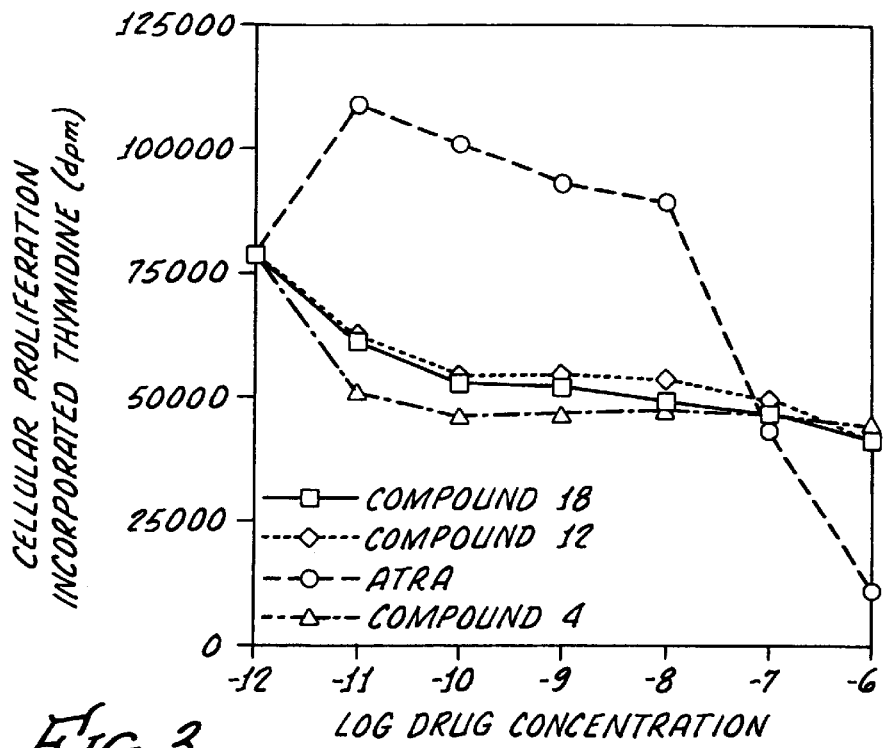
FIG. 3 is still another graph showing results of an AML 193 cell culture assay conducted with three $RAR_\alpha$ selective compounds in accordance with the present invention and with all trans retinoic acid (ATRA).

FIG. 3 is another graph showing the results of an AML-193 cell culture assay, where Compounds 4, 12 and 18 in accordance with the present invention, and all trans retinoic acid (ATRA) were tested. The data show that the RAR$_\alpha$ selective compounds reduce cell proliferation at low concentrations whereas ATRA at the same low concentration actually promotes cell proliferation.

In another line of assays the effect of the retinoid compounds is tested against cells obtained from solid tumors of patients. This EDR assay is described below as follows:

Freshly resected solid tumor biopsies were received within 24 hours of surgery. Species were processed for assay after retaining a portion of the tumor for paraffin embedding and histopathologic confirmation of specimen viability and tissue diagnosis. The remaining specimen was dissociated into small fragments using sterile scissors. The small tissue fragments were then exposed to collagenase and DNAase for 2 hours with mixing a $CO_2$ incubator in order to release the tumor cells from the connective tissue stroma. The resulting cell suspension was washed, and cell counts determined from a cytospin preparation. Tumor cells were resuspended at 40,000 cells per ml in 0.3% agarose in RMPI 1640 supplemented with 15% FCS, glutamine and antibiotics, and 0.5 ml were plated into each well of a 24 well plate over 0.5 ml layer of 0.5% agarose. These culture conditions prevent cell adherence, thereby allowing only transformed cells to proliferate. Additionally, the cells grow into three dimensional spheroids, recapitulating their in vivo morphology.

Retinoid drugs were added 24 hours after plating to insure specimen reequilibration to a growth environment after the rigors of transport and processing. Cells were grown for four days in the presence of drug, with $^3$H-thymidine (5 uCi/ml) added 48 hours prior to harvest to insure adequate labeling of proliferating cells. After the agarose-cell suspension was liquefied at 90° C., cells were harvested onto glass fiber filters, which were counted in 5 ml scintillation fluid using a Beckman 6500 liquid scintillation counter.

Results are reported as fraction of untreated control cell proliferation. Treatment groups were performed in duplicate or triplicate, while the controls were performed in quadruplicate.

Figure 4:
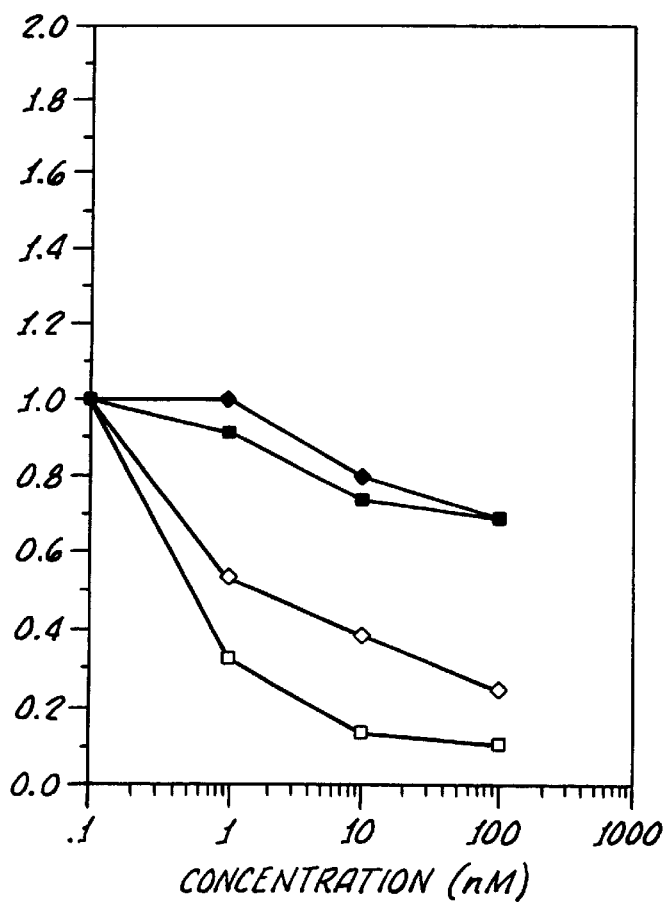
FIG. 4 is a graph showing the proliferation of ovarian tumor cells in a cell culture assay (EDR assay) in the presence of varying concentrations of Compound 2 in accordance with the present invention.

The graph of FIG. 4 shows the effect of compound 2 on ovarian tumors obtained from 4 patients, and demonstrates that the compound inhibits this tumor cell proliferation in a concentration dependent manner.

It will be understood by those skilled in the art, that the ability of the RAR$_\alpha$ selective compounds to significantly inhibit growth of malignant cells in the above described assays is an indication that these compounds can be administered with beneficial effect to tumor bearing mammals (including humans) for the treatment of tumors, particularly acute monocytic leukemia, cervical carcinoma, myeloma, ovarian carcinomas and head and neck carcinomas.

It has also been discovered in accordance with the present invention that the proliferation of retinal pigment epithelium cells is inhibited by RAR$_\alpha$ selective compounds. By way of background it is noted that after retinal detachment the retinal pigment epithelium (RPE) becomes dedifferentiated, proliferates and migrates into the subretinal space (Campochiaro et al., Invest. Opthal & Vis. Sci. 32:65–72 (1991)). Such processes therefore have an impact upon the success of retinal reattachment procedures. RAR agonists such as all-trans-retinoic acid (ATRA) exhibit an antiproliferative effect upon the growth rate of primary human RPE cultures (Campochiaro et al., ibid) and have been shown to decrease the incidence of retinal detachment after retinal reattachment surgery in human studies (Fekrat et al., Opthamology 102:412–418 (1994)).

Figure 5:
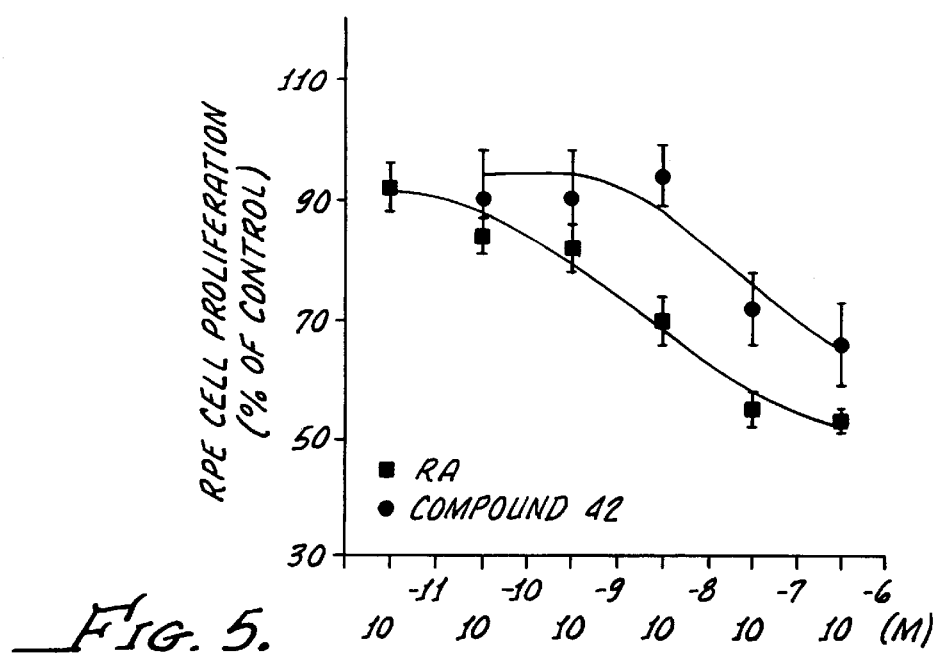
FIG. 5 is a graph showing the RPE cell proliferation in the presence of all trans retinoic acid or Compound 42 in the culture medium.

The graph of FIG. 5 shows the concentration dependent inhibitory effect of all trans retinoic acid (ATRA) and of Compound 42 on RPE proliferation in an assay procedure which is described below.

Analysis of Primary RPE Cultures

Primary cultures of human retinal pigment epithelium (RPE) were established from eyes as previously described, (Campochiaro et al., Invest. Opthal & Vis. Sci. 32:65–72 (1991)). $5 \times 10^4$ Cells were plated in 16-mm wells of 24-well multiwell plates in Dulbecco's modified Eagle's medium (DMEM Gibco) containing 10% fetal bovine serum (FBS). Cells were treated with ethanol alone (control), ATRA ($10^{-10}$ to $10^{-6}$ M) in ethanol, and Compound 42 ($10^{-10}$ to $10^{-6}$ M) in ethanol. Cells were fed with fresh media containing the appropriate concentrations of these compounds every two days for a total of six days treatment. Cells were removed from the plates via treatment with trypsin and the number of cells were counted with an electronic cell counter. As it can be seen in FIG. 5 treatment of primary RPE cells with ATRA and with Compound 42 both led to a dose dependent decrease in RPE cell proliferation.

The effect of topically administering to experimental hairless mice RAR$_\alpha$ selective retinoid compounds in accordance with the present invention was also evaluated in a topical skin irritation assay, using the RAR$_\alpha$ selective Compound 18 of the invention. More particularly, skin irritation was measured on a semi-quantitative scale by the daily subjective evaluation of skin flaking and abrasions. A single number, the topical irritation score, summarizes the skin irritation induced in an animal during the course of an experiment. The topical irritation score is calculated as follows. The topical irritation score is the algebraic sum of a composite flaking score and a composite abrasion score. The composite scores range from 0–9 and 0–8 for flaking and abrasions, respectively, and take into account the maximum severity, the time of onset, and the average severity of the flaking and abrasions observed.

The severity of flaking is scored on a 5-point scale and the severity of abrasions is scored on a 4-point scale, with higher scores reflecting greater severity. The maximum severity component of the composite scores would be the highest daily severity score assigned to a given animal during the course of observation.

For the time of onset component of the composite score, a score ranging from 0 to 4 is assigned as follows:

| Time to Appearance of Flaking of Abrasions of Severity 2 or greater (days) | Time of Onset Score |
|---|---|
| 8 | 0 |
| 6–7 | 1 |
| 5 | 2 |
| 3–4 | 3 |
| 1–2 | 4 |

The average severity component of the composite score is the sum of the daily flaking or abrasion scores divided by the number of observation days. The first day of treatment is not counted, since the drug compound has not had an opportunity to take effect at the time of first treatment.

To calculate the composite flaking and abrasion scores, the average severity and time of onset scores are summed and divided by 2. The result is added to the maximal severity score. The composite flaking and abrasion scores are then summed to give the overall topical irritation score. Each animal receives a topical irritation score, and the values are expressed as the mean ±SD of the individual scores of a group of animals. Values are rounded to the nearest integer.

Thus, female hairless mice [Crl:SKH1-hrBR] (8–12 weeks old, n=4) were treated topically for 5 consecutive days with Compound 18 in doses expresed in nanomol/25 g, which is particularly given in Table 4. Treatments are applied to the dorsal skin in a total volume of 4 ml/kg (~0.1 ml). Mice were observed daily and scored for flaking and abrasions up to and including 3 days after the last treatment, i.e., day 8.

TABLE 4

Eight Day Topical Assay in Hairless Mice of Compound 18

| Dose | Mortality (out of 4) | Body Weight % gain or (loss) | Flaking Score | Abrasion Score | Composite Score |
|---|---|---|---|---|---|
| 100 | 0 | 8 ± 7 | 0 | 1 | 1 ± 1 |
| 1000 | 0 | 4 ± 1 | 1 | 1 | 2 ± 0 |
| of TTNPB | | | | | |
| 0.9 | 0 | 5 ± 2 | 5 | 3 | 8 ± 2 |
| 2.7 | 0 | (4 ± 3) | 6 | 3 | 9 ± 2 |
| 9 | 0 | (11 ± 3) | 7 | 5 | 11 ± 2 |

These data show that the $RAR_\alpha$ selective compound causes virtually no skin irritation and no weight loss up to 1000 nmol/25 g in the test model. For comparison it should be noted that the well known prior art retinoid compound 4-(E)-2-(5,6,7,8-tetrahydro-5,5,8,8-tetramethylnaphthalen-2-yl)propen-1-yl)benzoic acid (TTNPB), which is not $RAR_\alpha$ selective, causes much more serious skin irritation in the above-noted test, as is shown in the foregoing table.

Another important advantage of administering $RAR_\alpha$ selective retinoid compounds to a mammal lies in the significantly reduced teratogenic potency of the $RAR_\alpha$ selective compounds compared to many other retinoids, as measured by a chondrogenesis suppression bioassay. This assay is performed as follows:

High-density "spot" cultures of limb bud mesenchymal cells are used to compare the ability of various concentrations of test drugs to suppress chondrogenic differentiation as a bioassay. Forelimb buds of mouse embryos on day 12 of gestation (54±2 somites) are dissociated in a trypsin-EDTA solution, and the resultant single-cell suspension is plated as 20-μl spots (200,000 cells/spot) on plastic culture dishes. Retinoid concentrations ranging from 0.3 ng/ml to 3 μg/ml (1 nM–10 μM) are added to the culture medium (Eagle's MEM+10% fetal bovine serum, GIBCO) 24 hours after initial plating. Control cultures receive only the vehicle (ethanol, concentration≦1% by vol); Retinoic acid is used as a positive control in another set of cultures.

The cultures are terminated 96 hours after plating, at which time the medium is removed and the cells are fixed for 1 hour in 10% formalin containing 0.5% cetylpyridinium chloride. The cultures are rinsed in acetic acid and stained for 1 hour in 0.5% Alcian blue solution at pH 1.0, differentiated in 3% acetic acid, and then dehydrated in ethanol and scored for chondrogenesis under the microscope. An absence or reduction in the number of cartilage nodules in stained cultures as compared with control cultures is taken as a measure of suppression of chondrogenesis. The number of cartilage nodules stained in the whole spot, mean number of nodules, and standard deviations are calculated for four replicate cultures per treatment. The median concentration causing a 50% inhibition of chondrogenesis compared with controls ($IC_{50}$) is calculated by logarithmic curve fitting of the dose-response data. The $IC_{50}$ values are expressed in nanogram per mililiter (ng/ml) units. An $IC_{50}$ value of greater concentration in this assay signifies lesser teratogenecity. Table 5 indicates the results obtained in this assay for Compounds 10, 18, and 42 in accordance with the present invention, as well as for comparison with all trans retinoic acid (ATRA) and 4-(E)-2-(5,6,7,8-tetrahydro-5,5,8,8-tetramethylnaphthalen-2-yl)propen-1-yl)benzoic acid (TTNPB).

TABLE 5

| Compound | $IC_{50}$ (ng/ml) |
|---|---|
| 10 | 250 |
| 18 | 220 |
| 42 | 65 |
| ATRA | 55 |
| TTNPB | 0.01 |

As it can be seen the compounds used in accordance with the present invention are less teratogenic than all trans retinoic acid and significantly (of the $10^4$ order of magnitude) less teratogenic than the prior art TTNPB compound.

Figure 6:
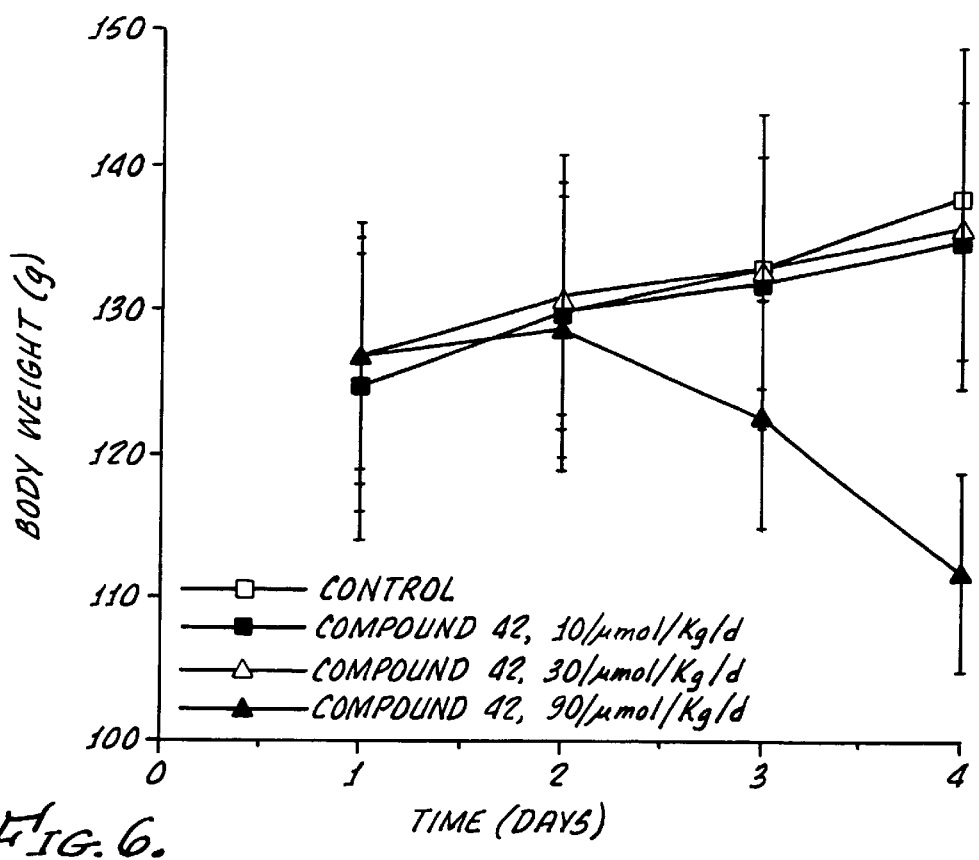
FIG. 6 is a graph showing the weight of a group of experimental rats which were administered for 3 days varying doses of an $RAR_\alpha$ selective compound in accordance with the present invention.
Figure 7:
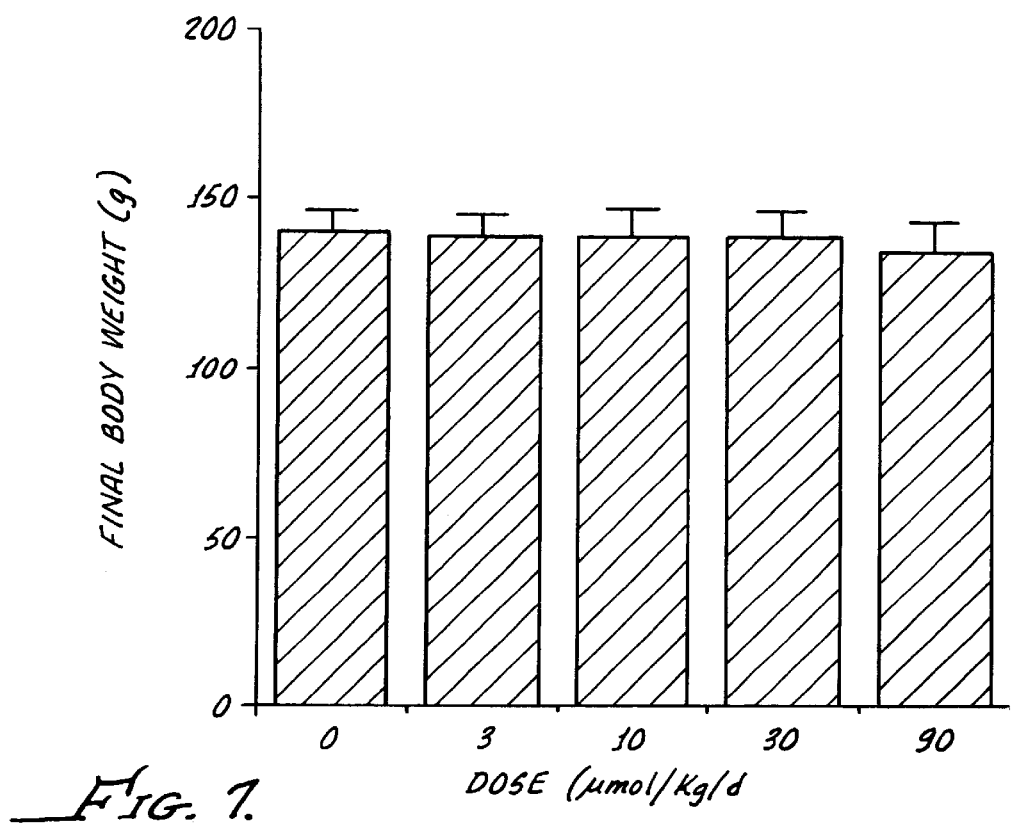
FIG. 7 is a bar graph showing the weight of a group of experimental rats at the end of a 4 day period wherein for three days the rats were administered varying doses of Compound 18 in accordance with the invention.

Weight loss or gain that experimental animals experience upon administration of retinoid compounds is another test of the drug's toxicity, with significant weight loss at relatively low doses indicating a significant toxic side effect of the retinoid. In one experiment, groups of 5 rats were treated with varying doses (administered in corn oil) of a test retinoid for 3 days. The rats were euthanized 24 hours after the last dose. The graph of FIG. 6 shows the average weight of each group of rats treated with a daily dose of 10, 30, and 90 μmol/kg/day of Compound 42, as well as the average weight of a group of control rats which were not given the retinoid. As it can be seen, the $RAR_\alpha$ selective Compound 42 caused virtually no weight loss, as compared to the control, except in a very high dose (90 μmol/kg/day). The graph of FIG. 7 shows the weight of the rats on the fourth day (24 hours after last administration of retinoid) in a similar test with varying doses of Compound 18, with a zero dose indicating the control. As it can be seen, this $RAR_\alpha$ selective retinoid caused virtually no weight loss even in the high dose of 90 μmol/kg/day. It is noteworthy that in similar tests TTNPB, which binds to all three RAR receptor subtypes (see Table 3) causes very significant weight loss. In this experiment involving the rats treated with Compound 42, significant mucocutaneous toxicity was not observed.

Figure 8:
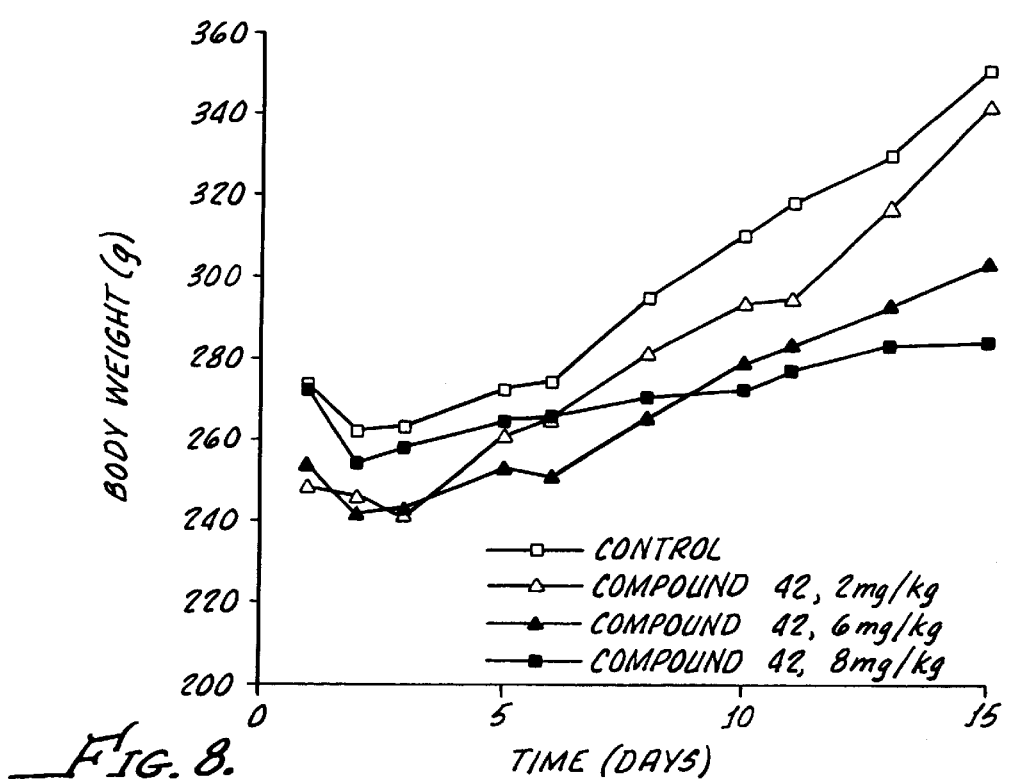
FIG. 8 is a graph showing the weight of guinea pigs which were treated with varying doses of Compound 42 for 15 days.

In another experiment three-week old male Hartley guinea pigs were implanted intraperitonially with osmotic pumps containing 20% DMSO/80 polyethylene glycol (vehicle) or Compound 42 at concentrations of 4.4, 13.3 or 40 mg/ml in vehicle. Based on the initial body weights and known pumping rate, approximate doses of 0, 2, 6, and 18 mg/kg/day doses of Compound 42 are estimated. Body weights and clinical observations were recorded at least every other day for 14 days post-implantation. The guinea pigs were euthanized after 14 days, and the pumps were examined for possible failure. The graph of FIG. 8 shows the weight of the animals involved in this experiment over the course of 15 days. As it can be seen from the graph, the lower and middle doses of the $RAR_\alpha$ selective retinoid compound (Compound 42) caused no, or only statistically insignificant depression of weight gain, relative to the control animals. Significant depression of weight gain was observed only in the high dose (18 mg/kg/day) of Compound 42. Importantly, no signs of mucocutaneous toxicity were observed at any dose of Compound 42 in this experiment. The foregoing, markedly reduced mucocutaneous toxicity observed when animals are treated with $RAR_\alpha$ selective compounds in accordance with the present invention, is a significant advantage, because mucocutaneous toxicity is the major and most irksome retinoid side effect or toxicity in human patients.

Synthetic Methods for Preparing the Preferred Examples of $RAR_\alpha$ Selective Compounds of the Invention General structure of the compounds which are preferably used in the methods of treatment of the present invention are shown above in Formula 1 and Formula 2. These compounds can be made by the synthetic chemical pathways illustrated here. The synthetic chemist will readily appreciate that the conditions set out here are specific embodiments which can be generalized to any and all of the compounds represented by these formulas.

Generally speaking the process of preparing compounds preferably used in the methods of the invention in accordance with Formula 1 involves the formation of an amide by the reaction of a compound of the general Formula 6 with a compound of general Formula 7, or by the reaction of a compound of general Formula 6a with a compound of general Formula 7a. Similarly, the process of preparing compounds in accordance with Formula 2 involves the formation of an amide by the reaction of a compound of the general Formula 8 with a compound of general Formula 7, or by the reaction of a compound of general Formula 8a with a compound of general Formula 7a.

A compound of Formula 6 is an acid or an "activated form" of a carboxylic acid attached to the aromatic portion of a tetrahydronaphthalene, ($X_1=[C(R_1)_2]n$ and n is 1), dihydroindene ($[C(R_1)_2]n$ where n is 0) or chroman ($X_1$ is 0) nucleus. The carboxylic acid, or its "activated form" is attached to the 2 or 3 position of the tetrahydronaphthalene, and to the 6 or 7 position of the chroman moieties. In the compounds preferably used in accordance with the invention the attachment is to the 2 position of tetrahydronaphthalene and to the 6 position of chroman.

The term "activated form" of the carboxylic acid should be understood in this regard as such derivative of the carboxylic acid which is capable of forming an amide when reacted with a primary amine of Formula 7. In case of the "reverse amides" the activated form of a carboxylic acid is a derivative (Formula 7a) that is capable of forming an amide when reacted with a primary amine of Formula 6a. This, generally speaking, means such derivatives of a carboxylic acid which are normally known and used in the art to form amide linkages with an amine. Examples of suitable forms or derivatives for this purpose are acid chlorides, acid bromides, and esters of the carboxylic acid, particularly active esters, where the alcohol moiety of the ester forms a good leaving group. Presently most preferred as reagents in accordance with Formula 6 (or Formula 7a) are acid chlorides ($X_3$ is Cl). The acid chlorides of Formula 6 (or of Formula 7a) can be prepared by traditional methods from the corresponding esters ($X_3$ is for example ethyl) by hydrolysis and treatment with thionyl chloride ($SO_2Cl$). The acid chlorides of Formula 6 (or of Formula 7a) can also be prepared by direct treatment of the carboxylic acids with thionyl chloride, where the carboxylic acid, rather than an ester thereof is available commercially or by a known synthetic procedure. The acid chlorides of Formula 6 (or of Formula 7a) are typically reacted with the amine of Formula 7 (or amine of Formula 6a) in an inert solvent, such as methylene chloride, in the presence of an acid acceptor, such as pyridine.

The carboxylic acids themselves in accordance with Formula 6 (or Formula 7a) are also suitable for amide formation when reacted with an amine, a catalyst (4-dimethylaminopyridine) in the presence of a dehydrating agent, such as dicyclohexylcarbodiimide (DCC) or more preferably 1-(3-dimethylaminopropyl)-3-ethylcarbodiimide hydrochloride (EDC).

The carboxylic acids or the corresponding esters of Formula 6, are generally speaking, prepared as described in the chemical scientific or patent literature and the literature procedures for their preparation may be modified, if necessary, by such chemical reactions or processes which per se are known in the art. For example, generally speaking, 2,2, 4,4 and/or 2,2,4,4-substituted chroman 6-carboxylic acids and chroman 7-carboxylic acids are available in accordance with the teachings of U.S. Pat. Nos. 5,006,550, 5,314,159, 5,324,744, and 5,348,975, the specifications of which are expressly incorporated herein by reference. 5,6,7,8-Tetrahydronaphthalene-2-carboxylic acids are, generally speaking, available in accordance with the teachings of U.S. Pat. No. 5,130,335, the specifications of which is expressly incorporated herein by reference.

The foregoing general description of the reactions which lead to formation of the amides of Formula 1 is also, generally speaking, applicable to the formation of the amides of Formula 2. The reagents which are used in accordance with the general principles mentioned above for the formation of amide compounds of Formua 2 are: activated forms of a carboxylic acids shown in Formula 8 and in Formula 7a, and the amines of Formula 7 and of Formula 8a.

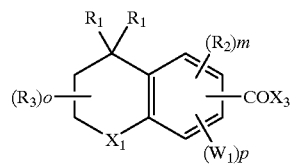

Formula 6

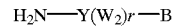

Formula 7

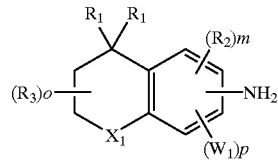

Formula 6a

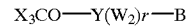

Formula 7a

Formula 8

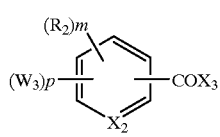

Formula 8a

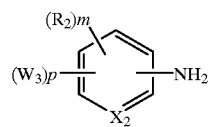

The carboxylic acids or the corresponding esters of Formula 8, are generally speaking, prepared as described in the chemical scientific or patent literature and the literature procedures for their preparation may be modified, if necessary, by such chemical reactions or processes which per se are known in the art.

Reaction Scheme 1

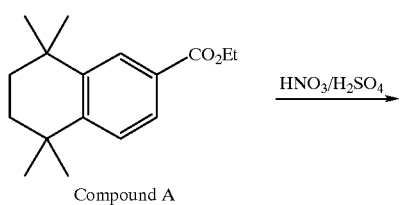
Compound A

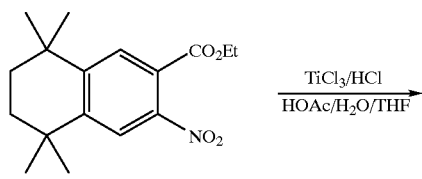
Compound B

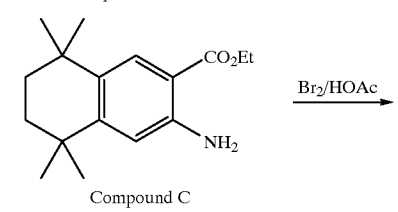
Compound C

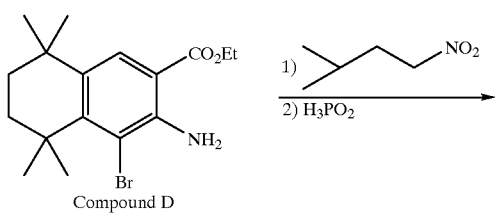
Compound D

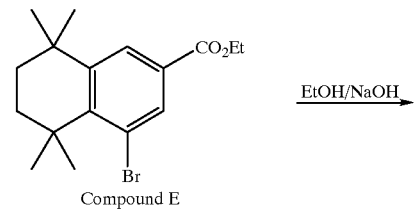
Compound E

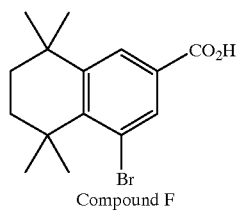
Compound F

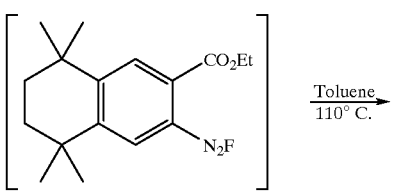
Compound C

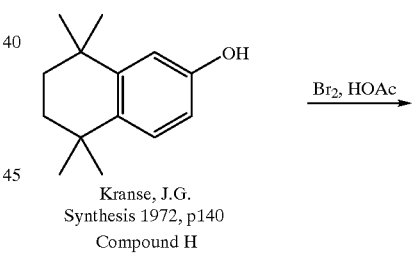

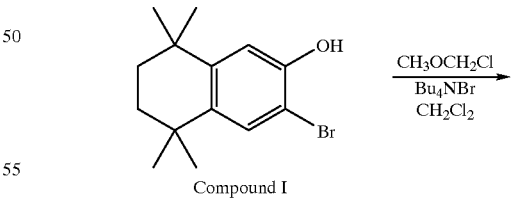
Compound G

Reaction Scheme 2

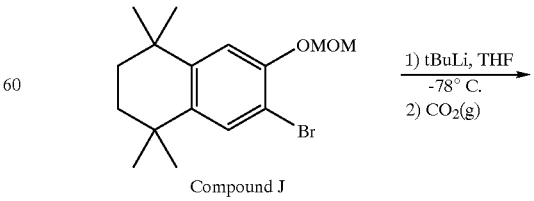
Kranse, J.G.
Synthesis 1972, p140
Compound H

Compound I

Compound J

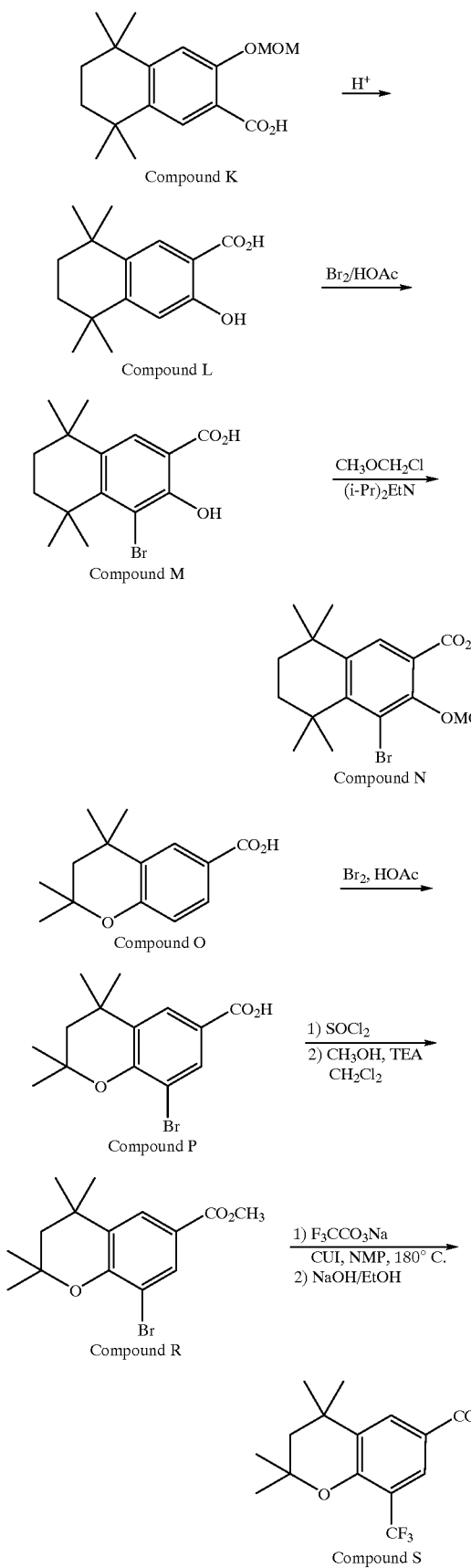
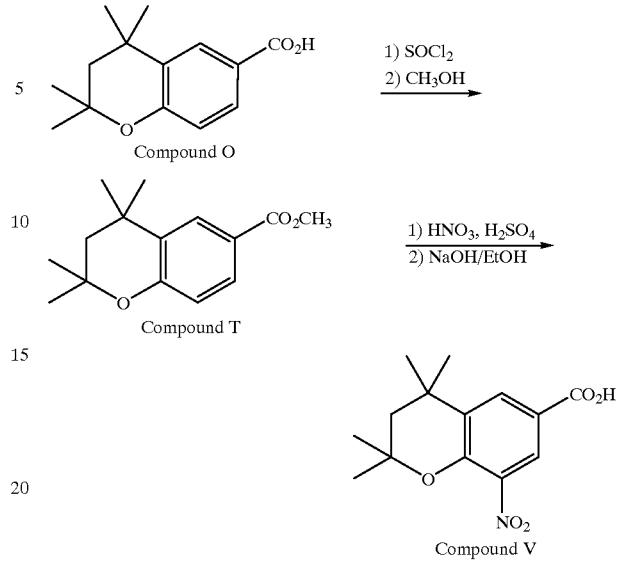

Reaction Schemes 1 and 2 provide examples for the synthesis of derivatives of 5,6,7,8-tetrahydro-5,5,8,8-tetramethyl-naphthalene-2-carboxylic acid, which are within the scope of Formula 6 and which are reacted with an amine of Formula 7 to provide (5,6,7,8-tetrahydro-5,5,8,8-tetramethyl-naphthalene-2-yl)carbamoyl derivatives within the scope of Formula 1. Thus, as is shown in Reaction Scheme 1, ethyl 5,6,7,8-tetrahydro-5,5,8,8-tetramethylnaphthalene-2-carboxylate (Compound A) is nitrated to provide the corresponding 3-nitro compound (Compound B). The nitro group of Compound B is reduced to provide the corresponding 3-amino compound (Compound C) which is described in the publication Lehmann et al. Cancer Research, 1991, 51, 4804. Ethyl 5,6,7,8-tetrahydro-5,5,8,8-tetramethyl-3-aminonaphthalene-2-carboxylate (Compound C) is brominated to yield the corresponding 4-bromo derivative (Compound D), which is converted by treatment with isoamylnitrite and reduction with $H_3PO_2$, to ethyl 5,6,7,8-tetrahydro-5,5,8,8-tetramethyl-4-bromonaphthalene-2-carboxylate (Compound E). Saponification of Compound E yields 5,6,7,8-tetrahydro-5,5,8,8-tetramethyl-4-bromonaphthalene-2-carboxylic acid (Compound F) which is used as a reagent in accordance with Formula 6. Ethyl 5,6,7,8-tetrahydro-5,5,8,8-tetramethyl-3-aminonaphthalene-2-carboxylate (Compound C) is also diazotized and reacted with $HBF_4$ to provide ethyl 5,6,7,8-tetrahydro-5,5,8,8-tetra-methyl-3-fluoronaphthalene-2-carboxylate (Compound G) which serves either per se or after saponification as a reagent in accordance with Formula 6.

5,6,7,8-Tetrahydro-5,5,8,8-tetramethyl-2-hydroxynaphthalene (Compound H, available in accordance with the publication Krause Synthesis 1972 140), is the starting material in the example shown in Reaction Scheme 2. Compound H is brominated to provide the corresponding 3-bromo compound (Compound I) which is thereafter protected in the hydroxyl function by treatment with methoxymethyl chloride (MOMCl) to yield 5,6,7,8-tetrahydro-5,5,8,8-tetramethyl-3-methoxymethoxy-2-bromonaphthalene (Compound J). Compound J is reacted with t-butyllithium and carbon dioxide to provide the corresponding carboxylic acid (Compound K) from which the methoxymethyl protecting group is removed by acid to give 5,6,7,8-tetrahydro-5,5,8,8-tetramethyl-2- hydroxynaphthalene-3-carboxylic acid (Compound L). Compound L is brominated to yield 5,6,7,8-tetrahydro-5,5, 8,8-tetramethyl-1-bromo-2-hydroxynaphthalene-3-carboxylic acid (Compound M). Compound L and Compound M serve as reagents in accordance with Formula 6. The hydroxy group of Compound M is protected for further transformations with methoxymethyl chloride (MOMCl) in the presence of base, yielding 5,6,7,8-tetrahydro-5,5,8,8-tetramethyl-1-bromo-2-methoxymethoxynaphthalene-3-carboxylic acid (Compound N).

Reaction Scheme 3

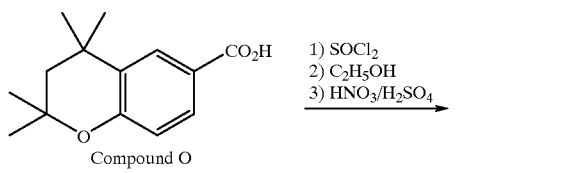

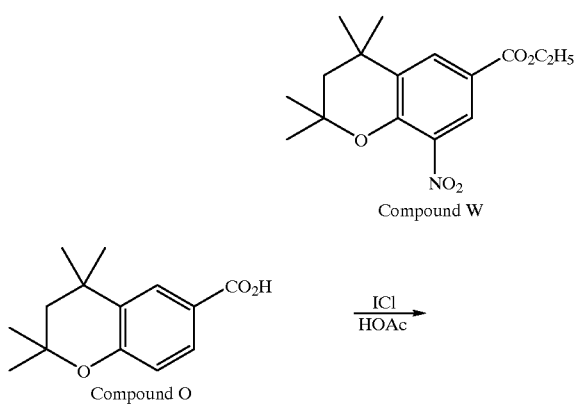

Reaction Scheme 4

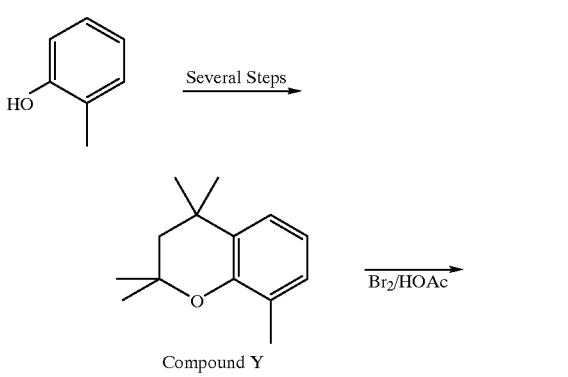

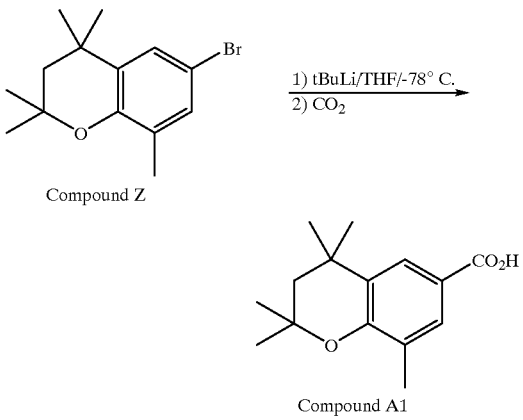

Reaction Scheme 5

Reaction Schemes 3, 4 and 5 provide examples for the synthesis of derivatives of 2,2,4,4 and 4,4-substituted chroman-6-carboxylic acids which can serve as reagents in accordance with Formula 6 for the synthesis of the carbamoyl (amide) compounds within the scope of the present invention. Thus, referring now to Reaction Scheme 3, 2,2, 4,4-tetramethylchroman-6-carboxylic acid (Compound O, see U.S. Pat. No. 5,006,550) is brominated with bromine in acetic acid to yield the corresponding 8-bromo derivative (Compound P). Compound P is converted to the acid chloride by treatment with thionyl chloride, and the resulting acid chloride is suitable for reaction with an amine of Formula 3 to provide the carbamoyl (amide) compounds of the invention. The acid chloride is also reacted with an alcohol (methanol) in the presence of base to yield the corresponding ester, methyl 2,2,4,4-tetramethyl-8-bromochroman-6-carboxylate (Compound R). The bromo function of Compound R is converted to a trifluoromethyl function by treatment with sodium trifluoroacetate in the presence of cuprous iodide catalyst and 1-methyl-2-pyrrolidinone (NMP), and the carboxylate ester group is saponified to yield 2,2,4,4-tetramethyl-8-trifluoromethylchroman-6-carboxylic acid (Compound S). Compound S is within the scope of Formula 6 and is suitable per se or as the acid chloride or in other "activated" form to react with the amines of Formula 7 to yield the carbamoyl (amide) compounds of the invention. 2,2,4,4-

Tetramethylchroman-6-carboxylic acid (Compound O) is also converted to the methyl ester (Compound T) which is then nitrated to yield 2,2,4,4-tetramethyl-8-nitrochroman-6-carboxylic acid (Compound V), still another reagent within the scope of Formula 6. Moreover, in the example further shown in Reaction Scheme 3, 2,2,4,4-tetramethylchroman-6-carboxylic acid (Compound O) is converted to the ethyl ester and nitrated thereafter to yield ethyl 2,2,4,4-tetramethyl-8-nitrochroman-6-carboxylate (Compound W). Still further, Compound O is reacted with ICl to yield 2,2,4,4-tetramethyl8-iodochroman-6-carboxylic acid (Compound X).

In accordance with the example shown in Reaction Scheme 4, 2-methylphenol is subjected to a series of reactions in accordance with the teachings of U.S. Pat. No. 5,045,551 (incorporated herein by reference) to yield 2,2,4,4,8-pentamethylchroman (Compound Y). Compound Y is brominated with bromine in acetic acid to give 2,2,4,4,8-pentamethyl-6-bromochroman (Compound Z) which is reacted with t-butyl lithium and thereafter with carbon dioxide to give 2,2,4,4,8-pentamethylchroman-6-carboxylic acid (Compound $A_1$).

Reaction Scheme 5 illustrates the synthesis of 4,4-dimethyl-8-bromochroman-6-carboxylic acid (Compound $B_1$) by bromination of 4,4,-dimethyl-chroman-6-carboxylic acid which is available in accordance with the teachings of U.S. Pat. No. 5,059,621, the specification of which is incorporated herein by reference. 2,2,4,4,8-Pentamethylchroman-6-carboxylic acid (Compound $A_1$) and 4,4,-dimethyl-8-bromochroman-6-carboxylic acid (Compound $B_1$) serve as reagents, either per se, or as the corresponding acid chlorides (or other "activated form), in accordance with Formula 6 for the synthesis of the carbamoyl (amide) compounds of the present invention.

Referring back now to the reaction between the reagent of Formula 6 with an amine compound of Formula 7 it is noted that the amine compounds are, generally speaking, available in accordance with the state-of-the-art. as described in the scientific and patent literature. More specifically, the amine compounds of Formula 7 can be prepared as described in the scientific and patent literature, or from known compounds of the literature, by such chemical reactions or transformations which are within the skill of the practicing organic chemist. Reaction Scheme 6 illustrates examples for the preparation of amine compounds of Formula 7 (where Y is phenyl) from commercially available starting materials (Aldrich Chemical Company, or Research Plus, Inc.). The illustrated compounds of Formula 7 are used for the synthesis of several preferred compounds used in the methods of the invention.

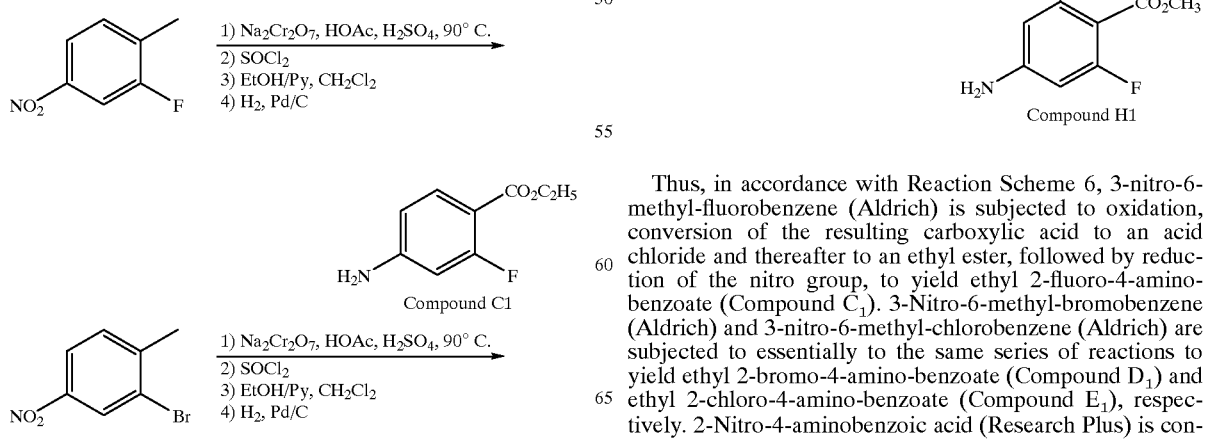

Reaction Scheme 6

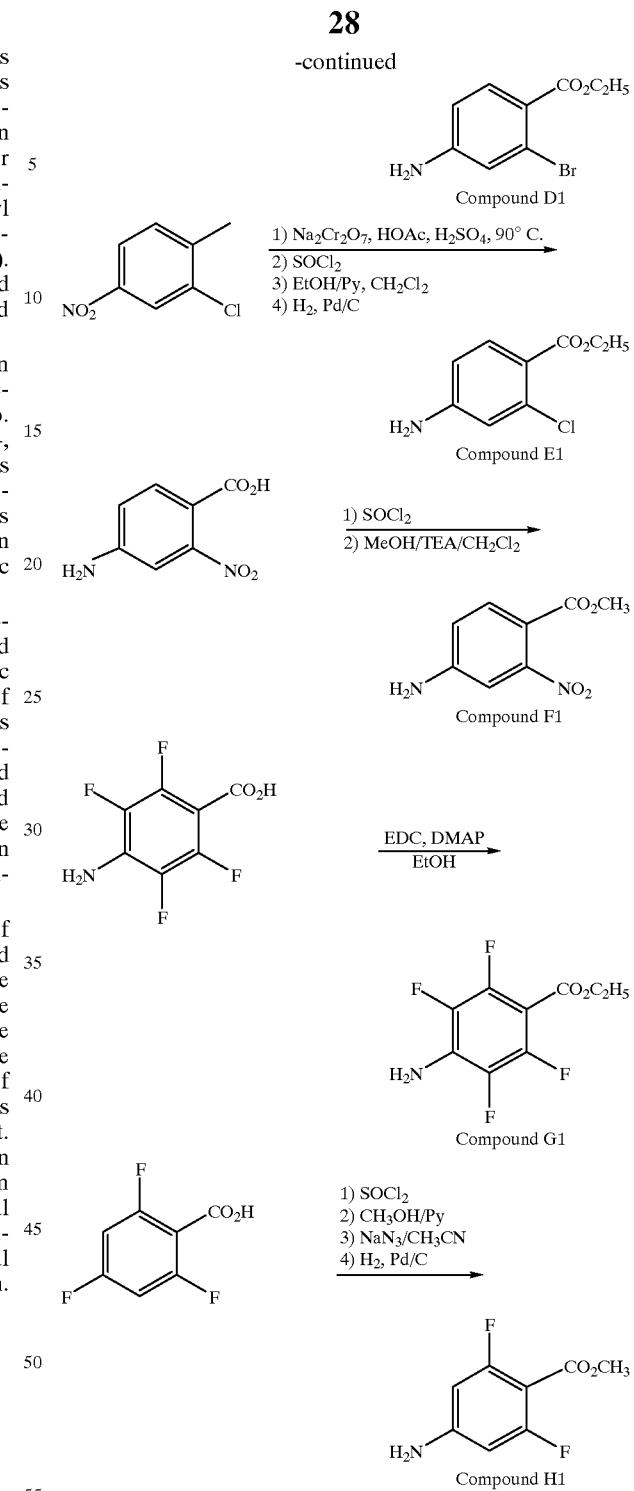

Thus, in accordance with Reaction Scheme 6, 3-nitro-6-methyl-fluorobenzene (Aldrich) is subjected to oxidation, conversion of the resulting carboxylic acid to an acid chloride and thereafter to an ethyl ester, followed by reduction of the nitro group, to yield ethyl 2-fluoro-4-amino-benzoate (Compound $C_1$). 3-Nitro-6-methyl-bromobenzene (Aldrich) and 3-nitro-6-methyl-chlorobenzene (Aldrich) are subjected to essentially to the same series of reactions to yield ethyl 2-bromo-4-amino-benzoate (Compound $D_1$) and ethyl 2-chloro-4-amino-benzoate (Compound $E_1$), respectively. 2-Nitro-4-aminobenzoic acid (Research Plus) is converted to its methyl ester (Compound $F_1$) through the corresponding acid chloride. 2,3,5,6-Tetrafluoro-4-aminobenzoic acid (Aldrich) is esterified by treatment with ethanol in the presence of 1-(3-dimethylaminopropyl)-3-ethylcarbodiimide hydrochloride (EDC) and 4-dimethylaminopyridine in $CH_2Cl_2$ to give ethyl 2,3,5,6-tetrafluoro-4-amino-benzoate (Compound $G_1$). 2,4,6-Trifluorobenzoic acid (Aldrich) is converted to the methyl ester through the acid chloride, and the 4-fluoro atom is displaced by reaction with sodium azide, followed by hydrogenation, to yield methyl 2,6-difluoro-4-amino benzoate (Compound $H_1$) Compounds $C_1$, $D_1$, $E_1$, $F_1$, $G_1$ and $H_1$ serve as amine reagents in accordance with Formula 7. Further examples of reagents in accordance with Formula 7 are nitro, fluoro, chloro, bromo and trifluoromethyl derivatives of amino substituted heteroaryl carboxylic acids, or their lower alkyl esters, such as ethyl 2-amino-4-chloropyridine 2-carboxylate, ethyl 5-amino-3-chloropyridine 5-carboxylate, and 3,4-dibromo-5-aminothiophene-2-carboxylic acid. The latter examples can be prepared by respective chlorination or bromination of 2-aminopyridine-5-carboxylic acid or of its ester, 2-aminopyridine-5-carboxylic acid, 3-aminopyridine-6-carboxylic acid or of its ester (described in WO 93/06086) and of 2-aminothiophene-5-carboxylic acid (described in PCT/US92/06485).

The reactions between the compounds of Formula 6 and Formula 7 or between compounds of Formula 6a and 7a, described above, comprise the actual syntheses of the carbamoyl (amide) compounds of the invention. Numerous examples of this reaction are described in detail in the experimental section below. The carbamoyl (amide) compounds of the invention can be converted into thiocarbamoyl (thioamide) compounds of the invention where with reference to Formula 1 Z is S, by reacting the carbamoyl (amide) compound with 2,4-bis(4-methoxyphenyl)-1,3-dithia-2,4-diphosphetane-2,4-disulfide (Lawesson's reagent). This reaction is illustrated in Reaction Scheme 7 for two specific examples for the compounds used in the methods of the invention.

In Reaction Scheme 7 one starting material ethyl 4-[5',6',7',8'-tetrahydro-5',5',8',8'-tetramethylnaphthalen-2-yl)carbamoyl]benzoate (Compound $I_1$) is obtained in accordance with the teachings of Kaaechika et al. J. Med Chem. 1988 31, 2182–2192. The other starting material, ethyl 2-fluoro-4-[5',6',7',8'-tetrahydro-5',5',8',8'-tetramethylnaphthalen-2-yl)carbamoyl]benzoate (Compound 1) is obtained in accordance with the present invention.

Reaction Scheme 7

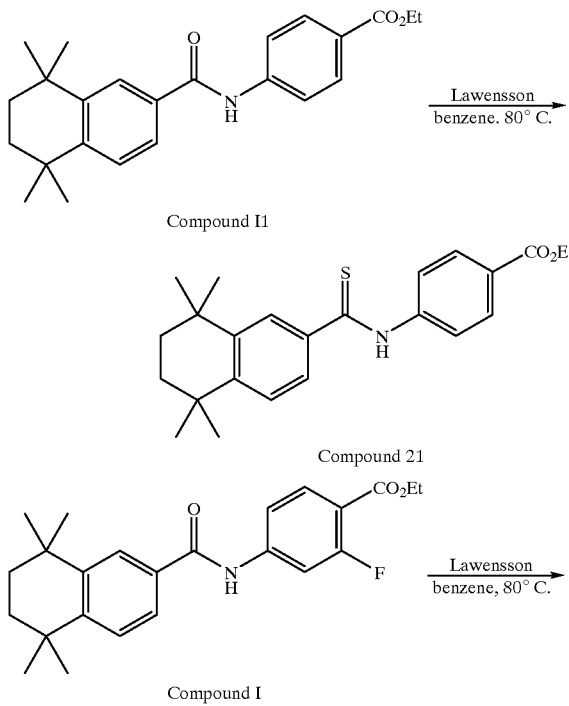

Reaction Scheme 8

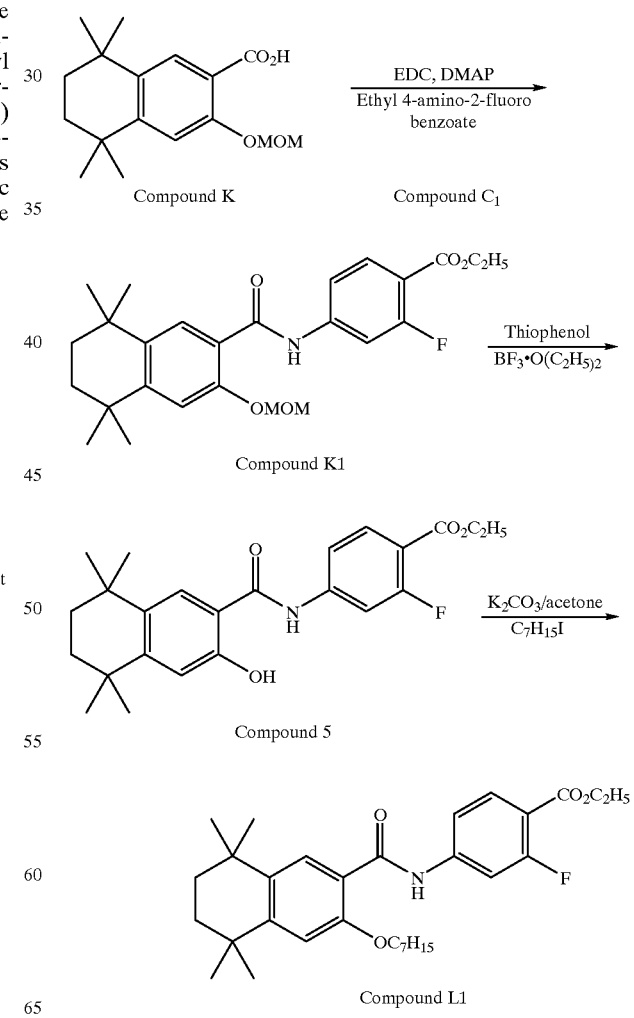

Reaction Scheme 9

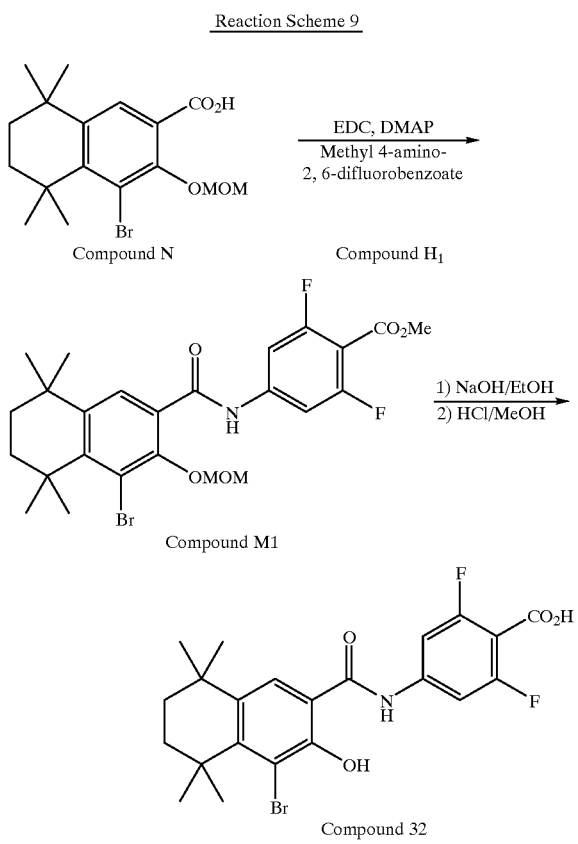

Compound N

Compound $H_1$

Compound M1

Compound 32

Reaction Scheme 10

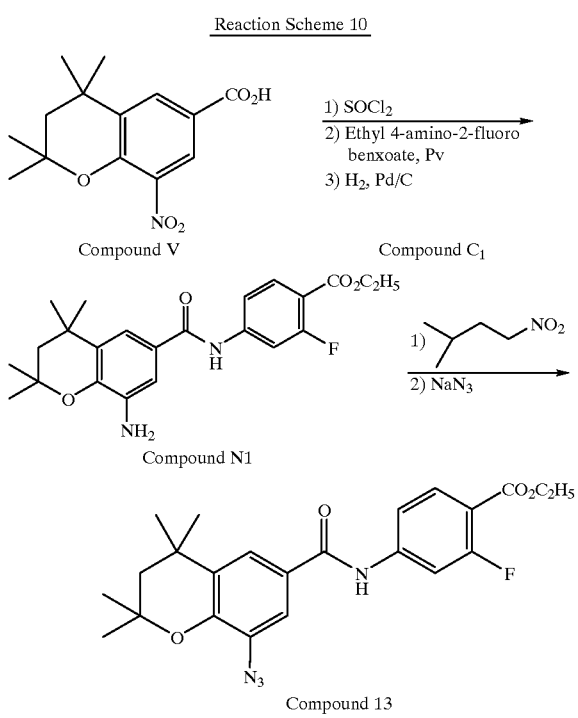

Compound V

Compound $C_1$

Compound N1

Compound 13

Reaction Schemes 8, 9 and 10 disclose examples for the preparation of carbamoyl (amide) compounds of the invention, first by a coupling reaction of a compound of Formula 6 with a compound of Formula 7, followed by one or more reactions performed on the carbamoyl (amide) compound that has been first obtained directly in the coupling reaction. Thus, as is shown in Reaction Scheme 8, 5,6,7,8-tetrahydro-5,5,8,8-tetramethyl-3-methoxymethoxynaphthalene-2-carboxylic acid (Compound K) is coupled with ethyl 4-amino-2-fluorobenzoate (Compound $C_1$) in $CH_2Cl_2$ in the presence of 1-(3-dimethylaminopropyl)-3-ethylcarbodiimide hydrochloride (EDC) and dimethylaminopyridine (DMAP) to give ethyl 2-fluoro-4-[5',6',7',8'-tetrahydro-5',5',8',8'-tetramethyl-2'-methoxymethoxy-naphthalen 3'-yl)carbamoyl)benzoate (Compound $K_1$). The methoxymethyl protecting group is removed from Compound $K_1$ by treatment with thiophenol and borontrifluoride ethereate resulting in ethyl 2-fluoro-4-[5',6',7',8'-tetrahydro-5',5',8',8'-tetramethyl-2'-hydroxynaphthalen-3'-yl)carbamoyl]-benzoate (Compound 5). The hydroxy function of Compound 5 is converted into an n-hexyl ether by treatment with hexyl iodide in the presence of mild base.

In accordance with Reaction Scheme 9 5,6,7,8-tetrahydro-5,5,8,8-tetramethyl-1-bromo-2-methoxymethoxynaphthalene-3-carboxylic acid (Compound N) is coupled with methyl 4-amino-2,6-difluorobenzoate (Compound $H_1$) in $CH_2Cl_2$ solvent in the presence of ethylcarbodiimide hydrochloride (EDC) and DMAP to provide methyl 2,6-difluoro-4-[(5',6',7',8'-tetrahydro-5',5',8',8'-tetramethyl-1'-bromo-2'-methoxymethoxynaphthalen-3'-yl)carbamoyl]benzoate (Compound $M_1$), from which the esterifying methyl group and the methoxymethyl protecting group are removed by treatment with base and acid, respectively to yield 2,6-difluoro-4-[(5',6',7',8'-tetrahydro-5',5',8',8'-tetramethyl-1'-bromo-2'-hydroxy-naphthalen-3'-yl)carbamoyl]benzoic acid (Compound 32).

Reaction Scheme 10 discloses the example of converting 2,2,4,4-tetramethyl-8-nitrochroman-6-carboxylic acid (Compound V) into the corresponding acid chloride by treatment with thionyl chloride, followed by coupling with ethyl 4-amino-2-fluorobenzoate (Compound $C_1$) and hydrogenation to yield ethyl 2-fluoro-4-[(2',2',4',4'-tetramethyl-8'-amino-6'-chromanyl)carbamoyl]benzoate (Compound $N_1$). Compound $N_1$ is converted to the corresponding 8-azido compound, ethyl 2-fluoro-4-[(2',2',4',4'-tetramethyl-8'-azido-6'-chromanyl)carbamoyl]benzoate (Compound 13) by treatment with isoamyl nitrate and $NaN_3$.

Reaction Scheme 11

Formula 6

Formula 9

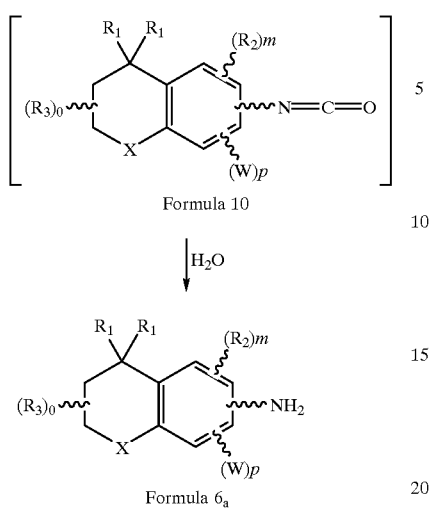

Formula 10

↓ H₂O

Formula 6ₐ

Reaction Scheme 11 illustrates the synthesis of the primary amine compounds of Formula 6a from the acid chlorides ($X_3=Cl$) or other form of activated acids of Formula 6 where the primary amine of Formula 6a is not available by a published literature procedure. Thus, substantially in accordance with the step of a Curtius rearrangement, the acid chloride of Formula 6 is reacted with sodium azide in acetone to yield the azide compound of Formula 9. The azide of Formula 9 is heated in a polar high boiling solvent, such as t-butanol, to provide the intermediate isocyanate of Formula 10, which is hydrolyzed to yield a compound of Formula 6a.

Reaction Scheme 12

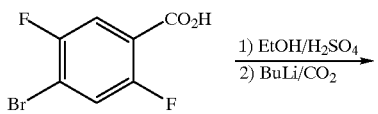

1) EtOH/H₂SO₄
2) BuLi/CO₂

Sugawara, S; Ishikawa, N.
Kogyo Kaguku Zasshi
1970, 73, 972–979

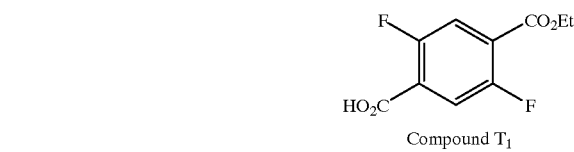

Compound T₁

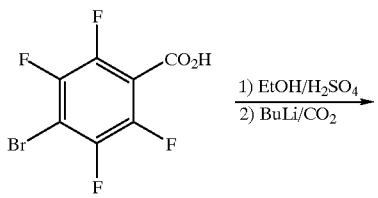

1) EtOH/H₂SO₄
2) BuLi/CO₂

Michael Reuman et al
J. Med. Chem.
1995, 38, 2531–2540

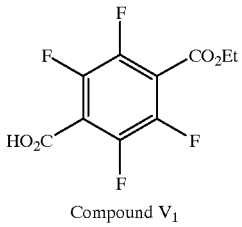

Compound V₁

Reaction Scheme 12 illustrates examples for preparing compounds of Formula 7a where such compounds are not available commercially or by a published literature procedure. Thus, by way of example 2,5-difluoro-4-bromobenzoic acid (available by the literature procedure of Sugawara et al. Kogyo Kaguku Zasshi 1270, 73, 972–979) is first esterified by treatment with ethyl alcohol and acid to yield the corresponding ester, and thereafter is reacted with butyl lithium followed by carbon dioxide to give the monoester of 2,5-difluoro terephthalic acid (Compound T₁). A similar sequence of reactions performed on 2,3,5,6-difluoro-4-bromobenzoic acid (available by the literature procedure of Reuman et al. J. Med. Chem. 1995, 38, 2531–2540) yields the monoester of 2,3,5,6-tetrafluoroterephthalic acid (Compound V₁). The just illustrated sequence of reaction can be, generally speaking, utilized for the synthesis of all compounds of Formula 7a with such modification which will become readily apparent to those skilled in the art, where such compounds are not available by a known literature procedure.

Reaction Scheme 13 provides an example for the preparation of 2,6-di-tert-butylisonicotinic acid (Compound C₃) which is a reagent in accordance with Formula 8 for the preparation of several preferred compounds of the present invention. Thus, 2,6-di-tert-butyl-4-methylpyridine (available commercially from Aldrich Chemical Co.) is reacted with N-bromosuccinimide and benzoyl peroxide to provide 4-bromomethyl-2,6-di-tert-butylpyridine (Compound A₃). Compound A₃ is reacted with base (sodium hydroxyde) to yield the coresponding hydroxymethyl compound (Compound B₃), which is thereafter oxidized in a Jones oxidation reaction to give 2,6-di-tert-butylisonicotinic acid (Compound C₃).

Reaction Scheme 13

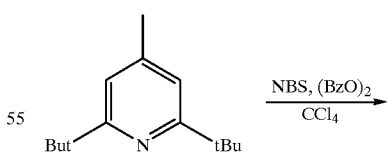

NBS, (BzO)₂
CCl₄

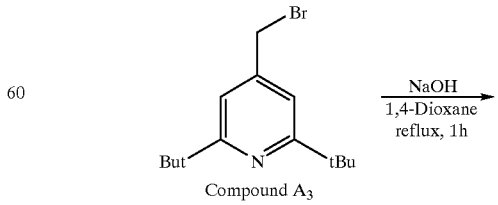

NaOH
1,4-Dioxane
reflux, 1h

Compound A₃

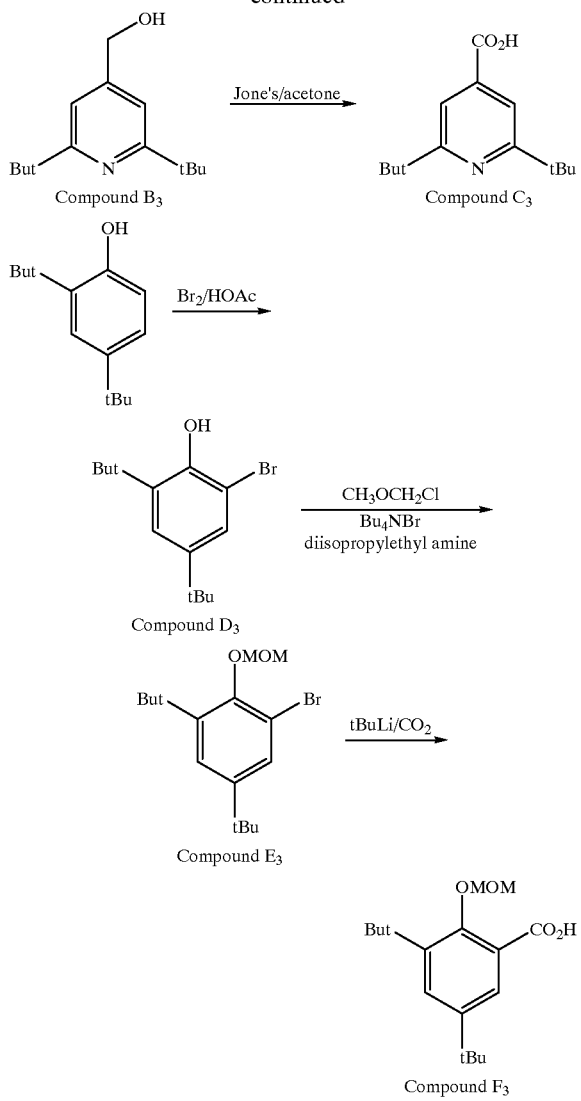

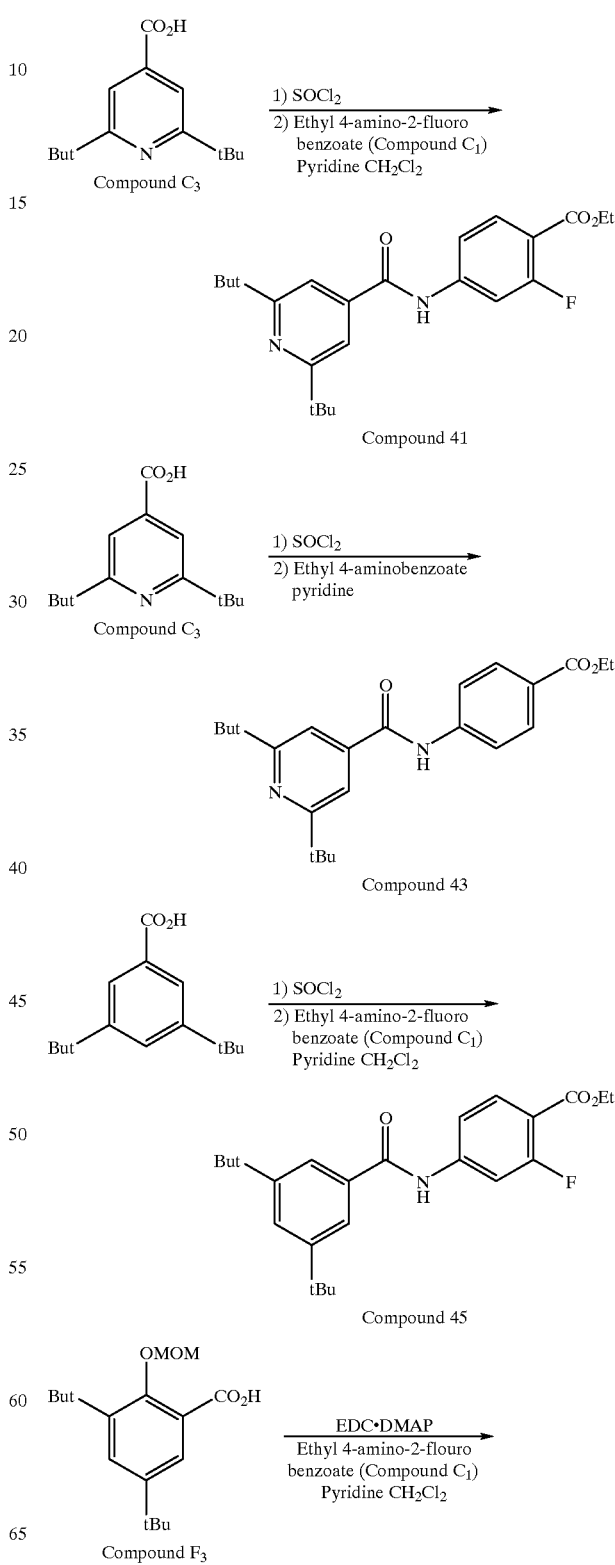

other form of activated acids of Formula 8 substantially in accordance with the steps of a Curtius rearrangement, in analogy to the reaction steps described above in connection with Reaction Scheme 11.

A further example of a compound which serves as a reagent for preparing the carbamoyl (or amide) compounds of the present invention is provided in Reaction Scheme 13. 2,4-Di-tert-butylphenol (Aldrich) is brominated in glacial acetic acid to yield 2-bromo-4,6-di-tert-butylphenol (Compound $D_3$) which is thereafter reacted with methoxymethyl chloride (MOMCl) to give O-methoxymethyl-2-bromo-4,6-di-tert-butylphenol (Compound $E_3$). Compound $E_3$ is treated with t-butyl lithium followed by carbon dioxide to yield O-methoxymethyl-3,5-di-tert-butylsalicylic acid (Compound $F_3$). Compound $P_3$ is a reagent which differs from the compounds generally encompassed by Formula 8 only in that the hydroxyl funtion of this compound is protected by the methoxymethyl (MOM) group. However, the methoxymethyl protecting group is removed after formation of the carbamoyl (amide) linkage, as exemplified in Reaction Scheme 14. Reaction of an aromatic bromo compound (such as Compound $D_3$) with t-butyl lithium followed by carbon dioxide is a preferred method for preparing several aromatic carboxylic acids in accordance with Formula 8 and Formula 7a, described in the present application.

The primary amine compounds of Formula Sa which are not available commercially or by a published literature procedure can be made from the acid chlorides ($X_3$=Cl) or

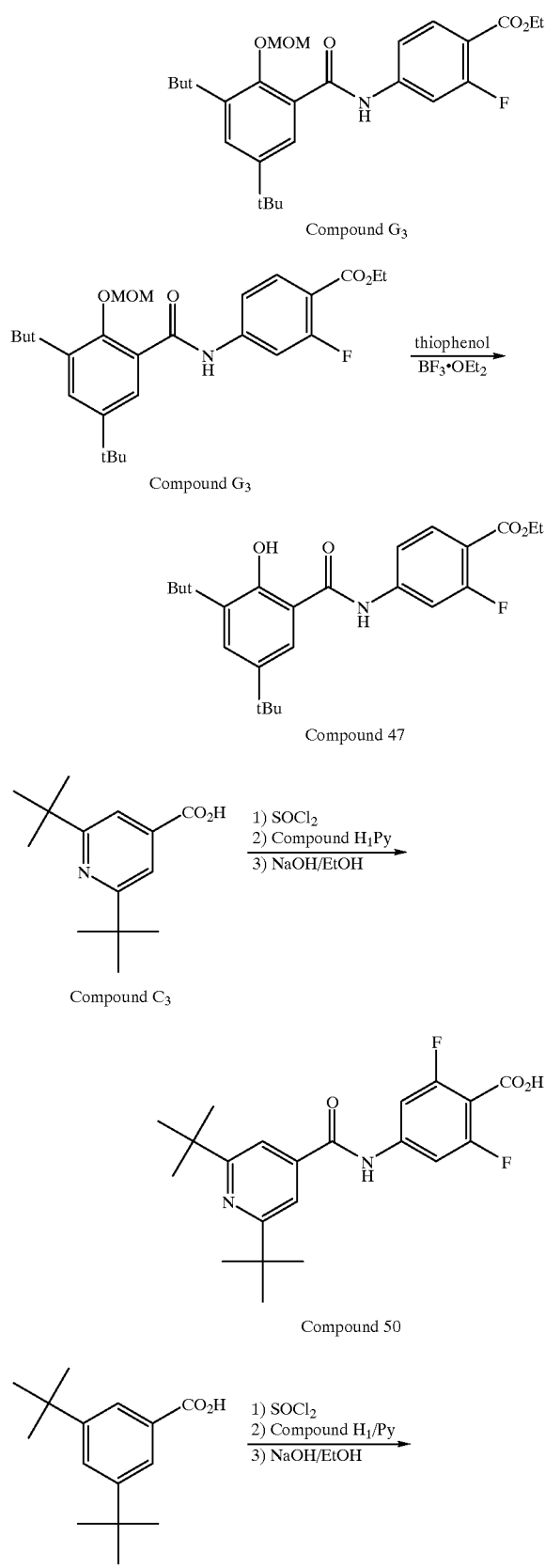

Reaction Scheme 14 illustrates examples for the formation of the carbamoyl (amide) compounds in accordance with Formula 2, by reaction of a reagent of Formula 8 with a reagent of Formula 7. Thus, 2,6-di-tert-butylisonicotinic acid (Compound $C_3$) is reacted with thionyl chloride ($SOCl_2$) to provide the intermediate acid chloride, which is then reacted with ethyl 2-fluoro-4-amino-benzoate (Compound $C_1$) in the presence of an acid acceptor (pyridine) to yield ethyl 2-fluoro-4-[(2'6'-di-tert-butylpyrid-4'-yl)carbamoyl]benzoate (Compound 41). As another example, 3,5-di-tert-butylbenzoic acid (available by the literature procedure of Kagechika et al., J. Med. Chem. 1988, 31, 2182, incorporated herein by reference) is reacted with thionyl chloride, followed by ethyl 2-fluoro-4-amino-benzoate (Compound $C_1$) to yield ethyl 2-fluoro-4-[(3',5'-di-tert-butylphenyl)carbamoyl]benzoate (Compound 45). As still another example, O-methoxymethyl-3,5-di-tert-butylsalicylic acid (Compound $F_3$) is reacted with ethyl 2-fluoro-4-amino-benzoate (Compound $C_1$) in the presence of 4-dimethylaminopyridine (DMAP) catalyst and 1-(3-dimethylaminopropyl)-3-ethylcarbodiimide hydrochloride (EDC) to give ethyl 2-fluoro-4-[(2'-methoxymethyl-3',5'-di-tert-butylphenyl)carbamoyl]benzoate (Compound $G_3$). The methoxymethyl protecting group is removed from Compound $G_3$ by treatment with borontrifluoride ethereate and thiophenol to yield ethyl 2-fluoro-4-[(2'-hydroxy-3',5'-di-tert-butylphenyl)carbamoyl]benzoate (Compound 47).

In yet another example shown in Reaction Scheme 14, 2,6-di-tert-butylisonicotinic acid (Compound $C_3$) is reacted with thionyl chloride ($SOCl_2$), the resulting intermediate acid chloride is reacted with methyl 2,6-difluoro-4-amino benzoate (Compound $E_1$), followed by saponification of the ester group, to yield 2,6-difluoro-4-[(2',6'-di-tert-butylpyrid-4'yl)carbamoyl]benzoic acid (Compound 50). 3,5-Di-tert-butylbenzoic acid is subjected to the same sequence of reactions to provide 2,6-difluoro-4-[(3',5'-di-tert-butylphenyl)carbamoyl]benzoic acid (Compound 52).

As yet another example, shown in Reaction Scheme 14, 2,6-di-tert-butylisonicotinic acid (Compound $C_3$) is reacted with thionyl chloride ($SOCl_2$), followed by methyl 2-nitro-4-aminobenzoate (Compound $F_1$) and saponification of the ester function to give 2-nitro-4-[(2',6'-di-tert-butylpyrid-4'-yl)carbamoyl]benzoic acid (Compound 54).

Numerous other reactions suitable for preparing compounds of the invention, and for converting compounds of Formula 1 and/or of Formula 2 into still further compounds which can be used in the methods of treatment of the present invention, and also for preparing the reagents of Formula 6, Formula 7, Formula 8, Formula 6a, Formula 7a and Formula 8a will become readily apparent to those skilled in the art in light of the present disclosure. In this regard the following general synthetic methodology, applicable for conversion of the compounds of Formula 1 and/or of Formula 2 into further homologs and/or derivatives, and also for preparing the reagents of Formula 6, Formula 7, and 8, (as well as 6a, 7a and 8a) is noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2 nd Edition, McGraw-Hill Book Company, p 810). Alcohols, aldehydes and ketones all may be protected by forming respectively, ethers and esters, acetals or ketals by known methods such as those mdescribed in McOmie, Plenum Publishing Press, 1973 and Protecting Groups, Ed. Greene, John Wiley & Sons, 1981.

The acids and salts derived from compounds of Formula 1 and Formula 2 are readily obtainable from the corresponding esters. Basic saponification with an alkali metal base will provide the acid. For example, an ester may be dissolved in a polar solvent such as an alkanol, preferably under an inert atmosphere at room temperature, with about a three molar excess of base, for example, potassium or lithium hydroxide. The solution is stirred for an extended period of time, between 15 and 20 hours, cooled, acidified and the hydrolysate recovered by conventional means.

The amide (in Formula 1 or 2 B is $CONR_9R_{10}$) may be formed by any appropriate amidation means known in the art from the corresponding esters or carboxylic acids. One way to prepare such compounds is to convert an acid to an acid chloride and then treat that compound with ammonium hydroxide or an appropriate amine.

Alcohols are made by converting the corresponding acids to the acid chloride with thionyl chloride or other means (J. March, "Advanced Organic Chemistry", 2 nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978. 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

SPECIFIC EXAMPLES

Ethyl 4-Amino-2-fluorobenzoate (Compound $C_1$)

To a mixture of 2-fluoro-4-nitrotoluene (1.0 g, 6.4 mmol, Aldrich) and $Na_2Cr_2O_7$ (2.74 g, 8.4 mmol) in 13.7 ml of HOAC was added slowly 6.83 ml of $H_2SO_4$. This mixture was slowly heated to 90° C. for 1 h to give a greenish heterogeneous solution. The mixture was cooled to room temperature and diluted with ethyl acetate. The PH of the solution was adjusted to 4 with NaOH (aq.). The mixture was extracted with more ethyl acetate. The organic layer was washed with $NaHCO_3$ (sat.), then brine and dried over $Na_2SO_4$. After filtration, the solution was concentrated to dryness which then was dissolved in 6 ml of $SOCl_2$, and heated at 80° C. for 1 h. The excess of $SOCl_2$ was removed under reduced pressure and the residue was dissolved in 5 ml of $CH_2Cl_2$, 2 ml of EtOH and 2 ml of pyridine. The mixture was stirred at room temperature for 2 h and concentrated to dryness. Ethyl 2-fluoro-4-nitrobenzoate was obtained as a white solid after column chromatography of the residue with ethyl acetate/hexane (1/9). This solid was then dissolved in 10 ml of ethyl acetate, and Pd/C (50 mg) was added. Hydrogenation with a hydrogen balloon converted ethyl 2-fluoro-4-nitrobenzoate into the title compound.

$^1$H NMR δ 7.77 (t, J=8.4 Hz, 1H), 6.41 (dd, $J_1$=8.6, $J_2$=2.2 Hz, 1H), 6.33 (dd, $J_1$=13.0, $J_2$=2.2 Hz, 1H), 4.33 (q, J=7.1 Hz, 2H), 4.3 (b, 2H), 1.37 (t, J=7.1 Hz, 3H).

Methyl 4-Amino-2,6-difluorobenzoate (Compound $H_1$)

A solution of trifluorobenzoic acid (150 mg, 0.85 mmol, Aldrich) in 0.5 ml of $SOCl_2$ was heated under reflux for 2 h. The reaction mixture was cooled to room temperature, and excess of $SOCl_2$ was removed under reduced pressure. The residue was dissolved in 1 ml of pyridine and 0.2 ml of methanol. After stirring at room temperature for 30 min, solvent was removed and the residue was purified by column chromatography (ethyl acetate/hexane 1/10) to give methyl trifluorobenzoate as a colorless oil. This oil was then dissolved in 1 ml of $CH_3CN$, then a solution of $NaN_3$ (100 mg, 1.54 mmol) in 0.5 ml of water was added. The reaction mixture was refluxed for two days. Salt was efiltered and the remaining solution was concentrated to an oil. This oil was then dissolved in 1 ml of methanol, followed by a catalytic amount of Pd/C (10%, w/w). The reaction mixture was hydrogenated under a hydrogen balloon for 12 h. Catalyst was removed and the solution was concentrated to an oil. After column chromatography (ethyl acetate/hexane 1/3), the title product was obtained as colorless crystals.

$^1$H NMR δ 6.17 (d, J=10.44 Hz, 2H), 4.2 (b, 2H), 3.87 (s, 3H).

8-Bromo-2,2,4,4-tetramethyl-6-chromanoic acid (Compound P)

To a solution of 2,2,4,4-tetramethyl-6-chromanoic acid (200 mg, 0.85 mmol) in 0.5 ml of AcOH was added $Br_2$ (0.07 ml, 1.28 mmol). The resulting dark-orange solution was stirred at room temperature for overnight. The excess bromine was removed under reduced pressure. Then the solution was poured into 5 ml of water and extracted with ethyl acetate (3×3 ml). The combined ethyl acetate layers were further washed with $NaHCO_3$ (sat.), brine and dried over $MgSO_4$. After concentration, the residue was purified by column chromatography (silica gel, ethyl acetate/hexane 1/3) to yield the desired product (170 mg, as white solids.

$^1$H NMR δ 8.11 (d, J=2.2 Hz, 1H), 8.00 (d, J=2.2 Hz, 1H), 1.90 (s, 2H), 1.43 (s, 6H), 1.39 (s, 6H).

8Iodo-2,2,4,4-tetramethy-6-chromanoic Acid (Compound X)

To a solution of 2,2,4,4-tetramethyl-6-chromanoic acid (66 mg, 0.28 mmol) in 0.8 ml of ACOH was added ICl (0.07 ml, 1.4 mmol). The resulting colored solution was stirred at room temperature for overnight. Following the same procedure as for the synthesis of 8-bromo-2,2,4,4-tetramethyl-6-chromanoic acid (Compound P), the reaction gave the title compound (107 mg) as white solids.

$^1$H NMR δ 8.35 (d, J=2.2 Hz, 1H), 8.03 (d, J=2.2 Hz, 1H), 1.87 (s, 2H), 1.43 (s, 6H), 1.38 (s, 6H).

2,2,4,4-Tetramethyl-8-trifluoromethylchroman-6-oic acid (Compound 8)

A solution of 8-bromo-2,2,4,4-tetramethyl-6-chromanoic acid (Compound R, 150 mg, 0.48 mmol) in 1 ml of $SOCl_2$ was refluxed for 2 h. After cooling to room temperature, the excess of $SOCl_2$ was removed under reduced pressure and the residue was dissolved in 1 ml of pyridine and 0.2 ml of methanol. The mixture was stirred at room temperature for 30 min. Solvent was removed and the residue was passed through a column (silica gel, ethyl acetate/hexane 1/10) to give the methyl 8-bromo-2,2,4,4-tetramethylchromanoate (158 mg) as a colorless oil. To a solution of this methyl ester in 3 ml of N-methylpyrrolidone (NMP) was added $NaCO_2CF_3$ (502 mg, 3.7 mmol) and CuI (350 mg, 1.84 mmol). The resulting mixture was heated to 175° C. (bath temp) for 2 h. The resulting mixture was cooled to room temperature and poured into ice-water. The product was extracted into ethyl acetate (3×3 ml). The combined organic layers were dried and concentrated to dryness. The crude material was purified by column chromatography (ethyl acetate/chloroform 1/10) to give the title compound as a colorless oil (120 mg). This was hydrolyzed under standard conditions to give the title compound.

$^1$H NMR δ 8.21 (d, J=2.1 Hz, 1H), 8.17 (d, J=2.1 Hz, 1H), 1.92 (s, 2H), 1.41 (s, 12H).

Ethyl 8-Nitro-2,2,4,4-tetramethyl-6-chromanoate (Compound W)

Ethyl 2,2,4,4-tetramethyl-6-chromanoate (150 mg, 0.57 mmol) was slowly added to 0.3 ml of conc. $H_2SO_4$ at 0° C. To this mixture was added very slowly 0.03 ml of $HNO_3$. The reaction mixture was stirred at 0° C. for 30 min and poured into ice-water. The product was extracted into 5 ml of ethyl acetate, washed with $NaHCO_3$ (sat.), brine and dried over $MgSO_4$. After concentration, the product was purified by column chromatography (ethyl acetate/hexane 1/10) to yield 74 mg of light-yellow oil.

$^1$H NMR δ 8.24 (d, J=2.1 Hz, 1H), 8.17 (d, J=2.1 Hz, 1H), 4.38 (q, J=7.1 Hz, 2H), 1.95 (s, 2H), 1.43 (s, 6H), 1.42 (s, 6H), 1.40 (t, J=7.1 Hz, 3H).

2-Oxo-4,4,8-trimethylchroman (Compound $P_1$)

In a 500 ml of round bottom flask, NaH (1.66 g, 60% suspension in oil, 0.046 mol) was washed with dry hexane. Then, dry THF (22 ml) was added followed by o-cresol (5 g, 0.046 mol) in 10 ml of dry THF. The reaction mixture was stirred at 0° C. for 30 min followed by addition of 3,3-dimethyl acryloyl chloride in 10 ml of THF. The resulting white slurry was stirred at room temperature for 12 h, then slowly quenched with water. The mixture was then extracted with ethyl acetate. The organic layer was washed with brine, water and dried over $MgSO_4$. After filtration and removal of the solvent, a yellow oil was obtained (10.44 g). This oil was then dissolved in 50 ml of dry $CH_2Cl_2$, and was canulated into a solution of $AlCl_3$ (10.8 g, 0.069 mmol) in 10 ml of $CH_2Cl_2$. The reaction mixture was stirred at room temperature for 12 h. Then ice-water was carefully added and the organic layer was separated, and washed with $NaHCO_3$ (sat), brine, water and finally dried over $MgSO_4$ After removal of the drying agent and solvent, the residue was purified by column chromatography (silica gel, ethyl acetate/hexane 1/9) to yield the title compound (4.408 g) as an oil.

$^1$H NMR δ 7.1 (m, 3H), 2.62 (s, 2H), 2.33 (s, 3H), 1.36 (s, 6H).

2,4-Dimethyl-4-(2'-hydroxy-3'-methylphenyl) pentan-2-ol (Compound $R_1$)

To a solution of 2-oxo-4,4,8-trimethylchroman (Compound $P_1$, 2.20 g, 11.5 mmol) in 40 ml of dry ethyl ether was added methyl magnesium bromide (12.67 ml, 38 mmol, 3 M solution in THF). The reaction mixture was stirred at room temperature for 12 h, then quenched with $NH_4Cl$ (sat.) until all precipitate dissolved. The mixture was extracted with diethyl ether and the combined organic layers were separated and washed with brine, water and dried over $MgSO_4$. After filtration and removal of the solvent, the title compound was obtained as a tan solid (2.215 g).

$^1$H NMR δ 7.16 (d, J=7.88 Hz, 1H), 7.00 (d, J=6.72 Hz, 1H), 6.81 (t, J=7.6 Hz, 1H), 5.89 (b, 1H), 2.21 (s, 3H), 2.17 (s, 2H), 1.48 (s, 6H), 1.10 (s, 6H).

2,2,4,4,8-Pentamethyl-6-bromochroman (Compound Z)

A solution of 2,4-dimethyl-4-(2'-hydroxy-3'-methylphenyl)pentan-2-ol (Compound $R_1$, 2.215 g, 9.98 mmol) in 30 ml of 15% of $H_2SO_4$ was heated to 110° C. After cooling to room temperature, the reaction mixture was extracted with diethyl ether. The organic layer was washed with $NaHCO_3$ (sat.), brine and water. After filtration and removal of solvent, the residue was passed through a column (silica gel, pure hexane) to give the title compound as a clear oil (1.636 g). This oil was then dissolved in 1.5 ml of HOAc, then $Br_2$ (0.4113 ml, 7.98 nmol) was added. The reaction mixture was stirred at room temperature for 12 h. Solvent was removed under reduced pressure and to the residue was added ethyl acetate, and the resulting mixture was washed with $NaHCO_3$ (sat.), brine, water and dried over $MgSO_4$. After filtration and removal of solvent, the residue was passed through a column (silica gel, pure hexane) to give the title compound as a white solid (2.227 g).

$^1$H NMR δ 7.21 (s, 1H), 7.06 (s, 1H), 2.14 (s, 3H), 1.79 (s, 2H), 1.32 (s, 6H), 1.31 (s, 6H).

2,2,4,4,8-Pentamethyl-6-chromanoic Acid (Compound A₁)

To a solution of 2,2,4,4,8-pentamethyl-6-bromochroman (Compound Z) (1.2 g, 4.24 mmol) in 18 ml of dry THF at −78° C. under argon gas was added slowly 5.48 ml of t-BuLi (1.7 M in hexane, 9.33 mmol). The reaction mixture was stirred at −78° C. for 1 h. Then $CO_2$ was bubbled through the solution for 1 h. After removal of $CO_2$stream, the reaction mixture was stirred for an additional hour at −78° C. Then 10% of HCl was added. After warming up to room temperature, the reaction mixture was extracted with ethyl acetate. The organic layer was further washed with brine and dried over $Na_2SO_4$. After concentration, the residue was purified by column chromatography (ethyl acetate/hexane 5/95) to yield the title compound as a white solid (774 mg).

$^1$H NMR δ 7.96 (s, 1H), 7.75 (s, 1H), 2.23 (s, 3H), 1.88 (s, 2H), 1.39 (s, 6H).

8-Bromo-4,4-dimethyl-6-chromanoic Acid (Compound B₁)

Using the same procedure as for the synthesis of 8-bromo-2,2,4,4-tetramethylchromanoic acid (Compound P) but using 4,4-dimethylchromanoic acid (100 mg, 0.49 mmol), the title compound was obtained as a white solid.

$^1$H NMR δ 8.10 (d, J=2.1 Hz, 1H), 7.98 (d, J=2.1 Hz, 1H), 4.39 (t, J=5.44 Hz, 2H), 1.89 (t, J=5.4 Hz, 1H), 1.38 (s, 6H).

Ethyl 2-Amino-1-bromo-5,5,8,8-tetrahydro-5,5,8,8-tetramethylnaphthalene-3-carboxylate (Compound D)

To a solution of ethyl 5,6,7,8-tetrahydro-5,5,8,8-tetramethyl-3-aminonaphthalene-2-carboxylate (Compound C, 58 mg, 0.21 mmol) in 2 ml of HOAc was added $Br_2$ (0.02 ml, 0.42 mmol). The orange solution was stirred at room temperature for 2 days. The excess $Br_2$ and HOAC were removed under reduced pressure and the residue was passed through a column (silica gel, ethyl acetate/hexane 1/10) to yield the title compound as a light-orange oil (59 mg, 79.5%).

$^1$H NMR δ 7.90 (s, 1H), 6.41 (b, 2H), 4.36 (q, J=7.2 Hz, 2H), 1.70 (m, 4H), 1.58 (s, 6H), 1.40 (t, J=7.2 Hz, 3H), 1.28 (s, 6H).

Ethyl 5,6,7,8-tetrahydro-5,5,8,8-tetramethyl-4-bromonaphthalene-2-carboxylate (Compound E)

Ethyl 2-Amino-1-bromo-5,5,8,8-tetrahydro-5,5,8,8-tetramethylnaphthalene-3-carboxylate (Compound D, 59 mg, 0.17 mmol) was dissolved in 2 ml of EtOH at 0° C. To this solution was added 1 ml of trifluoroacetic acid and 1 ml of isoamylnitrite. The reaction mixture was stirred at 0° C. for 30 min then $H_3PO_2$ (0.325 ml, 3.14 mmol) was added. The reaction mixture was allowed to warm to room temperature and stirred for 12 h. $NaHCO_3$ (sat.) was added and the reaction mixture was extracted with ethyl acetate, dried over $MgSO_4$, filtered and concentrated to give an oil. The product was purified by column chromatography (silica gel, ethyl Aacetate/hexane 1/10) to give the title compound as a colorless oil.

$^1$H NMR δ 8.02 (d, J=2.0 Hz, 1H), 7.95 (d, J=2.0 Hz, 1H), 4.35 (q, J=7.1 Hz, 2H), 1.71 (m, 4H), 1.56 (s, 6H), 1.38 (t, J=7.1 Hz, 3H), 1.31 (s, 6H).

Ethyl 5,6,7,8-tetrahydro-5,5,8,8-tetramethyl-3-fluoronaphthalen-2-yl-carboxylate (Compound G)

In an ice bath, ethyl 5,6,7,8-tetrahydro-5,5,8,8-tetramethyl-3-aminonaphthalene-2-carboxylate (Compound C, 150 mg, 0.55 nmol) was added 0.24 ml of $HBF_4$ (48% solution in water), followed by a solution of $NaNO_2$ (81 mg, 1.16 mmol) in 1 ml of water. The slurry was left in a refrigerator for 3 days. The reaction mixture was washed successively with ethyl acetate until TLC showed no UV visible spot at the baseline. The ethyl acetate layer was dried with $MgSO_4$ and the solution was concentrated to an oil. The oil was further dissolved in 1 ml of toluene and the mixture was heated under reflux for 2 h. After the reaction cooled to room temperature, solvent was evaporated and the residue was passed through a column (silica gel, ethyl acetate/hexane 1/10) to give the title compound as an oil.

$^1$H NMR δ 7.85 (d, J=7.8 Hz, 1H), 7.04 (d, J=12.3 Hz, 1H), 4.38 (q, J=7.1 Hz, 2H), 1.69 (s, 4H), 1.38 (t, J=7.1 Hz, 3H), 1.30 (s, 6H), 1.28 (s, 6H).

2-Bromp-3-hydroxy-5,5,8,8-tetrahydro-5,5,8,8-tetramethylnaphthalene (Compound I)

Using the same procedure as for the synthesis of 8-bromo-2,2,4,4-tetramethyl-6-chromanoic acid (Compound P) but using 2-hydroxy-5,5,8,8-tetrahydro-5,5,8,8-tetramethyltetralin (700 mg, 3.43 mmol) and $Br_2$ (0.177 ml, 3.43 mmol) in 1.5 ml of HOAc, the title compound was obtained as a white solid (747 mg).

$^1$H NMR δ 7.36 (s, 1H), 6.96 (s, 2H), 5.32 (b, 1H), 1.66 (s, 4H), 1.25 (s, 12H).

5,6,7,8-Tetrahydro-5,5,8,8-tetramethyl-3-methoxymethoxy-2-bromopnaphthalene (Compound J)

To a solution of 2-bromo-3-hydroxy-5,5,8,8-tetrahydro-5,5,8,8-tetramethylnaphthalene (Compound I, 600 mg, 2.12 mmol) and catalytic amount of $Bu_4NBr$ in 20 ml of dry $CH_2Cl_2$ at 0° C. was added diisoproylethylamine (1.138 ml, 12.75 nmol), followed by methoxymethyl chloride (0.484 ml, 6.39 mmol). The reaction mixture was heated at 45° C. for 12 h. The reaction mixture was washed with 10% of citric acid, then $NaHCO_3$ (sat.), brine and dried over $MgSO_4$. After filtration and removal of the solvent, the residue was purified by column chromatography (ethyl acetate/hexane 1/9) to yield the title compound (722 mg) as a white solid.

$^1$H NMR δ 7.43 (s, 1H), 7.06 (s, 1H), 5.21 (s, 2H), 3.54 (s, 3H), 1.66 (s, 4H), 1.26 (s, 6H), 1.25 (s, 6H).

3-Methoxymethoxy-5,5,8,8-tetramethyl-5,6,7,8-tetrahydronaphthalen-2-yl carboxylic acid (Compound K)

Using the same procedure as for the synthesis of 2,2,4,4,8-pentamethyl-6-chromanoic acid (Compound A₁) but using 5,6,7,8-tetrahydro-5,5,8,8-tetramethyl-3-methoxymethoxy-2-bromonaphthalene (Compound J, 722 mg, 2.21 mmol) and 2.86 ml of t-BuLi (4.87 mmol, 1.7 M solution in hexane), the title compound was obtained as a white solid (143 mg).

$^1$H NMR δ 8.12 (s, 1H), 7.19 (s, 1H), 5.40 (s, 2H), 3.58 (s, 3H), 1.70 (s, 4H), 1.30 (s, 12H).

Ethyl 2-Fluoro-4-[(5',6',7'8'-tetrahydro-5',5',8',8'-tetramethylnaphthalen-2'-yl)carbomoyl]benzoate (Compound 1)

To 5,5,8,8-tetramethyl-5,6,7,8-tetrahydro-2-naphthoic acid (46 mg, 0.2 mmol) was added 1 ml thionyl chloride. This mixture was refluxed for 2 h. Excess thionyl chloride was removed under reduced pressure and the residue was dissolved in 2 ml of $CH_2Cl_2$. To this solution was added ethyl 4-amino-2-fluorobenzoate ((Compound $C_1$, 37 mg, 0.2 mmol) followed by 0.5 ml of pyridine. The reaction mixture was stirred at room temperature for 4 h and was concentrated under reduced pressure. The residue was purified by column chromatography (ethyl acetate/hexane 1/10) to give the title compound as white solids.

$^1$H NMR δ 8.06 (b, 1H), 7.93 (t, J=8.4 Hz, 1H), 7.85 (d, J=2.0 Hz, 1H), 7.78 (dd, $J_1$=2.0 Hz, $J_2$=12.9 Hz, 1H), 7.55 (dd, $J_1$=2.0 Hz, $J_2$=8.2 Hz, 1H), 7.40 (d, J=8.3 Hz, 1H), 7.32 (dd, $J_1$=2.02 Hz, $J_2$=8.8 Hz, 1H), 4.38 (q, J=7.2 Hz, 2H), 1.71 (s, 4H), 1.40 (t, J=7.2 Hz), 1.32 (s, 6H), 1.30 (s, 6H).

Ethyl 2-Fluoro-4-[(5',6',7',8'-tetrahydro-4'-bromo-5', 5',8'8'-tetramethylnaphthalen-2'-yl)carbamoyl]benzoate (Compound 3)

Using the same procedure as for the synthesis of ethyl 2-fluoro-4-[-5',6',7',8'-tetrahydro-5',5',8',8'-tetramethylnaphthalen-2'-yl)carbamoyl]benzoate (Compound 1), but using 5,6,7,8-tetrahydro-5,5,8,8-tetramethyl-4-bromonaphthalene-2-carboxylic acid (Compound F), the title compound was obtained as a white solid.

$^1$H NMR δ 8.30 (b, 1H), 7.92 (t, J=8.4 Hz, 1H), 7.84 (d, J=2.1 Hz, 1H), 7.81 (d, J=2.1 Hz, 1H), 7.74 (dd, $J_1$=2.1 Hz, $J_2$=12.8 Hz, 1H), 7.35 (dd, $J_1$=2.0 Hz, $J_2$=8.4 Hz, 1H), 4.36 (q, J=7.2 Hz, 2H), 1.67 (m, 4H), 1.55 (s, 6H), 1.39 (t, J=7.2 Hz, 3H), 1.31 (s, 6H).

Ethyl 2-Fluoro-4-[(3'-methoxymethoxy-5',6',7',8'-tetrahydro-5',5',8',8'-tetramethylnaphthalen-2'-yl) carabamoyl]benzoate (Compound $K_1$)

Using the same procedure as for the synthesis of ethyl 2-fluoro-4-[(3'-methoxymethoxy-4'-bromo-5',6',7',8'-tetrahydro-5',5',8',8'-tetramethylnaphthalen-2'-yl) carbamoyl]benzoate (Compound $S_1$), but using 3-methoxymethoxy-5,5,8,8-tetramethyl-5,6,7,8-tetrahydronaphthalen-2-yl carboxylic acid (Compound K, 143 mg, 0.49 mmol) and 4-amino-2-fluorobenzoate (Compound $C_1$, 98.5 mg, 0.54 mmol), the title compound was obtained as a white solid.

$^1$H NMR δ 10.1 (b, 1H), 8.20 (s, 1H), 7.93 (t, J=8.8 Hz, 1H), 7.83 (d, J=13.4 Hz, 1H), 7.29 (d, J=8.0 Hz, 1H), 5.41 (s, 2H), 4.39 (q, J=7.1 Hz, 2H), 3.59 (s, 3H), 1.70 (s, 4H), 1.31 (s, 12H), 1.26 (t, J=7.1 Hz, 3H).

Ethyl 2-Fluoro-4-[(3'-hydroxy-5',6',7',8'-tetrahydro-5',5',8',8'-tetramethyl-2-naphthalenyl)carbamoyl]benzoate (Compound 5)

A solution of ethyl 2-fluoro-4-[(3'-methoxymethoxy-5',6',7',8'-tetrahydro-5',5',8',8'-tetramethylnaphthalen-2'-yl) carbamoyl]benzoate (Compound $K_1$, 50.7 mg, 0.11 mmol) in 2 ml of $CH_2Cl_2$ was added thiophenol (0.061 ml, 0.55 mmol). The reaction mixture was stirred at 0° C. for 5 min, then $BF_3.Et_2O$ (0.027 ml, 0.22 mmol) was added. The reaction mixtrue was stirred at 0° C. for 2 h, then $NaHCO_3$ (sat.) was added. The organic layer was separated, and washed with brine, water and dried over $MgSO_4$. After filtration and removal of solvent, the residue was passed through a column (silica gel, ethyl acetate/hexane 1/3) to give the title compound as white solid (44.2 mg).

$^1$H NMR δ 8.61 (b, 1H), 7.94 (t, J=8.42 Hz, 1H), 7.71 (dd, J=10.8, 2.0 Hz, 1H), 7.53 (s, 1H), 7.35 (dd, J=6.4, 2.0 Hz, 1H), 6.96 (s, 1H), 4.39 (q, J=7.1 Hz, 2H), 1.69 (s, 4H), 1.40 (t, J=7.1 Hz, 3H), 1.29 (s, 6H), 1.27 (s, 6H).

Ethyl 2-Fluoro-4-[(4',4'-dimethyl-8'-bromochroman-6'-yl)carbamoyl]benzoate (Compound 7)

In a 10 ml of round bottom flask, 4,4-dimethyl-8-bromo-6-chromanoic acid (Compound $B_1$, 139 mg, 0.485 mmol) was added $SOCl_2$ (1 ml large excess). The resulting solution was heated at 90° C. for 2 h and allowed to cool to room temperature. The excess of $SOCl_2$ was evaporated under reduced pressure. The residue was dissolved in $CH_2Cl_2$ (3 ml). Ethyl 4-amino-2-fluorobenzoate (Compound $C_1$, 90 mg, 0.49 mmol) was added followed by pyridine (0.5 ml, large excess). The reaction mixture was stirred for overnight and then concentrated to dryness. The residue was purified by column chromatography with ethyl acetate/hexane (1/5) to yield the title compound as a white solid (190 mg).

$^1$H NMR δ 7.95 (t, J=8.31 Hz, 1H), 7.88 (b, 1H), 7.83 (d, J=2.2 Hz, 1H), 7.80 (d, J=2.2 Hz, 1H), 7.75 (dd, J=12.89, 2.0 Hz, 1H), 7.30 (dd, J=8.55, 2.0 Hz, 1H), 4.37 (m, 5H), 1.89 (t, J=5.49 Hz, 2H), 1.40 (t, J=7.1 Hz, 3H), 1.39 (s, 6H).

Ethyl 2-Fluoro-4-[(2',2',4',4'-tetramethyl-8'-bromochroman-6'-yl)carbamoyl]benzoate (Compound 9)

Using the same procedure as for ethyl 2-fluoro-4-[(4',4'-dimethyl-8'-bromochroman-6'-yl)carbamoyl]benzoate (Compound 7), but using 2,2,4,4-tetramethyl-8-bromo-6-chromanoic acid (Compound P, 70 mg, 0.22 mmol) and ethyl 4-amino-2-fluorobenzoate (Compound $C_1$, 38 mg, 0.22 mmol), the title compound was obtained as a white solid (80 mg, 76%).

$^1$H NMR δ 8.25 (b, 1H), 7.92 (t, J=8.4 Hz, 1H), 7.83 (s, 2H), 7.74 (dd, $J_1$=2.0, $J_2$=13.0 Hz, 1H), 7.34 (dd, $J_1$=2.0, $J_2$=8.7 Hz, 1H), 4.37 (q, J=7.1 Hz, 2H), 1.88 (s, 2H), 1.41 (s, 6H), 1.39 (t, J=7.1 Hz, 3H), 1.37 (s, 6H).

Ethyl 2-Fluoro-4-[(2',2',4',4'-tetramethyl-8'-trifluoromethylchroman-6'-yl)carbamoyl]benzoate (Compound 11)

Using the same procedure as for ethyl 2-fluoro-4-[(4',4'-dimethyl-8'-bromochroman-6'-yl)carbamoyl]benzoate (Compound 7), but using 2,2,4,4-tetramethyl-8-trifluoromethyl-6-chromanoic acid (Compound S, 57 mg, 0.19 mmol) and ethyl 4-amino-2-fluorobenzoate (Compound $C_1$, 35 mg, 0.19 mmol), the title compound was obtained as white solids.

$^1$H NMR δ 8.06 (d, J=2.2 Hz, 1H), 7.99 (b, 1H), 7.95 (t, J 8.55 Hz, 1H), 7.81 (d, J=2.2 Hz, 1H), 7.76 (dd, J=12.8, 2.1 Hz, 1H), 7.33 (dd, J=8.55, 1.9 Hz, 1H), 4.37 (q, J=7.1 Hz, 2H), 1.93 (s, 2H), 1.41 (s, 12H), 1.40 (t, J=7.2 Hz, 3H).

Ethyl 2-Fluoro-4-[(2',2',4',4'-tetramethyl-8'-aminochroman-6'-yl)carbamoyl]benzoate (Compound $N_1$)

Using 8-nitro-2,2,4,4-tetramethylchroman-6-carboxylic acid (Compound V) and following the same procedure as for the synthesis of ethyl 2-fluoro-4-[(4',4'-dimethyl-8'-bromochroman-6'-yl)carbamoyl]benzoate (Compound 7), ethyl 2-fluoro-4-[2',2',4',4'-tetramethyl-8'-nitrochroman-6'-yl)]carbamoylbenzoate was obtained as a white solid. This compound (50 mg, 0.12 mmol) was dissolved in 2 ml of methanol. A catalytic amount of Pd/C was added to the solution and the solution was maintained under $H_2$ atmosphere (hydrogen balloon) for overnight. The catalyst was removed by filtration and the solvent was evaporated to give the title compound as a white solid.

$^1$H NMR δ 7.93 (t, J=8.43 Hz, 1H), 7.90 (b, 1H), 7.73 (dd, J=12.9, 2.0 Hz, 1H), 7.29 (dd, J=8.43, 1.96 Hz, 1H), 7.23 (d,

J=2.14 Hz, 1H), 7.01 (d, J=2.2 Hz, 1H), 4.35 (q, J=7.1 Hz, 2H), 1.88 (s, 2H), 1.39 (s, 6H), 1.38 (t, J=7.1 Hz, 3H), 1.37 (s, 6H).

Ethyl 2-Fluoro-4-[(2',2',4',4'-tetramethyl-8'-azidochroman-6'-yl)carbamoyl]benzoate (Compound 13)

To a solution of ethyl 2-fluoro-4-[(2',2',4',8'-aminochroman-6'-yl)carbamoyl]benzoate (Compound $N_1$, 32 mg, 0.077 mmol) in 3 ml of EtOH was added 0.5 ml of trifluoroacetic acid (TFA) and 0.5 ml of isoamylnitrite at 0° C. The reaction was stirred for 2 h when a solution of $NaN_3$ (5 mg, ) in 0.2 ml of water was added. The reaction mixture was allowed to warm to room temperature and stirred for overnight. The solvent was removed and the residue was purified by column chromatography (silica gel, ethyl acetate/hexane 1/10) to give the title compound as a colorless oil.

$^1$H NMR δ 8.0 (b, 1H), 7.94 (t, J=7.8 Hz, 1H), 7.73 (d, J=12.1 Hz, 1H), 7.64 (s, 1H), 7.31 (dd, J=8.5, 2.0 Hz, 1H), 7.21 (d, J=2.0 Hz, 1H), 4.37 (q, J=7.1 Hz, 2H), 1.90 (s, 2H), 1.39 (t, J=7.1 Hz, 3H), 1.45 (s, 6H), 1.40 (s, 6H).

Methyl 2,6-Difluoro-4-[(2',2',4',4'-tetramethyl-8'-trifluoromethylchroman-6'-yl)carbamoyl]benzoate (Compound 15)

Using the same procedure as for ethyl 2-fluoro-4-[(4',4'-dimethyl-8'-bromochroman-6'-yl)carbamoyl]benzoate (Compound 7), but using 2,2,4,4-tetramethyl-8-trifluoromethylchromanoic acid (Compound S, 11.2 mg, 0.037 mmol) and methyl 4-amino-2,6-difluorobenzoate (Compound $H_1$, 6.6 mg, 0.035 mmol), the title compound was obtained as white crystals.

$^1$H NMR δ 8.21 (b, 1H), 8.05 (s, 1H), 7.82 (s, 1H), 7.36 (d, J=10.20 Hz, 1H), 3.93 (s, 3H), 1.92 (s, 2H), 1.40 (s, 12H).

Ethyl 2-Fluoro-4-[(2',2',4',4'-tetramethyl-8'-iodochroman-6'-yl)carbamoyl]benzoate (Compound 17)

Using the same procedure as for ethyl 2-fluoro-4-[(4',4'-dimethyl-8'-bromochroman-6'-yl)carbamoyl]benzoate (Compound 7), but using 2,2,4,4-tetramethyl-8-iodochromanoic acid (Compound X, 81 mg, 0.25 mmol) and ethyl 4-amino-2-fluorobenzoate ((Compound $C_1$, 55 mg, 0.30 mmol), the title compound was obtained as a white solid.

$^1$H NMR δ 8.05 (b, 1H), 8.01 (d, J=2.2 Hz, 1H), 7.94 (t, J 8.4 Hz, 1H), 7.86 (d, J=2.2 Hz, 1H), 7.75 (dd, J=12.88, 2.1 Hz, 1H), 7.33 (dd, J=8.8, 2.1 Hz, 1H), 4.37 (q, J=7.1 Hz, 2H), 1.89 (s, 2H), 1.42 (s, 6H), 1.38 (s, 6H).

Ethyl 2-Fluoro-4-[(2',2',4',4',8'-pentamethylchroman-6'-yl)carbamoyl]benzoate (Compound 19)

Using the same procedure as for ethyl 2-fluoro-4-[(4',4'-dimethyl-8'-bromochroman-6'-yl)carbamoyl]benzoate (Compound 9), but using 2,2,4,4,8-pentamethyl-6-chromanoic acid (Compound $A_1$, 92 mg, 0.37 mmol) and ethyl 4-amino-2-fluorobenzoate (Compound $C_1$, 75 mg, 0.41 mmol), the title compound was obtained as a white solid (100 mg).

$^1$H NMR δ 8.31 (b, 1H), 7.90 (t, J=8.24 Hz, 1H), 7.76 (dd, J=14.29, 1.7 Hz, 1H), 7.74 (s, 1H), 7.43 (s, 1H), 7.35 (dd, J=8.67, 1.7 Hz, 1H), 4.32 (q, J=7.1 Hz, 2H), 2.18 (s, 3H), 1.84 (s, 2H), 1.38 (t, J=7.1 Hz, 3H), 1.35 (s, 6H), 1.34 (s, 6H).

Ethyl 4-[(5',6',7',8'-tetrahydro-5',5',8',8'-tetramethyl-2-naphthalenyl)thiocarbamoyl]benzoate (Compound 21)

To a solution of ethyl 4-((5',6',7',8'-tetrahydro-5',5',8',8'-tetramethylnaphthalen-2-yl)carbamoyl]benzoate (Compound $I_1$, 61 mg, 0.16 mmol) in 2 ml of anhydrous benzene was added Lawesson's reagent (45 mg, 0.112 mmol). The resulting yellow solution was refluxed under $N_2$ for 2 h. The solvent was removed and the residue was purified by column chromatography (silica gel, ethyl acetate/hexane 1/5) to give the title compound as a yellow solid (55 mg, 87%). $^1$H NMR δ 9.04 (b, 1H), 8.11 (d, J=8.70 Hz, 2H), 7.85 (b, 2H), 7.75 (b, 1H), 7.55 (dd, J=8.2, 1.9 Hz, 1H), 7.36 (d, J=8.3 Hz, 1H), 4.38 (q, J=7.1 Hz, 2H), 1.71 (s, 4H), 1.40 (t, J=7.1 Hz, 3H), 1.30 (s, 12H).

Ethyl 2-Fluoro-4-[(5',6',7',8'-tetrahydro-5',5',8',8'-tetramethylnaphthalen-2'-ty)thiocarbamoyl]benzoate (Compound 23)

Using the same procedure as for the synthesis of ethyl 4-[(5',6',7',8'-tetrahydro-5',5',8',8'-tetramethyl-2-naphthalenyl)thiocarbamoyl]benzoate (Compound 21) but using ethyl 2-fluoro-4-[(5',6',7',8'-tetrahydro-5',5',8',8'-tetramethylnaphthalen-2'-yl)carbamoyl]benzoate (Compound 1, 167 mg, 0.42 mmol) in 8 ml of benzene and Lawenssol's reagent (220 mg, 0.544 mmol), the title compound was obtained as a bright yellow solid (127.5 mg).

$^1$H NMR δ 9.30 (b, 1H), 8.05 (b, 1H), 7.95 (t, J=8.37 Hz, 1H), 7.77 (d, J=1.89 Hz, 1H), 7.53 (dd, J=8.24, 2.1 Hz, 1H), 7.49 (b, 1H), 7.35 (d, J=8.24 Hz, 1H), 4.33 (q, J=7.1 Hz, 1H), 1.71. (s, 4H), 1.32 (s, 6H), 1.30 (s, 6H).

3-Hydroxy-5,5,8,8-tetramethyl-5,6,7,8-tetrahydronaphthalen-2-yl carboxylic acid (Compound L)

To a solution of 2-bromo-3-methoxymethoxy-5,5,8,8-tetrahydro-5,5,8,8-tetramethylnaphthalene (Compound J, 722 mg, 2.2 mmol) in 10 ml of dry THF at −78° C. under argon was added slowly 2.86 ml of t-BuLi (1.7 M in hexane, 4.8 mmol). The reaction mixture was stirred at −78° C. for 1 h. Then $CO_2$ was bubbled through the solution for 1 h. After removal of $CO_2$ stream, the reaction mixture was stirred for an additional hour at −78° C. Then 10% of HCl was added. After warming up to room temperature, the reaction mixture was left overnight then extracted with ethyl acetate. The organic layer was washed with brine and dried over $Na_2SO_4$. After concentration, the residue was purified by column chromatography (ethyl acetate/hexane 1/3) to yield the title compound as a white solid.

$^1$H NMR d 7.85 (s, 1H), 6.93 (s, 1H), 1.68 (s, 4H), 1.28 (s, 12H).

4-Bromo-3-hydroxy-5,5,8,8-tetramethyl-5,6,7,8-tetrahydronaphthalen-2-yl carboxylic acid (Compound M)

3-Hydroxy-5,5,8,8-tetramethyl-5,6,7,8-tetrahydronaphthalen-2-yl acid (Compound L, 155 mg, 0.62 mmol) was dissolved in 1 ml of HOAC. To this solution was added $Br_2$ (0.033 ml, 0.62 mmol). The reaction mixture was left at room temperature for over night. A stream of air was passed through the reaction mixture to remove the unreacted $Br_2$. The remaining solid was dissolved in small amount of THF and purified by column chromatography (ethyl acetate/hexane 1/1) to yield the desired product as a cream colored solid.

$^1$H NMR d 7.91 (s, 1H), 1.75 (m, 2H), 1.64 (m, 2H), 1,62 (s, 6H), 1.30 (s, 6H).

4-Bromo-3-methoxymethoxy-5,5,8,8-tetramethyl-5, 6,7,8-tetrahydronaphthalen-2-yl carboxylic acid (Compound N)

To a solution of 4-bromo-3-hydroxy-5,5,8,8-tetramethyl-5,6,7,8-tetrahydronaphthalen-2-yl acid (Compound M), 233 mg, 0.71 mmol) in 6 ml of $CH_2Cl_2$ was added chloromethyl methyl ether (0.162 ml, 2.1 mmol), diisopropylethyl amine (0.764 ml, 4.2 mmol) and a catalytic amount of tetrabutylammouimn bromide. The reaction mixture was heated to 45° C. for 2 h. The reaction mixture was concentrated and the residue was purified by column chromatography (ethyl acetate/hexane 1/9) to yield the methoxymethyl ester of the title compound as a white solid (200 mg). This white solid was further dissolved in 20 ml of EtOH. An aqueous solution of NaOH (0.5 ml, 1M) was added. The reaction mixture was stirred at room temperature for over night. The EtOH was removed and the residue was added 2 ml of ethyl acetate and 3 ml of water. This mixture was very slowly acidified with 10% HCl to PH=7. The ethyl acetate layer was separated and washed with brine, dried over $Na_2SO_4$. After filtration of the drying agent and removal of solvent, the reaction yielded the title compound as a white solid (155 mg). $^1$H NMR d 7.99 (s, 1H), 5.20 (s, 2H), 3.66 (s, 3H), 1.74 (m, 2H), 1.67 (m, 2H), 1.60 (s, 6H), 1.32 (s, 6H).

Ethyl 2-fluoro-4-[(3'-methoxymethoxy-4'-bromo-5', 6',7',8'-tetrahydro-5',5',8',8'-tetramethylnaphthalen-2'-yl)carbamoyl]benzoate (Compound $S_1$)

To a solution of 4-bromo-3-methoxymethoxy-5,5,8,8-tetramethyl-5,6,7,8-tetrahydronaphthalen-2-yl acid (Compound N, 80 mg, 0.22 mmol) in 4 ml of $CH_2Cl_2$ was added DMAP (60 mg, 0.26 mmol), ethyl 2-fluoro-4-aminobenzoate (Compound $C_1$, 43 mg, 0.24 mmol) and EDC (50 mg, 0.26 mmol). The reaction mixture was stirred at room temperature for overnight and then concentrated to dryness. The residue was purified by column chromatography (ethyl acetate/hexane 1/3) to yield the title compound as a clear oil (45 mg).

$^1$H NMR d 9.92 (b, 1H), 8.10 (s, 1H), 7.94 (t, J=8.4 Hz, 1H), 7.81 (dd, J=12.9; 1.9 Hz, 1H), 7.35 (dd, J=8.5; 1.8 Hz, 1H), 5.20 (s, 2H), 4.39 (q, J=7.1 Hz, 2H), 3.61 (s, 3H), 1.74 (m, 2H), 1.64 (m, 2H), 1.60 (s, 6H), 1.40 (t, J=7.1 Hz, 3H), 1.34 (s, 6H).

Methyl 2,6-Difluoro-4-[(3'-methoxymethoxy-4'-bromo-5',6',7',8'-tetrahydro-5',5',8',8'-tetramethylnaphlen-2'-yl)carbamoyl]benzoate (Compound $M_1$)

Using the same procedure as for the synthesis of compound ethyl 2-fluoro-4-[(3'-methoxymethoxy-4'-bromo-5', 6',7',8'-tetrahydro-5',5',8',8'-tetramethylnaphthalen-2'-yl) carbamoyl]benzoate (Compound $S_1$) but using 4-bromo-3-methoxymethoxy-5,5,8,8-tetramethyl-5,6,7,8-tetrahydronaphthalen-2-yl acid (Compound N, 80 mg, 0.22 mmol), DMAP (60 mg, 0.26 mmol), methyl 2,6-difluoro-4-aminobenzoate (Compound $H_1$, 52 mg, 0.24 mmol) and EDC (50 mg, 0.26 mmol), the title compound was obtained as a clear oil.

$^1$H NMR d 10.01 (b, 1H), 8.11 (s, 1H), 7.42 (d, J=10.0 Hz, 2H), 5.2 (s, 2H), 3.95 (s, 3H), 3.63 (s, 3H), 1.75 (m, 2H), 1.65 (m, 2H), 1.61 (s, 6H), 1.35 (s, 6H).

4-Bromomethyl-2,6-di-t-butylpyridine (Compound $A_3$)

To a mixture of 2,6-di-t-butyl-4-methylpyridine (Aldrich, 2.0 g, 9.73 mmol) in 25 ml of dry $CCl_4$ was added benzoyl peroxide (24 mg, 0.097 mmol) and NBS (1.9 g, 10.7 mmol). The reaction mixture was refluxed for 16 hours. After it cooled to room temperature, the solvent was removed iL vacuo and the residue was purified by column chromatography (silica gel, hexane) to give an oil (1.957 g) which contained 82% of the desired product and 18% of the starting material. $^1$H NMR δ 7.09 (s, 2H), 4.39 (s, 2H), 1.35 (s, 18H).

4-Hydroxymethyl-2,6-di-t-butylpyridine (Compound $B_3$)

A heterogeneous solution of 4-bromomethyl-2,6-di-t-butylpyridine (Compound $A_3$, 1.743 g, 82% purity) in 20 ml of 12% NaOH in water and 10 ml of 1,4-dioxane was refluxed for 12 hours. The solution spontaneously separated into two layers as it cooled to room temperature. The upper layer was separated and ethyl acetate was added. This organic layer was then washed with brine, water and dried over $MgSO_4$. The desired product was purified by column chromatography (ethyl acetate/hexane 1/9) to give a white solid. $^1$H NMR δ 7.09 (s, 2H), 4.67 (d, J=4.4 Hz, 2H), 2.3 (b, 1H), 1.36 (s, 18H).

2,6-Di-t-butylisonicotinic acid (Compound $C_3$)

Jone's reagent was added dropwise to a solution of 4-hydroxymethyl-2,6-di-yt-butylpyridine (Compound $B_3$, 302 mg, 1.37 mmol) in 5 ml of acetone until the solution changed color from light yellow to orange (55 drops of Jone's reagent were consumed). After 5 minutes 2 ml of isopropanol were added to the reaction mixture, and a green precipitate of $Cr^{3+}$ salt was formed. The precipitate was removed by filtration and the solution was diluted with ethyl acetate, then washed with brine, water and dried over $MgSO_4$. After filtration, the solvent was removed to give the desired product as a white solid (227 mg). $^1$H NMR δ 7.71 (s, 2H), 1.34 (s, 18H).

2-Bromo-4,6-di-t-butylphenol (Compound $D_3$)

To a solution of 2,4-di-t-butylphenol (Aldrich, 2.0 g, 9.7 mmol) in 2 ml of HOAc was added $Br_2$ (0–5 ml, 9.7 mmol). The reaction mixture was stirred at room temperature for 12 hours. Solvent was removed under reduced pressure and the residue was purified by column chromatography (ethyl acetate/hexane 1/20) to yield the desired product (2.54 g) as a white solid. $^1$H NMR δ 7.33 (d, J=2.3 Hz, 1H), 7.24 (d, J=2.3 Hz, 1H), 1.41 (s, 9H), 1.29 (s, 9H).

O-Methoxvmethyl-2-bromo-4,6-di-t-butylphenol (Compound $E_3$)

To a solution of 2-bromo-4,6-di-t-butylphenol (Compound $D_3$ 2.54 g, 8.88 mmol) and catalytic amount of $Bu_4NI$ in 20 ml of dry $CH_2Cl_2$ at 0° C. was added diisopropylethylamine (9.51 ml, 53 mmol), followed by methoxymethyl chloride (2.02 ml, 26.6 mmol). The reaction mixture was heated to 45° C. for 12 hours. The reaction mixture was then washed with 10% citric acid, then $NaHCO_3$ (sat.), brine, and dried over $MgSO_4$. After filtration and removal of the solvent under reduced pressure, the residue was purified by column chromatography (pure hexane) to yield the title compound (2.79 g) as a colorless oil. $^1$H NMR δ 7.40 (d, J=2.44 Hz, 1H), 7.30 (d, J=2.4 Hz, 1H), 5.22 (s, 2H), 3.70 (s, 3H), 1.43 (s, 9H), 1.29 (s, 9H).

O-Methoxvmethyl-3',5'-di-t-butylsalicylic acid (Compound $F_3$)

To a solution of O-methoxymethyl-2-bromo-4,6-di-t-butylphenol (Compound $E_3$, 2.79 g, 8.5 mmol) in 30 ml of dry THF at −78° C. under Ar was added 11 ml of t-BuLi (1.7 M in hexane, 18.7 mmol). This mixture was stirred at −78° C. for 1 hour. Then $CO_2$ (g) was bubbled into the solution at −78° C. for 1 hour. After removal of the $CO_2$ stream, the reaction mixture was stirred for an additional hour at −78° C. Then 10% of HCl was added and the mixture was allowed to warm to room temperature and extracted with ethyl acetate. The organic layer was washed with brine and dried over $Na_2SO_4$. After concentration, the residue was purified by column chromatography (ethyl acetate/hexane 1/1) to yield the title compound as a white solid (492 mg). $^1$H NMR δ 7.75 (d, J=2.81 Hz, 1H), 7.60 (d, J=2.8 Hz, 1H), 5.07 (s, 2H), 3.62 (s, 3H), 1.33 (s, 9H), 1.26 (s, 9H).

Ethyl 2-fluoro-4-[(2'6'-di-t-butylpyrid-4'-yl) carbamoyl]benzoate (Compound 41)

A solution of 2,6-di-t-butylisonicotinic acid (Compound $C_3$, 47.3 mg, 0.20 mmol) in 2 ml of $SOCl_2$ was heated under reflux for 2 hours. Excess $SOCl_2$ was removed in vacuo and the residue was dissolved in 2 ml of dry $CH_2Cl_2$, and ethyl 2-fluoro-4-aminobenzoate (Compound $C_1$, 40.2 mg, 0.22 mmol) and pyridine (0.0835 ml, 0.69 mmol) were added. The reaction mixture was stirred at room temperature for 12 hours. Solvent was removed and the residue was purified by column chromatography (ethyl acetate/hexane 1/9) to yield the title compound (71.2 mg) as white crystals. $^1$H NMR δ 8.56 (b, 1H), 7.91 (t, J=8.36 Hz, 1H), 7.53 (dd, J=12.82, 2.0 Hz, 1H), 7.39 (dd, J=8.7, 2.0 Hz, 1H), 4.33 (q, J=7.1 Hz, 2H), 1.37 (t, J=7.1 Hz, 3H), 1.35 (s, 18H).

Ethyl 4-[(2',6'-di-t-butylpyrid-4'-yl)carbamoyl] benzoate (Compound 43)

Using the same procedure as for the synthesis of ethyl 2-fluoro-4-[(2'6'-di-t-butylpyrid-4'-yl)carbamoyl]benzoate (Compound 41) but using 2,6-di-t-butylisonicotinic acid (Compound $C_3$, 101 mg, 0.43 mmol) and ethyl 4-aminobenzoate (78 mg, 0.47 mmol), the title compound was obtained as a white solid (135 mg). $^1$H NMR δ 8.43 (b, 1H), 8.02 (d, J=8.7 Hz, 2H), 7.75 (d, J=8.7 Hz, 2H), 7.48 (s, 2H), 4.33 (q, J=7.1 Hz, 2H), 1.38 (t, J=7.1 Hz, 3H), 1.35 (s, 18H).

Ethyl 2-Fluoro-4-[(3',5'-di-t-butylphenyl)carbamoyl] benzoate (Compound 45)

Using the same procedure as for the synthesis of ethyl 2-fluoro-4-[(2'6'-di-t-butylpyrid-4'-yl)carbamoyl]benzoate (Compound 41) but using 3,5-di-t-butylbenzoic acid (60 mg, 0.26 mmol, available by literature procedure, see Kagechika et al. J. Med Chem. 1988 31, 2182–2192) and ethyl 2-fluoro-4-aminobenzoate (Compound $C_1$, 51.5 mg, 0.28 mmol), the title compound was obtained as a white solid (66 mg). $^1$H NMR δ 8.21 (b, 1H), 7.93 (t, J=8.3 Hz, 1H), 7.79 (dd, J=12.8, 2.0 Hz, 1H), 7.67 (d, J=1.8 Hz, 2H), 7.65 (t, J=1.7 Hz, 1H), 7.35 (dd, J=8.7, 2.1 Hz, 1H), 4.36 (q, J=7.2 Hz, 2H), 1.39 (t, J=7.2 Hz, 3H), 1.36 (s, 18H).

Ethyl 2-Fluoro-4-[(2'-methoxymethyl-3',5'-di-t-butylrhenyl)carbamoyl]benzoate (Compound $G_3$)

To a mixture of O-methoxymethyl-3',5'-di-t-butylsalicylic acid (Compound $F_3$, 150 mg, 0.51 mmol), 4-dimethylaminopyridine (142 mg, 0.61 mmol) and ethyl 2-fluoro-4-aminobenzoate (Compound $C_1$, 102 mg, 0.56 mmol) in 5 ml of dry $CH_2Cl_2$ was added 1-(3-dimethylaminopropyl)-3-ethylcarbodiimide hydrochloride (117 mg, 0.61 mmol). The reaction mixture was stirred at room temperature for 12 hours. Solvent was evaporated in vacuo and the residue was dissolved in ethyl acetate, then washed with brine, water and dried over $MgSO_4$. After filtration, solvent was removed and the residue was purified by column chromatography (ethyl acetate/hexane 1/3) to give the title compound (58 mg). $^1$H NMR δ 8.97 (b, 1H), 7.94 (t, J=8.37 Hz, 1H), 7.78 (d, J=2.7 Hz, 1H), 7.61 (d, J=13.0 Hz, 1H), 7.56 (d, J=2.6 Hz, 1H), 7.35 (d, J=8.7 Hz, 1H), 5.00 (s, 2H), 3.53 (s, 3H), 4.38 (q, J=7.1 Hz, 2H), 1.47 (s, 9H), 1.39 (t, J=7.2 Hz, 3H), 1.33 (s, 9H).

Ethyl 2-Fluoro-4-[(2'-hydroxy-3',5'-di-t-butylphenyl carbamoyl]benzoate (Compound 47)

To a solution of ethyl 2-fluoro-4-[(2'-methoxymethyl-3', 5'-di-t-butylphenyl)carbamoyl]benzoate (Compound $G_3$, 34 mg, 0.07 mmol) in 1 ml of THF were added 10 drops of HOAc. The reaction mixture was heated to reflux for 12 hours. Solvent was removed and ethyl acetate was added. The solution was washed with $NaCHO_3$ (sat.), brine, water and dried over $MgSO_4$. Solvent was removed Mn vacuo to give an oil. The oil was allowed to be exposed to the atmosphere for 12 hours during which time crystals formed. The crystals were collected and washed several times with hexane to afford the title compound as a white solid (13.5 mg).
$^1$H NMR δ 10.73 (s, 1H), 7.98 (d, J=2.56 Hz, 1H), 7.88 (b, 1H), 7.75 (t, J=8.26 Hz, 1H), 7.60 (d, J=2.44 Hz, 1H), 7.32 (dd, J=12.3, 2.0 Hz, 1H), 7.02 (dd, J=8.6, 2.0 Hz, 1H), 4.35 (q, J=7.2 Hz, 2H), 1.39 (s, 9H), 1.37 (t, J=7.2 Hz, 3H), 1.5 (s, 9H).

2,6-Difluoro-4-[(2',6'-di-t-butylpyrid-4'-yl) carbamoyl]benzoic Acid (Compound 50)

To 2,6-di-t-butylisonicotinic acid (Compound $C_3$, 20 mg, 0.085 mmol) was added 1 ml of $SOCl_2$. The mixture was heated under reflux for 2 hours. After cooling to room temperature, excess $SOCl_2$ was removed and the residue was dissolved in 2 ml of $CH_2Cl_2$. To this solution was added methyl 2,6-difluoro-4-aminobenzoate (Compound $H_1$, 16 mg, 0.085 mmol) and triethylamine (0.015 ml, 0.1 mmol). The reaction mixture was kept at room temperature for 2 hours and then concentrated to dryness. The residue was purified by column chromatography with ethyl acetate/hexane (1/10) to yield the methyl ester of the title compound. This was saponified according to the general procedure (see below) to give the title compound as a colorless solid. $^1$H NMR δ 7.44 (s, 2H), 7.40 (d, J=11.8 Hz, 2H) 1.37 (s, 18H).

2,6-Difluoro-4-[(3',5'-di-t-butylphenyl)carbamoyl] benzoic Acid (Compound 52)

Using the same procedure as for the preparation of 2,6-difluoro-4-[(2',6'-di-t-butylpyrid-4'-yl)carbamoyl] benzoic acid (Compound 50) but using 3,5-di-t-butylbenzoic acid (37 mg, 0.16 mmol) and methyl 2,6-difluoro-4-aminobenzoate (Compound $H_1$, 29 mg, 0.16 mmol), the title compound was obtained as colorless crystals. $^1$H NMR δ 7.92 (b, 1H) 7.60 (m, 3H), 7.42 (d, J=10.0 Hz, 2H), 1.38 (s, 18H).

2-Nitro-4-[(2',6'-di-t-butylpyrid-4'-yl)carbamoyl] benzoic Acid (Compound 54)

Using the same procedure as for the preparation of 2,6-difluoro-4-[(2',6'-di-t-butylpyrid-4'-yl)carbamoyl] benzoic acid (Compound 50) but using 2,6-di-t- butylisonicotinic acid (40 mg, 0.17 mmol) and methyl 2-nitro-4-aminobenzoate (Compound F$_1$, 33 mg, 0.17 mmol), the title compound was obtained as a light yellow oil. $^1$H NMR δ (acetone-d$^6$) 10.25 (b, 1H), 8.32 (s, 1H), 7.97 (d, J=8.1 Hz, 1H), 7.93 (b, 1H), 7.70 (S, 2H), 1.36 (s, 18H).

Methyl 2-nitro-4-[(4'-bromo-5',6',7',8'-tetrahydro-5',5',8',8'-tetramethylnaphthalen-2'-yl)carbamoyl] benzoate (Compound 25)

Using the same procedure as for the synthesis of Compound 1, but using Compound F and Compound F$_1$, the desired product was obtained as a white solid.

$^1$H NMR δ 9.24 (b, 1H), 9.23 (d, J=1.8 Hz, 1H), 7.92 (dd, J=8.4, 2.4, Hz, 1H), 7.87 (d, J=2.1 Hz, 1H), 7.84 (d, 3=2.1 Hz, 1H), 7.80 (d, J=8.7 Hz, 1H), 3.91 (s, 3H), 1.75 (m, 2H), 1.65 (m, 2H), 1.58 (s, 3H), 1.33 (s, 3H).

General Procedure for the Syntheses of Benzoic Acid Derivatives by Hydrolyzing the Corresponding Methyl or Ethyl Esters.

To a solution of ester (3.0 mmol) in 20 ml of EtOH was added 5 ml of 1 N NaOH in water. The reaction mixture was stirred at room temperature for overnight and neutralized with 10% HCl to PH=5. The alcohol was removed by evaporation and the aqueous layer was extracted with ethyl acetate (3×10 ml). The combined ethyl acetate layers were washed with NaHCO$_3$ (sat.), brine and dried over MgSO$_4$. After concentration, the desired acid was obtained which could be recrystallized in ethyl acetate or in acetonitrile.

2-Fluoro-4-[(5',6',7',8'-tetrahydro-5',5',8',8'-tetramethylnaphthalen-2'-yl)carbamoyl]benzoic Acid (Compound 2)

$^1$H NMR δ (acetone-D$_6$) 9.86 (b, 1H), 7.95 (m, 3H), 7.75 (dd, J=7.9, 2.2 Hz, 1H), 7.62 (dd, J=8.5, 1.6 Hz, s e 1H), 7.50 (d, J=8.3 Hz, 1H), 1.73 (s, 4H), 1.32 (s, 6H), 1.30 (s, 6H).

2-Fluoro-4-[(4'-bromo-5',6',7',8'-tetrahydro-5',5',8',8'-tetramethylnaphthalen-2'-yl)carbamoyl]benzoic Acid (Compound 4)

$^1$H NMR δ (acetone-D$_6$) 9.97 (b, 1H), 8.04 (d, J=1.89 Hz, 1H), 8.01 (d, J=1.90 Hz, 1H), 7.95 (t, J=8.55 Hz, 1H), 7.90 (dd, J=12.28, 2.0 Hz, 1H), 7.59 (dd, J=8.67, 1.50 Hz, 1H), 1.76 (m, 4H), 1.58 (s, 6H), 1.35 (s, 6H).

2-Fluoro-4-[(3'-hydroxy-5',6',7',8'-tetrahydro-5',5',8',8'-tetramethylnaphthalen-2'-yl)carbamoyl]benzoic Acid (Compound 6)

$^1$H NMR (acetone-D$_6$) δ 11.3 (b, 1H), 10.2 (b, 1H), 7.94 (m. 2H), 7.85 (dd, J=11.4, 1.95 Hz, 1H), 7.53 (dd, J=6.59, 2.08 Hz, 1H), 6.94 (s, 1H), 2.85 (b, 1H), 1.70 (s, 4H), 1.29 (s, 6H), 1.28 (s, 12H).

2-Fluoro-4-[(8'-bromo-4',4'-dimethylchroman-6'-yl)carbamoyl]benzoic Acid (Compound 8)

$^1$H NMR (acetone-d$_6$) δ 9.87 (b, 1H), 8.04 (d, J=2.1 Hz, 1H), 8.03 (d, J=2.1 Hz, 1H), 7.94 (t, J=8.66 Hz, 1H), 7.91 (dd, J=13.8, 2.0 Hz, 1H), 7.57 (dd, J=8.6, 2.0 Hz, 1H), 4.37 (t, J=5.44 Hz, 2H), 1.92 (t, J=5.44 Hz, 2H), 1.40 (s, 6H).

2-Fluoro-4-[(2',2',4',4'-tetramethyl-8'-bromochroman-6'-yl)carbamoyl]benzoic Acid (Compound 10)

$^1$H NMR δ (acetone-d$_6$) 9.87 (b, 1H), 8.06 (d, J=2.2 Hz, 1H), 8.04 (d, J=2.1 Hz, 1H), 7.94 (t, J=8.54 Hz, 1H), 7.91 (dd, J=14.0, 2.0 Hz, 1H), 7.59 (dd, J=8.5, 2.3 Hz, 1H), 1.96 (s, 2H), 1.42 (s, 6H), 1.41 (s, 6H).

2-Fluoro-4-[(2',2',4',4'-tetramethyl-8'-trifluoromethylchroman-6'-yl)carbamoyl]benzoic Acid (Compound 12)

$^1$H NMR (acetone-d$_6$) δ 10.02 (b, 1H), 8.31 (s, 1H), 8.09 (s, 1H), 7.92 (m, 2H), 7.56 (d, J=7.69 Hz, 1H), 2.00 (s, 2H), 1.44 (s, 6H), 1.41 (s, 6H).

2-Fluoro-4-[(2',2',4',4'-tetramethyl-8'-azidochroman-6'-yl)carbamoyl]benzoic Acid (Compound 14)

$^1$H NMR δ 8.03 (t, J=8.4 Hz, 1H), 7.87 (b, 1H), 7.79 (dd, J=13, 2.0 Hz, 1H), 7.64 (d, J=2.2 Hz, 1H), 7.32 (dd, J=8.66, 1.9 Hz, 1H), 7.22 (d, J=2.1 Hz, 1H), 1.91 (s, 2H), 1.45 (s, 6H), 1.41 (s, 6H).

2,6-Difluoro-4-[(2',2',4',4'-tetramethyl-8'-trifluoromethylchroman-6'-yl)carbamoyl]benzoic acid (Compound 16)

$^1$H NMR (acetone-d$_6$) δ 8.30 (d, J=2.3 Hz, 1H), 8.06 (d, J=2.2 Hz, 1H), 7.59 (d, J=10.32 Hz, 2H), 1.954 (s, 2H), 1.44 (s, 6H), 1.41 (s, 6H).

2-Fluoro-4-[(2',2',4',4'-tetramethyl-8'-iodochroman-6'-yl)carbamoyl]benzoic Acid (Compound 18)

H NMR δ (acetone-d$_6$) 10.0 (b, 1H), 8.24 (s, 1H), 8.07 (s, 1H), 7.94 (m, 2H), 7.57 (d, J=8.67 Hz, 1H), 1.95 (s, 2H), 1.41 (s, 12H).

2-Fluoro-4-[(2',2',4',4',8'-entamethylchroman-6'-yl)carbamoyl]benzoic Acid (Compound 20)

$^1$H NMR δ (acetone-d$_6$) 9.77 (b, 1H), 7.90 (ml 3H), 7.65 (d, J=2.0 Hz, 1H), 7.56 (dd, J=8.61, 2.0 Hz, 1H), 2.19 (s, 3H), 1.90 (s, 2H), 1.38 (s, 6H), 1.37 (s, 6H).

4-[(5',6',7',8'-tetrahydro-5',5',8',8'-tetramethylnaphthalen-2'-yl)thiocarbamoyl]benzoic Acid (Compound 22)

$^1$H NMR δ 9.08 (b, 1H), 8.17 (d, J=8.61, 2H), 7.95 (b, 2H), 7.77 (b, 1H), 7.57 (dd, J=8.1, 2.1 Hz, 1H), 7.37 (d, J=8.2 Hz, 1H), 1.72 (s, 4H), 1.32 (s, 6H), 1.31 (s, 6H).

2-Fluoro-4-[(5',6',7',8'-tetrahydro-5',5',8',8'-tetramethylnaphthalen-2'-yl)thiocarbamoyl]benzoic Acid (Compound 24)

$^1$H NMR δ (acetone-d$_6$) 11.1 (b, 1H), 8.27 (b, J=13.2 Hz, 1H), 8.02 (t, J=8.3 Hz, 1H), 7.89 (s, 1H), 7.86 (d, J=10.0 Hz, 1H), 7.62 (d, J=8.3 Hz, 1H), 7.41 (d, J=8.37 Hz, 1H), 1.72 (s, 4H), 1.30 (s, 12H).

2-Fluoro-4-[(3'-hydroxy-4'-bromo-5',6',7',8'-tetrahydro-5',5',8',8'-tetramethylnaphthalen-2'-yl carbamoyl]benzoic Acid (Compound 30)

A solution of ethyl 2-fluoro-4-[(3'-methoxymethoxy-4'-bromo-5',6',7',8'-tetrahydro-5',5',8',8'-tetramethylnaphthalen-2'-yl)carbamoyl]benzoate (Compound S$_1$, 45 mg, 0.084 mmol) in 1 ml of EtOH was added 1 ml of aqueous solution of NaOH (1M). The reaction mixture was stirred at room temperature for overnight and acidified to PH=1 with 10% HCl. EtOH was removed and ethyl acetate and more water were added to the solution. The organic layer was separated and washed with NaHCO$_3$, brine and dried over MgSO₄. After filtration and concentration, the reaction yielded 2-fluoro-4-[(3'-methoxymethoxy-4'-bromo-5',6',7',8'-tetrahydro-5',5',8',8'-tetramethylnaphthalen-2'-yl)carbamoyl]benzoic acid as a white solid. The methoxymethyl group was removed by dissolving the white solid in 2 ml of MeOH and 3 drops of HCl (con.). After stirring for overnight, the reaction mixture was concentrated to dryness. The residue was partitioned between ethyl acetate and water. The organic layer was separated, washed with NaHCO₃, brine and dried over MgSO₄. After filtration and concentration, the residual solid was purified in a mini (pipette) column with ethyl acetate /hexane (1/1) to give the title compound as a white solid (5.0 mg).

¹H NMR d (acetone-d⁶) 10.19 (b, 1H), 8.01 (s, 1H), 7.96 (t, J=8.6 Hz, 1H), 7.76 (dd, J=11.2; 2.0 Hz, 1H), 7.54 (dd, J=8.8; 2.0 Hz, 1H), 1.75 (m, 2H), 1.65 (m, 2H), 1.61 (s, 6H), 1.32 (s, 6H).

2,6-Difluoro-4-[(3'-hydroxy-4'-bromo-5',6',7',8'-tetrahydro-5',5',8',8'-tetramethylnaphthalen-2'-yl) carbamoyl]benzoic Acid (Compound 32)

Using the same procedure as for the synthesis of 2-fluoro-4-[(3'-hydroxy-4'-bromo-5',6',7',8'-tetrahydro-5',5',8',8'-tetramethylnaphthalen-2'-yl)carbamoyl]benzoic acid (Compound 30) the title compound was obtained as a white solid.

¹H NMR d(acetone-d⁶) 10.23 (b, 1H), 8.01 (s, 1H), 7.52 (d, J=10.2 Hz, 2H), 4.8 (b, 1H), 1.75 (m, 2H), 1.65 (m, 2H), 1.60 (s, 6H), 1.31 (s, 6H).

2,6-Difluoro-4-[(5',6',7',8'-tetrahydro-5',5',8',8'-tetramethylnaphthalen-2'-yl)carbamoyl]benzoic Acid (Compound 34)

To 5,5,8,8-tetramethyl-5,6,7,8-tetrahydro-2-naphthoic acid (43 mg, 0.19 mmol) was added 1 ml of thionyl chloride. This mixture was refluxed for 2 h. Excess thionyl chloride was removed under reduced pressure and the residue was dissolved in 2 ml of CH₂Cl₂. To this solution was added methyl 4-amino-2,6-difluorobenzoate (Compound h₁, 7 mg, 0.2 mmol) followed by 0.5 ml of pyridine. The reaction mixture was stirred at room temperature for 4 h and was concentrated under reduced pressure. The residue was purified by column chromatography (ethyl acetate/hexane 1/5) to give the methyl ester of the desired product as a colorless oil.

¹H NMR d 8.11 (d, J=1.9 Hz, 1H), 8.05 (b, 1H), 7.86 (dd, J=6.2, 2.2 Hz, 1H), 7.41 (m, 3H), 3.93 (s, 3H), 1.69 (s, 4H), 1.29 (s, 6H), 1.28 (s, 6H). This colorless oil was hydrolyzed to the desired product with NaOH/H₂O/EtOH according to the general procedure.

¹H NMR d (acetone-d⁶) 9.74 (b, 1H), 7.95 (s, 1H), 7.70 (d, J=6.8 Hz, 1H), 7.43 (d, J=8.4 Hz, 3H), 1.71 (s, 4H), 1.29 (s, 6H), 1.28 (s, 6H).

2-Nitro-4-[(4'-bromo-5',6',7',8'-tetrahydro-5',5',8',8',-tetramethylnaphthalen-2'-yl)carbamoyl]benzoic acid (Compound 26)

¹H NMR δ (acetone-d⁶): 10.16 (b, 1H), 8.42 (d, J=2.0 Hz, 1H), 8.09 (dd, J=8.6; 2.1 Hz, 1H), 8.06 (d, J=2.2 Hz, 1H), 8.04 (d, J=2.2 Hz, 1H), 7.93 (d, J=8.6 Hz, 1H), 1.75 (m, 2H), 1.65 (m, 2H), 1.57 (s, 3H), 1.34 (s, 3H).

2-Fluoro-4-[(2',6'-di-t-butylpyrid-4'-yl)carbamoyl] benzoic Acid (Compound 42)

¹H NMR δ (CD₃OD) 7.92 (t, J=8.36 Hz, 1H), 7.82 (dd, J=12.82, 2.0 Hz, 1H), 7.63 (s, 2H), 7.55 (dd, J=8.7, 2.1 Hz, 1H), 1.39 (s, 18H).

4-[(2',6'-Di-t-butylpyrid-4'-yl) carbamoyl]benzoic acid (Compound 44)

¹H NMR δ (CD₃OD) 8.02 (d, J=8.85 Hz, 2H), 7.85 (d, J=8.85 Hz, 2H), 7.63 (S, 2H), 1.40 (s, 18H).

2-Fluoro-4-[(3',5'-di-t-butyl)phenylcarbamoyl] benzoic acid (Compound 46)

¹H NMR δ (CD₃OD) 7.92 (t, J=8.3 Hz, 1H), 7.80 (dd, J=12.8, 2.0 Hz, 1H), 7.79 (d, J=1.8 Hz, 2H), 7.69 (t, J=1.7 Hz, 1H), 7.57 (dd, J=8.7, 2.1 Hz, 1H), 1.37 (s, 18H).

2-Fluoro-4-[(2'-hydroxy-3',5'-di-t-butyl) phenylcarbamoyl]benzoic acid (Compound 48)

¹H NMR δ (acetone-d₆) 12.3 (b, 1H), 10.07 (b, 1H), 7.98 (t, J=8.48 Hz, 1H), 7.80 (m, 2H), 7.58 (d, J=2.3 Hz, 1H), 7.56 (dd, J=8.8, 2.0 Hz, 1H), 1.44 (s, 9H), 1.31 (s, 9H).

What is claimed is:

1. A process of administering to a mammal a retinoid compound which binds specifically or selectively to a RARα, retinoid receptors in preference over RARβ and RARγ retinoid receptors, for the purpose of treating or preventing a disease or condition which is responsive to treatment by RARα specific or selective retinoid agonists, said disease or condition being premalignant and malignant hyperproliferative diseases and Kaposi sarcoma where the RARα, specific or selective retinoid compound has the formula (i)

formula (i)

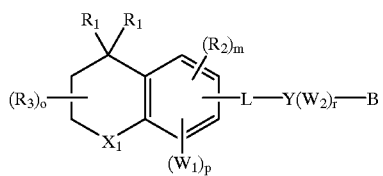

where X₁ is (C(R₁)₂)ₙ where n is an integer between 0 and 2;

R₁ is independently H or alkyl of 1 to 6 carbons;

R₂ is independently hydrogen, or lower alkyl of 1 to 6 carbons;

R₃ is hydrogen, lower alkyl of 1 to 6 carbons or F;

m is an integer having the value of 0–5;

o is an integer having the value of 0–4;

p is an integer having the value of 0–2;

r is an integer having the value 0–2;

Y is a phenyl or naphthyl group, said phenyl or naphthyl groups being optionally substituted with one or two R₂ groups;

W₁ is a substituent selected independently from the group consisting of F, Br, Cl, I, fluoro substituted C₁₋₆ alkyl, NO₂, and OH, with the provisos that:
(i) when Z is O then the sum of p and r is at least 1 and W₁ is not a fluoro, group in the 3 position of a tetrahydronaphthalene ring;
(ii) when r is zero and p is 1 and W₁ is OH then the OH group is positioned α to the L group;

W₂ is a substituent selected independently from the group consisting of F, Br, Cl, I, fluoro substituted C1–6 alkyl, NO₂, and OH;

L is —(C═Z)—NH— or —NH—(C═Z)—

Z is O or S, and

B is COOH or a pharmaceutically acceptable salt thereof, or COOR$_8$ where R$_8$ is an alkyl group of 1 to 10 carbons or trimethylsilylalkyl where the alkyl group has 1 to 10 carbons, or a cycloalkyl group of 5 to 10 carbons.

2. A process of administering to a mammal a retinoid compound which binds specifically or selectively to a RARα retinoid receptors in preference over RARβ and RARγ retinoid receptors, for the purpose of treating or preventing premalignant and malignant hyperproliferative diseases and Kaposi sarcoma, the retinoid compound being specific or selective for RARα retinoid receptors in preference over RARβ and RARγ retinoid receptors when in a binding assay the Kd value of binding to RARα receptors is approximately 500 times smaller than the Kd value for binding to RARβ and RARγ retinoid receptors, the retinoid compound having the formula (i)

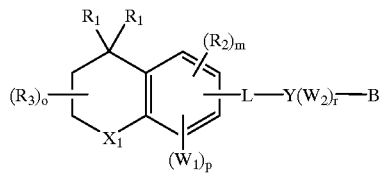

formula (i)

where X$_1$ is (C(R$_1$)$_2$)$_n$ where n is an integer between 0 and 2;

R$_1$ is independently H or alkyl of 1 to 6 carbons;

R$_2$ is independently hydrogen, or lower alkyl of 1 to 6 carbons;

R$_3$ is hydrogen, lower alkyl of 1 to 6 carbons or F;

m is an integer having the value of 0–5;

o is an integer having the value of 0–4;

p is an integer having the value of 0–2;

r is an integer having the value 0–2;

Y is a phenyl or naphthyl group, said phenyl or naphthyl groups being optionally substituted with one or two R$_2$ groups;

W$_1$ is a substituent selected independently from the group consisting of F, Br, Cl, I, fluoro substituted C$_{1-6}$ alkyl, NO$_2$, and OH, with the provisos that:
  (i) when Z is O then the sum of p and r is at least 1 and W$_1$ is not a fluoro, group in the 3 position of a tetrahydronaphthalene ring;
  (ii) when r is zero and p is 1 and W$_1$ is OH then the OH group is positioned α to the L group;

W$_2$ is a substituent selected independently from the group consisting of F, Br, Cl, I, fluoro substituted C1–6 alkyl, NO$_2$, and OH;

L is —(C═Z)—NH— or —NH—(C═Z)—

Z is O or S, and

B is COOH or a pharmaceutically acceptable salt thereof, or COOR$_8$ where R$_8$ is an alkyl group of 1 to 10 carbons or trimethylsilylalkyl where the alkyl group has 1 to 10 carbons, or a cycloalkyl group of 5 to 10 carbons.

3. A process in accordance with claim 2 where Y is phenyl.

* * * * *